US009163330B2

(12) United States Patent
Verdine et al.

(10) Patent No.: US 9,163,330 B2
(45) Date of Patent: Oct. 20, 2015

(54) BIFUNCTIONAL STAPLED POLYPEPTIDES AND USES THEREOF

(75) Inventors: Gregory L. Verdine, Boston, MA (US); Tom N. Grossmann, Berlin (DE); Raymond E. Moellering, La Jolla, CA (US); Tsung-Han Johannes Yeh, Jamaica Plain, MA (US); Yue Rebecca Yue Liang, Cambridge, MA (US); Youbean Oak, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 285 days.

(21) Appl. No.: 13/383,881

(22) PCT Filed: Jul. 13, 2010

(86) PCT No.: PCT/US2010/001952

§ 371 (c)(1), (2), (4) Date: Jul. 6, 2012

(87) PCT Pub. No.: WO2011/008260

PCT Pub. Date: Jan. 20, 2011

(65) Prior Publication Data

US 2012/0270800 A1 Oct. 25, 2012

Related U.S. Application Data

(60) Provisional application No. 61/225,191, filed on Jul. 13, 2009.

(51) Int. Cl.

| | |
|---|---|
| ***A61K 38/00*** | (2006.01) |
| ***A61K 38/16*** | (2006.01) |
| ***A61P 35/00*** | (2006.01) |
| ***C07K 14/00*** | (2006.01) |
| ***C07K 1/107*** | (2006.01) |
| ***C40B 30/04*** | (2006.01) |
| ***A61K 47/48*** | (2006.01) |
| ***C07K 14/47*** | (2006.01) |
| ***C07K 14/435*** | (2006.01) |
| ***C12N 9/00*** | (2006.01) |
| ***C07K 1/113*** | (2006.01) |

(52) U.S. Cl.

CPC .......... *C40B 30/04* (2013.01); *A61K 47/48215* (2013.01); *A61K 47/48238* (2013.01); *A61K 47/48246* (2013.01); *A61K 47/48338* (2013.01); *A61K 47/48346* (2013.01); *C07K 1/107* (2013.01); *C07K 1/1077* (2013.01); *C07K 1/113* (2013.01); *C07K 14/435* (2013.01); *C07K 14/47* (2013.01); *C07K 14/4747* (2013.01); *C12N 9/93* (2013.01); *C12Y 603/02019* (2013.01); *A61K 38/00* (2013.01); *C07K 2319/00* (2013.01); *C07K 2319/01* (2013.01)

(58) Field of Classification Search

None

See application file for complete search history.

(56) References Cited

U.S. PATENT DOCUMENTS

| | | | |
|---|---|---|---|
| 4,270,537 | A | 6/1981 | Romaine |
| 4,596,556 | A | 6/1986 | Morrow et al. |
| 4,730,006 | A | 3/1988 | Bohme et al. |
| 4,790,824 | A | 12/1988 | Morrow et al. |
| 4,886,499 | A | 12/1989 | Cirelli et al. |
| 4,940,460 | A | 7/1990 | Casey et al. |
| 4,941,880 | A | 7/1990 | Burns |
| 5,015,235 | A | 5/1991 | Crossman |
| 5,064,413 | A | 11/1991 | McKinnon et al. |
| 5,120,859 | A | 6/1992 | Webb |
| 5,141,496 | A | 8/1992 | Dalto et al. |
| 5,190,521 | A | 3/1993 | Hubbard et al. |
| 5,312,335 | A | 5/1994 | McKinnon et al. |
| 5,328,483 | A | 7/1994 | Jacoby |
| 5,334,144 | A | 8/1994 | Alchas et al. |
| 5,339,163 | A | 8/1994 | Homma et al. |
| 5,364,851 | A | 11/1994 | Joran |
| 5,383,851 | A | 1/1995 | McKinnon et al. |
| 5,417,662 | A | 5/1995 | Hjertman et al. |
| 5,446,128 | A | 8/1995 | Kahn |

(Continued)

FOREIGN PATENT DOCUMENTS

| | | | |
|---|---|---|---|
| WO | WO 96/02642 | A1 | 2/1996 |
| WO | WO 96/34878 | A1 | 11/1996 |

(Continued)

OTHER PUBLICATIONS

Sadot, Molecular and Cellular Biology (2001) 21(20), 6768-6781.*

Extended European Search Report for EP 09800675.2, mailed Dec. 6, 2012.

Extended European Search Report for EP 12159110.1, mailed Jul. 20, 2012.

Extended European Search Report for EP 12159110.1, mailed Sep. 27, 2012.

(Continued)

*Primary Examiner* — Karlheinz R Skowronek

*Assistant Examiner* — Catherine Mader

(74) *Attorney, Agent, or Firm* — Wolf, Greenfield & Sacks, P.C.

(57) ABSTRACT

The invention relates to bifunctional stapled or stitched peptides comprising a targeting domain, a linker moiety, and an effector domain, that can be used to tether, or to bring into close proximity, at least two cellular entities (e.g., proteins). Certain aspects relate to bifunctional stapled or stitched peptides that bind to an effector biomolecule through the effector domain and bind to a target biomolecule through the targeting domain. Polypeptides and/or polypeptide complexes that are tethered by the bifunctional stapled or stitched peptides of the invention, where the effector polypeptide bound to the effector domain of the bifunctional stapled or stitched peptide modifies or alters the target polypeptide bound to the targeting domain of the bifunctional peptide. Uses of the inventive bifunctional stapled or stitched peptides including methods for treatment of disease (e.g., cancer, inflammatory diseases) are also provided.

56 Claims, 24 Drawing Sheets

(56) References Cited

U.S. PATENT DOCUMENTS

| | | | |
|---|---|---|---|
| 5,466,220 | A | 11/1995 | Brenneman |
| 5,480,381 | A | 1/1996 | Weston |
| 5,503,627 | A | 4/1996 | McKinnon et al. |
| 5,520,639 | A | 5/1996 | Peterson et al. |
| 5,527,288 | A | 6/1996 | Gross et al. |
| 5,569,189 | A | 10/1996 | Parsons |
| 5,599,302 | A | 2/1997 | Lilley et al. |
| 5,622,852 | A | 4/1997 | Korsmeyer |
| 5,649,912 | A | 7/1997 | Peterson |
| 5,663,316 | A | 9/1997 | Xudong |
| 5,704,911 | A | 1/1998 | Parsons |
| 5,708,136 | A | 1/1998 | Burrell et al. |
| 5,750,767 | A | 5/1998 | Carpino et al. |
| 5,811,515 | A | 9/1998 | Grubbs et al. |
| 5,824,483 | A | 10/1998 | Houston, Jr. et al. |
| 5,834,209 | A | 11/1998 | Korsmeyer |
| 5,856,445 | A | 1/1999 | Korsmeyer |
| 5,874,529 | A | 2/1999 | Gilon et al. |
| 5,893,397 | A | 4/1999 | Peterson et al. |
| 5,922,863 | A | 7/1999 | Grubbs et al. |
| 5,955,593 | A | 9/1999 | Korsmeyer |
| 5,965,703 | A | 10/1999 | Horne et al. |
| 5,993,412 | A | 11/1999 | Deily et al. |
| 5,998,583 | A | 12/1999 | Korsmeyer |
| 6,051,554 | A | 4/2000 | Hornik et al. |
| 6,153,391 | A | 11/2000 | Picksley et al. |
| 6,184,344 | B1 | 2/2001 | Kent et al. |
| 6,271,198 | B1 * | 8/2001 | Braisted et al. ................ 514/3.8 |
| 6,326,354 | B1 | 12/2001 | Gross et al. |
| 6,610,657 | B1 | 8/2003 | Goueli |
| 6,613,874 | B1 | 9/2003 | Mazur et al. |
| 6,703,382 | B2 | 3/2004 | Wang et al. |
| 6,713,280 | B1 | 3/2004 | Huang et al. |
| 6,849,428 | B1 | 2/2005 | Evans et al. |
| 6,875,594 | B2 | 4/2005 | Muir et al. |
| 7,064,193 | B1 | 6/2006 | Cory et al. |
| 7,083,983 | B2 | 8/2006 | Lane et al. |
| 7,084,244 | B2 | 8/2006 | Gilon et al. |
| 7,183,059 | B2 | 2/2007 | Verdine et al. |
| 7,192,713 | B1 | 3/2007 | Verdine et al. |
| 7,202,332 | B2 | 4/2007 | Arora et al. |
| 7,247,700 | B2 | 7/2007 | Korsmeyer et al. |
| 7,538,190 | B2 | 5/2009 | Robinson et al. |
| 7,705,118 | B2 | 4/2010 | Arora et al. |
| 7,723,469 | B2 | 5/2010 | Walensky et al. |
| 7,745,573 | B2 | 6/2010 | Robinson et al. |
| 7,786,072 | B2 | 8/2010 | Verdine et al. |
| 8,324,428 | B2 | 12/2012 | Verdine et al. |
| 8,592,377 | B2 | 11/2013 | Verdine et al. |
| 8,895,699 | B2 | 11/2014 | Verdine et al. |
| 2004/0023887 | A1 | 2/2004 | Pillutla et al. |
| 2004/0038901 | A1 | 2/2004 | Basler et al. |
| 2004/0067503 | A1 | 4/2004 | Tan et al. |
| 2004/0171809 | A1 | 9/2004 | Korsmeyer et al. |
| 2005/0250680 | A1 | 11/2005 | Walensky et al. |
| 2006/0008848 | A1 | 1/2006 | Verdine et al. |
| 2006/0014675 | A1 | 1/2006 | Arora et al. |
| 2008/0262200 | A1 | 10/2008 | Nash |
| 2009/0047711 | A1 | 2/2009 | Nash |
| 2009/0088553 | A1 | 4/2009 | Nash |
| 2009/0149630 | A1 | 6/2009 | Walensky et al. |
| 2009/0176964 | A1 | 7/2009 | Walensky et al. |
| 2009/0326192 | A1 | 12/2009 | Nash et al. |
| 2010/0081611 | A1 | 4/2010 | Bradner et al. |
| 2010/0168388 | A1 | 7/2010 | Bernal et al. |
| 2010/0184628 | A1 | 7/2010 | Nash |
| 2010/0184645 | A1 | 7/2010 | Verdine et al. |
| 2010/0216688 | A1 | 8/2010 | Nash et al. |
| 2010/0234563 | A1 | 9/2010 | Arora et al. |
| 2010/0298201 | A1 | 11/2010 | Nash et al. |
| 2011/0028753 | A1 | 2/2011 | Verdine et al. |
| 2011/0144303 | A1 | 6/2011 | Nash et al. |
| 2011/0144306 | A1 | 6/2011 | Verdine et al. |
| 2011/0223149 | A1 | 9/2011 | Nash et al. |
| 2011/0263815 | A1 | 10/2011 | Nash |
| 2012/0082636 | A1 | 4/2012 | Walensky et al. |
| 2012/0172311 | A1 | 7/2012 | Nash et al. |
| 2012/0190818 | A1 | 7/2012 | Nash |
| 2013/0005943 | A1 | 1/2013 | Arora et al. |
| 2013/0023646 | A1 | 1/2013 | Nash et al. |
| 2013/0211046 | A1 | 8/2013 | Verdine et al. |
| 2014/0005118 | A1 | 1/2014 | Verdine et al. |
| 2014/0011979 | A1 | 1/2014 | Verdine et al. |
| 2014/0162339 | A1 | 6/2014 | Verdine et al. |
| 2014/0235549 | A1 | 8/2014 | Moellering et al. |
| 2014/0256912 | A1 | 9/2014 | Moellering et al. |

FOREIGN PATENT DOCUMENTS

| | | | |
|---|---|---|---|
| WO | WO 97/13537 | A1 | 4/1997 |
| WO | WO 97/37705 | A1 | 10/1997 |
| WO | WO 99/34850 | A1 | 7/1999 |
| WO | WO 00/06187 | A2 | 2/2000 |
| WO | WO 02/064790 | A2 | 8/2002 |
| WO | WO 03/106491 | A2 | 12/2003 |
| WO | WO 03/106491 | A3 | 12/2003 |
| WO | WO 2004/041275 | A1 | 5/2004 |
| WO | WO 2004/058804 | A1 | 7/2004 |
| WO | WO 2005/040202 | A2 | 5/2005 |
| WO | WO 2005/040202 | A3 | 5/2005 |
| WO | WO 2005/044839 | A2 | 5/2005 |
| WO | WO 2005/044839 | A3 | 5/2005 |
| WO | WO 2005/085457 | A2 | 9/2005 |
| WO | WO 2005/090388 | A1 | 9/2005 |
| WO | WO 2005/118620 | A2 | 12/2005 |
| WO | WO 2005/118620 | A3 | 12/2005 |
| WO | WO 2005/118634 | A2 | 12/2005 |
| WO | WO 2005/118634 | A3 | 12/2005 |
| WO | WO 2006/103666 | A2 | 10/2006 |
| WO | WO 2007/141533 | A2 | 12/2007 |
| WO | WO 2008/061192 | A2 | 5/2008 |
| WO | WO 2008/095063 | A1 | 8/2008 |
| WO | WO 2008/121767 | A2 | 10/2008 |
| WO | WO 2009/042237 | A2 | 4/2009 |
| WO | WO 2009/126292 | A2 | 10/2009 |
| WO | WO 2010/011313 | A2 | 1/2010 |
| WO | WO 2010/034029 | A1 | 3/2010 |
| WO | WO 2010/068684 | A2 | 6/2010 |
| WO | WO 2011/008260 | A2 | 1/2011 |
| WO | WO 2012/040459 | A2 | 3/2012 |
| WO | WO 2012/174423 | A1 | 12/2012 |
| WO | WO 2014/052647 | A2 | 4/2014 |
| WO | WO 2014/055564 | A1 | 4/2014 |

OTHER PUBLICATIONS

International Preliminary Report on Patentability for PCT/US2011/052755, mailed Apr. 4, 2013.

International Search Report and Written Opinion for PCT/US2012/042738, mailed Oct. 18, 2012.

International Search Report and Written Opinion for PCT/US2008/052580, mailed May 16, 2008.

Office Communication, mailed Feb. 9, 2012, for U.S. Appl. No. 12/420,816.

Notice of Allowance, mailed Aug. 6, 2012, for U.S. Appl. No. 12/796,212.

Office Communication, mailed Apr. 22, 2013, for U.S. Appl. No. 13/055,279.

Office Communication, mailed Jan. 3, 2013, for U.S. Appl. No. 12/593,384.

Notice of Allowance, mailed May 30, 2013, for U.S. Appl. No. 12/593,384.

[No Author Listed] Designing Custom Peptide. from SIGMA Genosys, pp. 1-2. Accessed Jul. 27, 2012.

Agola et al., Rab GTPases as regulators of endocytosis, targets of disease and therapeutic opportunities. Clin Genet. Oct. 2011; 80(4): 305-318.

Altschul et al., Basic local alignment search tool. J Mol Biol. Oct. 5, 1990;215(3):403-10.

Berendsen et al., A glimpse of the Holy Grail? Science. Oct. 23, 1998;282(5389):642-3.

Blundell et al., Atomic positions in rhombohedral 2-zinc insulin crystals. Nature. Jun. 25, 1971;231(5304):506-11.

(56) References Cited

OTHER PUBLICATIONS

Bradley et al., Limits of cooperativity in a structurally modular protein: response of the Notch ankyrin domain to analogous alanine substitutions in each repeat. J Mol Biol. Nov. 22, 2002;324(2):373-86.
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Carillo et al., The Multiple Sequence Alignment Problem in Biology. SIAM J Applied Math. 1988;48:1073-82.
Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.
Chen et al., Determination of the helix and beta form of proteins in aqueous solution by circular dichroism. Biochemistry. Jul. 30, 1974;13(16):3350-9.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Chia et al., Emerging roles for Rab family GTPases in human cancer. Biochim Biophys Acta. Apr. 2009;1795(2):110-6.
David et al., Expressed protein ligation. Method and applications. Eur J Biochem. Feb. 2004;271(4):663-77.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
Devereux et al., A comprehensive set of sequence analysis programs for the VAX. Nucleic Acids Res. Jan. 11, 1984;12(1 Pt 1):387-95.
Evans et al., The Rise of Azide—Alkyne 1,3-Dipolar 'Click' Cycloaddition and its Application to Polymer Science and Surface Modification. Australian Journal of Chemistry. 2007;60:384-95.
Fisher et al., Myc/Max and other helix-loop-helix/leucine zipper proteins bend DNA toward the minor groove. Proc Natl Acad Sci U S A. Dec. 15, 1992;89(24):11779-83.
Gentle et al., Direct production of proteins with N-terminal cysteine for site-specific conjugation. Bioconjug Chem. May-Jun. 2004;15(3):658-63.
Harris et al., Synthesis of proline-modified analogues of the neuroprotective agent glycyl-l-prolyl-glutamic acid (GPE). Tetrahedron. 2005;61:10018-35.
Hellman et al., Electrophoretic mobility shift assay (EMSA) for detecting protein-nucleic acid interactions. Nat Protoc. 2007;2(8):1849-61.
Huang et al., How insulin binds: the B-chain alpha-helix contacts the L1 beta-helix of the insulin receptor. J Mol Biol. Aug. 6, 2004;341(2):529-50.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Junutula et al., Molecular characterization of Rab11 interactions with members of the family of Rab11-interacting proteins. J Biol Chem. Aug. 6, 2004;279(32):33430-7. Epub Jun. 1, 2004.
Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.
Kohler et al., DNA specificity enhanced by sequential binding of protein monomers. Proc Natl Acad Sci U S A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.
Luscher et al., The basic region/helix-loop-helix/leucine zipper domain of Myc proto-oncoproteins: function and regulation. Oncogene. May 13, 1999;18(19):2955-66.
Marshall et al., Back to the future: ribonuclease A. Biopolymers. 2008;90(3):259-77.
McKern et al., Structure of the insulin receptor ectodomain reveals a folded-over conformation. Nature. Sep. 14, 2006;443(7108):218-21. Epub Sep. 6, 2006.
McNamara et al., Peptides constrained by an aliphatic linkage between two C(alpha) sites: design, synthesis, and unexpected conformational properties of an i,(i + 4)-linked peptide. J Org Chem. Jun. 29, 2001;66(13):4585-94.
Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.
Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.
Mynarcik et al., Alanine-scanning mutagenesis of a C-terminal ligand binding domain of the insulin receptor alpha subunit. J Biol Chem. Feb. 2, 1996;271(5):2439-42.
Mynarcik et al., Identification of common ligand binding determinants of the insulin and insulin-like growth factor 1 receptors. Insights into mechanisms of ligand binding. J Biol Chem. Jul. 25, 1997;272(30):18650-5.
Ngo et al., Computational complexity, protein structure prediction, and the levinthal paradox. In: The Protein Folding Problem and Tertiary Structure Prediction. K. Mem, Jr., et al. Eds. 1994:433-506.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Rudinger, Characteristics of the amino acids as components of a peptide hormone sequence. In: Peptide Hormones. J. A. Parsons, ed. University Park Press. Jun. 1976:1-7.
Schäffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schäffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schinzel et al., The phosphate recognition site of *Escherichia coli* maltodextrin phosphorylase. FEBS Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Seabra et al., Rab GTPases, intracellular traffic and disease. Trends Mol Med. Jan. 2002;8(1):23-30.

(56) References Cited

OTHER PUBLICATIONS

Shiba et al., Structural basis for Rab11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.
Siddle et al., Specificity in ligand binding and intracellular signalling by insulin and insulin-like growth factor receptors. Biochem Soc Trans. Aug. 2001;29(Pt 4):513-25.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Stein et al., Rab proteins and endocytic trafficking: potential targets for therapeutic intervention. Adv Drug Deliv Rev. Nov. 14, 2003;55(11):1421-37.
Stenmark et al., The Rab GTPase family. Genome Biol. 2001;2(5):3007.1-3007.7.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Tanaka, Design and synthesis of non-proteinogenic amino acids and secondary structures of their peptides. Yakugaku Zasshi. Oct. 2006:126(10):931-44. Japanese.
Tolbert et al., New methods for proteomic research: preparation of proteins with N-terminal cysteines for labeling and conjugation. Angew Chem Int Ed Engl. Jun. 17, 2002;41(12):2171-4.
Tornøe et al., Peptidotriazoles on solid phase: [1,2,3]-triazoles by regiospecific copper(i)-catalyzed 1,3-dipolar cycloadditions of terminal alkynes to azides. J Org Chem. May 3, 2002;67(9):3057-64.
Uesugi et al., The alpha-helical FXXPhiPhi motif in p53: TAF interaction and discrimination by MDM2. Proc Natl Acad Sci U S A. Dec. 21, 1999;96(26):14801-6.
Voet et al., Biochemistry. Second Edition. John Wiley & Sons, Inc. 1995:235-241.
Wang, 4-Alkyl-2-trichloromethyloxazolidin-5-ones: Valuable Precursors to Enantiomerically Pure C- and N-Protected α-Alkyl Prolines. Synlett. 1999;1:33-36.
Wei et al., Disorder and structure in the Rab11 binding domain of Rab11 family interacting protein 2. Biochemistry. Jan. 27, 2009;48(3):549-57. doi: 10.1021/bi8020197.
Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.
Zimm et al., Theory of the Phase Transition between Helix and Random Coil in Polypeptide Chains. J Chem Phys. 1959;31:526-35.
Invitation to Pay Additional Fees for PCT/US2010/001952 mailed Oct. 29, 2010.
International Search Report and Written Opinion for PCT/US2010/001952 mailed Feb. 2, 2011.
International Preliminary Report on Patentability for PCT/US2010/001952 Jan. 26, 2012.
Invitation to Pay Additional Fees for PCT/US2009/004260 mailed Mar. 19, 2010.
International Search Report and Written Opinion for PCT/US2009/004260 mailed Oct. 15, 2010.
International Preliminary Report on Patentability for PCT/US2009/004260 mailed Feb. 3, 2011.
International Search Report and Written Opinion for PCT/US2008/058575 mailed Nov. 17, 2008.
International Preliminary Report on Patentability for PCT/US2008/058575 mailed Oct. 8, 2009.
Invitation to Pay Additional Fees for PCT/US2011/052755 mailed Feb. 16, 2012.
International Search Report and Written Opinion for PCT/US2011/052755 mailed Apr. 25, 2012.
Office Communication, mailed Feb. 17, 2011, for U.S. Appl. No. 12/796,212.
Office Communication, mailed Oct. 18, 2011, for U.S. Appl. No. 12/796,212.
Adhikary et al., Transcriptional regulation and transformation by Myc proteins. Nat Rev Mol Cell Biol. Aug. 2005;6(8):635-45.
Aman et al., cDNA cloning and characterization of the human interleukin 13 receptor alpha chain. J Biol Chem. Nov. 15, 1996;271(46):29265-70.
Andrews et al., Forming Stable Helical Peptides Using Natural and Artificial Amino Acids. Tetrahedron. 1999;55:11711-43.
Andrews et al., Kinetic analysis of the interleukin-13 receptor complex. J Biol Chem. Nov. 29, 2002;277(48):46073-8. Epub Sep. 26, 2002.
Armstrong et al., X = Y-ZH Systems as potential 1,3-dipoles. 5. Intramolecular cycloadditions of imines of a-amino acid esters. Tetrahedron. 1985;41(17):3547-58.
Attisano et al., TGFbeta and Wnt pathway cross-talk. Cancer Metastasis Rev. Jan.-Jun. 2004;23(1-2):53-61.
Babine et al., Molecular Recognition of Proteinminus signLigand Complexes: Applications to Drug Design. Chem Rev. Aug. 5, 1997;97(5):1359-1472.
Banerjee et al., Structure of a DNA glycosylase searching for lesions. Science. Feb. 24, 2006;311(5764):1153-7.
Banerjee et al., Structure of a repair enzyme interrogating undamaged DNA elucidates recognition of damaged DNA. Nature. Mar. 31, 2005;434(7033):612-8.
Bang et al., Total chemical synthesis of crambin. J Am Chem Soc. Feb. 11, 2004;126(5):1377-83.
Barandon et al., Reduction of infarct size and prevention of cardiac rupture in transgenic mice overexpressing FrzA. Circulation. Nov. 4, 2003;108(18):2282-9. Epub Oct. 27, 2003.
Barker et al., Mining the Wnt pathway for cancer therapeutics. Nat Rev Drug Discov. Dec. 2006;5(12):997-1014.
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (*S*)-2-[*N*-(*N*'-benzyl-prolyl)amino]benzophenone (BPB) and Ni(II) complexes of Schiff's bases derived from BPB and amino acids. Tetrahedron: Asymmetry. 1998;9:4249-52.
Bennett et al., Regulation of osteoblastogenesis and bone mass by Wnt10b. Proc Natl Acad Sci U S A. Mar. 1, 2005;102(9):3324-9. Epub Feb. 22, 2005.
Berge et al., Pharmaceutical salts. J Pharm Sci. Jan. 1977;66(1):1-19.
Bernal et al., Reactivation of the p53 tumor suppressor pathway by a stapled p53 peptide. J Am Chem Soc. Mar. 7, 2007;129(9):2456-7. Epub Feb. 7, 2007.
Biagini et al., Cross-metathesis of Unsaturated α-amino Acid Derivatives. J Chem Soc Perkin Trans. 1998;1:2485-99.
Bierzynski et al., A salt bridge stabilizes the helix formed by isolated C-peptide of Rnase A. Proc Natl Acad Sci U S A. Apr. 1982;79(8):2470-4.
Blackwell et al., Highly Efficient Synthesis of Covalently Cross-Linked Peptide Helices by Ring-Closing Metathesis. Angew Chem Int Ed. 1994;37(23):3281-84.
Blackwell et al., Ring-closing metathesis of olefinic peptides: design, synthesis, and structural characterization of macrocyclic helical peptides. J Org Chem. Aug. 10, 2001;66(16):5291-302.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boyden et al., High bone density due to a mutation in LDL-receptor-related protein 5. N Engl J Med. May 16, 2002;346(20):1513-21.
Bracken et al., Synthesis and Nuclear Magnetic Resonance Structure Determination of an α-Helical, Bicyclic, Lactam-Bridged Hexapeptide. J Am Chem Soc. 1994;116:6431-32.

(56) References Cited

OTHER PUBLICATIONS

Brubaker et al., Solution structure of the interacting domains of the Mad-Sin3 complex: implications for recruitment of a chromatin-modifying complex. Cell. Nov. 10, 2000;103(4):655-65.
Brusselle et al., Allergen-induced airway inflammation and bronchial responsiveness in wild-type and interleukin-4-deficient mice. Am J Respir Cell Mol Biol. Mar. 1995;12(3):254-9.
Burger et al., Synthesis of a-(trifluoromethyl)-substituted a-amino acids. Part 7. An efficient synthesis for a-trifluoromethyl-substituted w-carboxy a-amino acids. Chemiker-Zeitung. 1990;114(3):101-04. German.
Caricasole et al., The Wnt pathway, cell-cycle activation and beta-amyloid: novel therapeutic strategies in Alzheimer's disease? Trends Pharmacol Sci. May 2003;24(5):233-8.
Chen et al., Small molecule-mediated disruption of Wnt-dependent signaling in tissue regeneration and cancer. Nat Chem Biol. Feb. 2009;5(2):100-7. Epub Jan. 4, 2009.
Cheon et al., beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chiaramonte et al., Studies of murine schistosomiasis reveal interleukin-13 blockade as a treatment for established and progressive liver fibrosis. Hepatology. Aug. 2001;34(2):273-82.
Christodoulides et al., WNT10B mutations in human obesity. Diabetologia. Apr. 2006;49(4):678-84. Epub Feb. 14, 2006.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Thl, cells. J Immunol. Oct. 15, 1998;161(8):3813-6.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Cossu et al., Wnt signaling and the activation of myogenesis in mammals. EMBO J. Dec. 15, 1999;18(24):6867-72.
Cusack et al., 2,4,6-Tri-isopropylbenzenesulphonyl Hydrazide: A Convenient Source of Di-imide. Tetrahedron. 1976;32:2157-62.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
Debinski et al., Retargeting interleukin 13 for radioimmunodetection and radioimmunotherapy of human high-grade gliomas. Clin Cancer Res. Oct. 1999;5(10 Suppl):3143s-3147s.
Denmark et al., Cyclopropanation with Diazomethane and Bis(oxazoline)palladium(II) Complexes. J Org Chem. May 16, 1997;62(10):3375-3389.
Doron et al., Probiotics: their role in the treatment and prevention of disease. Expert Rev Anti Infect Ther. 2006;4:261-75.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Erlanson et al., The leucine zipper domain controls the orientation of AP-1 in the NFAT.AP-1.DNA complex. Chem Biol. Dec. 1996;3(12):981-91.
Favrin et al., Two-state folding over a weak free-energy barrier. Biophys J. Sep. 2003;85(3):1457-65.
Fischback et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Fromme et al., Structural basis for removal of adenine mispaired with 8-oxoguanine by MutY adenine DNA glycosylase. Nature. Feb. 12, 2004;427(6975):652-6.
Fuchs et al., Socializing with the neighbors: stem cells and their niche. Cell. Mar. 19, 2004;116(6):769-78.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(*t*-Bu)(AR)]$_3$ Complexes as Catalyst Precursors: In Situ Activation and Application to Metathesis Reactions of Alkynes and Diynes. J Am Chem Soc. 1999;121:9453-54.
Furstner et al., Nozaki—Hiyama—Kishi Reactions Catalytic in Chromium. J Am Chem Soc. 1996:118:12349-57.
Gallivan et al., A neutral, water-soluble olefin metathesis catalyst based on an *N*-heterocyclic carbene ligand. Tetrahedron Letters. 2005;46:2577-80.
Gante, Peptidomimetics—Tailored Enzyme Inhibitors. J Angew Chem Int Ed Engl. 1994;33:1699-1720.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Gerber-Lemaire et al., Glycosylation pathways as drug targets for cancer: glycosidase inhibitors. Mini Rev Med Chem. Sep. 2006;6(9):1043-52.
Giannis et al., Peptidomimetics for Receptor Ligands—Discovery, Development, and Medical Perspectives. Angew Chem Int Ed Engl. 1993;32:1244-67.
Gong et al., LDL receptor-related protein 5 (LRP5) affects bone accrual and eye development. Cell. Nov. 16, 2001;107(4):513-23.
Goodson et al., Potential Growth Antagonists. I. Hydantoins and Disubstituted Glycines. J Org Chem. 1960;25:1920-24.
Görlich et al., Transport between the cell nucleus and the cytoplasm. Annu Rev Cell Dev Biol. 1999;15:607-60.
Goun et al., Molecular transporters: synthesis of oligoguanidinium transporters and their application to drug delivery and real-time imaging. Chembiochem. Oct. 2006;7(10):1497-515.
Greenfield et al., Computed circular dichroism spectra for the evaluation of protein conformation. Biochemistry. Oct. 1969;8(10):4108-16.
Greenlee et al., A General Synthesis of $\alpha$-vinyl-$\alpha$-amino acids. Tetrahedron Letters. 1978;42:3999-40002.
Grubbs et al., Ring-Closing Metathesis and Related Processes in Organic Synthesis. Acc Chem Res. 1995;28:446-52.
Grünig et al., Requirement for IL-13 independently of IL-4 in experimental asthma. Science. Dec. 18, 1998;282(5397):2261-3.
Guinn et al., Synthesis and characterization of polyamides containing unnatural amino acids. Biopolymers. May 1995;35(5):503-12.
Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.
Hartmann et al., Dual roles of Wnt signaling during chondrogenesis in the chicken limb. Development. Jul. 2000;127(14):3141-59.
Hartmann, A Wnt canon orchestrating osteoblastogenesis. Trends Cell Biol. Mar. 2006;16(3):151-8. Epub Feb. 7, 2006.
Henchey et al., Contemporary strategies for the stabilization of peptides in the $\alpha$-helical conformation. Curr Opin Chem Biol. 2008;12:692-97.
Hipfner et al., Connecting proliferation and apoptosis in development and disease. Nat Rev Mol Cell Biol. Oct. 2004;5(10):805-15.
Hoang et al., Dickkopf 3 inhibits invasion and motility of Saos-2 osteosarcoma cells by modulating the Wnt-beta-catenin pathway. Cancer Res. Apr. 15, 2004;64(8):2734-9.
Holford et al., Adding 'splice' to protein engineering. Structure. Aug. 15, 1998;6(8):951-6.

(56) References Cited

OTHER PUBLICATIONS

Huang et al., Tankyrase inhibition stabilizes axin and antagonizes Wnt signalling. Nature. Oct. 1, 2009;461(7264):614-20. Epub Sep. 16, 2009.
Jackson et al., General Approach to the Synthesis of Short α-Helical Peptides. J Am Chem Soc. 1991;113:9391-92.
Jamieson et al., Granulocyte-macrophage progenitors as candidate leukemic stem cells in blast-crisis CML. N Engl J Med. Aug. 12, 2004;351(7):657-67.
Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.
Karwoski et al., Lysinonorleucine cross-link formation in alpha amino heptenoic acid-substituted peptide derivatives. Biopolymers. 1978;17(5):1119-27.
Katoh et al., Cross-talk of Wnt and FGF signaling pathways at GSK3beta to regulate betacatenin and SNAIL signaling cascades. Cancer Biol Ther. Sep. 2006;5(9):1059-64. Epub Sep. 4, 2006.
Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul et al., Stereochemical control of peptide folding. Bioorg Med Chem. Jan. 1999;7(1):105-17.
Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.
Kazmaier, Sythesis of Quaternary Amino Acids Containing β, γ- as well as γ,δ-Unsaturated Side Chains via Chelate-Enolate Claisen Rearrangement. Tetrahedron Letters. 1996;37(30):5351-4.
Kelly-Welch et al., Interleukin-4 and Interleukin-13 Signaling Connections Maps. Science. 2003;300:1527-28.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kimmerlin et al., '100 years of peptide synthesis': ligation methods for peptide and proteinsynthesis with applications to beta-peptide assemblies. J Pept Res. Feb. 2005;65(2):229-60.
Kinzler et al., Identification of FAP locus genes from chromosome 5q21. Science. Aug. 9, 1991;253(5020):661-5.
Kinzler et al., Lessons from hereditary colorectal cancer. Cell. Oct. 18, 1996;87(2):159-70.
Knackmuss et al., Specific inhibition of interleukin-13 activity by a recombinant human single-chain immunoglobulin domain directed against the IL-13 receptor alphal chain. Biol Chem. Mar. 2007;388(3):325-30.
Kondo et al., Frizzled 4 gene (FZD4) mutations in patients with familial exudative vitreoretinopathy with variable expressivity. Br J Ophthalmol. Oct. 2003;87(10):1291-5.
Korcsmáros et al., Uniformly curated signaling pathways reveal tissue-specific cross-talks and support drug target discovery. Bioinformatics. Aug. 15, 2010;26(16):2042-50. Epub Jun. 11, 2010.
Korinek et al., Depletion of epithelial stem-cell compartments in the small intestine of mice lacking Tcf-4. Nat Genet. Aug. 1998;19(4):379-83.
Kotha et al., Modification of constrained peptides by ring-closing metathesis reaction. Bioorg Med Chem Lett. Jun. 4, 2001;11(11):1421-3.
Kouzarides, Acetylation: a regulatory modification to rival phosphorylation? EMBO J. Mar. 15, 2000;19(6):1176-9.
Kozlovsky et al., GSK-3 and the neurodevelopmental hypothesis of schizophrenia. Eur Neuropsychopharmacol. Feb. 2002;12(1):13-25.
Kussie et al., Structure of the MDM2 oncoprotein bound to the p53 tumor suppressor transactivation domain. Science. Nov. 8, 1996;274(5289):948-53.
Kutchukian et al., All-atom model for stabilization of alpha-helical structure in peptides by hydrocarbon staples. J Am Chem Soc. Apr. 8, 2009;131(13):4622-7.
Lacombe et al., Reduction of Olefins on Solid Support Using Diimide. Tetranderon Lett. 1998;39:6785-86.
Lammi et al., Mutations in AXIN2 cause familial tooth agenesis and predispose to colorectal cancer. Am J Hum Genet. May 2004;74(5):1043-50. Epub Mar. 23, 2004.
Laporte et al., Molecular and structural basis of cytokine receptor pleiotropy in the interleukin-4/13 system. Cell. Jan. 25, 2008;132(2):259-72.
Le Geuzennec et al., Molecular characterization of Sin3 PAH-domain interactor specificity and identification of PAH partners. Nucleic Acids Res. 2006;34(14):3929-37. Epub Aug. 12, 2006.
Le Geuzennec et al., Molecular determinants of the interaction of Mad with the PAH2 domain of mSin3. J Biol Chem. Jun. 11, 2004;279(24):25823-9. Epub Mar. 26, 2004.
Leduc et al., Helix-stabilized cyclic peptides as selective inhibitors of steroid receptor—coactivator interactions. Proc Natl Acad Sci USA. 2003;100(20):11273-78.
Liang et al., Wnt5a inhibits B cell proliferation and functions as a tumor suppressor in hematopoietic tissue. Cancer Cell. Nov. 2003;4(5):349-60.
Liskamp, Conformationally restricted amino acids and dipeptides, (non)peptidomimetics and secondary structure mimetics. Recl Travl Chim Pays-Bas. 1994;113:1-19.
Little et al., A Mutation in the LDL Receptor-Related Protein 5 Gene Results in the Autosomal Dominant High-Bone-Mass Trait. Am J Hum Genet. 2002;70:11-19.
Liu et al., Chemical Ligation Approach to Form a Peptide Bond between Unprotected Peptide Segments. Concept and Model Study. J Am Chem Soc. 1994;116(10):4149-53.
Liu et al., Targeted degradation of beta-catenin by chimeric F-box fusion proteins. Biochem Biophys Res Commun. Jan. 23, 2004;313(4):1023-9.
Lo et al., Phosphorylation by the beta-catenin/MAPK complex promotes 14-3-3-mediated nuclear export of TCF/POP-1 in signal-responsive cells in *C. elegans*. Cell. Apr. 2, 2004;117(1):95-106.
Logan et al., The Wnt signaling pathway in development and disease. Annu Rev Cell Dev Biol. 2004;20:781-810.
Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.
Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Luo et al., Wnt signaling and human diseases: what are the therapeutic implications? Lab Invest. Feb. 2007;87(2):97-103. Epub Jan. 8, 2007.
Luu et al, Wnt/beta-catenin signaling pathway as a novel cancer drug target. Curr Cancer Drug Targets. Dec. 2004;4(8):653-71.
MacMillan, Evolving strategies for protein synthesis converge on native chemical ligation. Angew Chem Int Ed Engl. Nov. 27, 2006;45(46):7668-72.
Miloux et al., Cloning of the human IL-13R alphal chain and reconstitution with the IL4R alpha of a functional IL-4/1L-13 receptor complex. FEBS Lett. Jan. 20, 1997;401(2-3):163-6.
Miyaoka et al., Increased expression of Wnt-1 in schizophrenic brains. Schizophr Res. Jul. 27, 1997;38(1):1-6.
Moellering et al., Direct inhibition of the NOTCH transcription factor complex. Nature. Nov. 12, 2009;462(7270):182-8. Erratum in: Nature. Jan. 21, 2010;463(7279):384.
Moon et al., WNT and beta-catenin signalling: diseases and therapies. Nat Rev Genet. Sep. 2004;5(9):689-701.
Morin, beta-catenin signaling and cancer. Bioessays. Dec. 1999;21(12):1021-30.
Moy et al., Solution structure of human IL-13 and implication for receptor binding. J Mol Biol. Jun. 29, 2001;310(1):219-30.
Mudher et al., Alzheimer's disease-do tauists and baptists finally shake hands? Trends Neurosci. Jan. 2002;25(1):22-6.
Muir et al., Expressed protein ligation: a general method for protein engineering. Proc Natl Acad Sci U S A. Jun. 9, 1998;95(12):6705-10.
Muir, Semisynthesis of proteins by expressed protein ligation. Annu Rev Biochem. 2003;72:249-89. Epub Feb. 27, 2003.

(56) References Cited

OTHER PUBLICATIONS

Myung et al., The ubiquitin-proteasome pathway and proteasome inhibitors. Med Res Rev. Jul. 2001;21(4):245-73.
Nair et al., X-ray structures of Myc-Max and Mad-Max recognizing DNA. Molecular bases of regulation by proto-oncogenic transcription factors. Cell. Jan. 24, 2003;112(2):193-205.
Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Nishisho et al., Mutations of chromosome 5q21 genes in FAP and colorectal cancer patients. Science. Aug. 9, 1991;253(5020):665-9.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
Pakotiprapha et al., Crystal structure of *Bacillus stearothermophilus* UvrA provides insight into ATP-modulated dimerization, UvrB interaction, and DNA binding. Mol Cell. Jan. 18, 2008;29(1):122-33. Epub Dec. 27, 2007.
Perantoni, Renal development: perspectives on a Wnt-dependent process. Semin Cell Dev Biol. Aug. 2003;14(4):201-8.
Phelan et al., A General Method for Constraining Short Peptides to an α-Helical Conformation. J Am Chem Soc. 1997;119(3):455-60.
Polakis, The oncogenic activation of beta-catenin. Curr Opin Genet Dev. Feb. 1999;9(1):15-21.
Qiu et al., Convenient, Large-Scale Asymmetric Synthesis of Enantiomerically Pure *trans*-Cinnamylglycine and -α-Alanine. Tetrahedron. 2000;56:2577-82.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.
Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roos et al., Synthesis of α-Substituted α-Amino Acids via Cationic Intermediates. J Org Chem. 1993;58:3259-68.
Ross et al., Inhibition of adipogenesis by Wnt signaling. Science. Aug. 11, 2000;289(5481):950-3.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bc1-xL-Bak peptide complex: recognition between regulators of apoptosis. Science. Feb. 14, 1997;275(5302):983-6.
Saxon et al., Cell surface engineering by a modified Staudinger reaction. Science. Mar. 17, 2000;287(5460):2007-10.
Schafmeister et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Shair, A closer view of an oncoprotein-tumor suppressor interaction. Chem Biol. Nov. 1997;4(11):791-4.
Si et al., CCNI/Cyr61 is regulated by the canonical Wnt signal and plays an important role in Wnt3A-induced osteoblast differentiation of mesenchymal stem cells. Mol Cell Biol. Apr. 2006;26(8):2955-64.
Soucek et al., Modelling Myc inhibition as a cancer therapy. Nature. Oct. 2, 2008;455(7213):679-83. Epub Aug. 17, 2008.
Still et al., Semianalytical Treatment of Solvation for Molecular Mechanics and Dynamics. J Am Chem Soc. 1990;112:6127-29.
Su et al., Eradication of pathogenic beta-catenin by Skpl/Cullin/F box ubiquitination machinery. Proc Natl Acad Sci U S A. Oct. 28, 2003;100(22):12729-34. Epub Oct. 16, 2003.
Takeda et al., Human sebaceous tumors harbor inactivating mutations in LEF1. Nat Med. Apr. 2006;12(4):395-7. Epub Mar. 26, 2006.
Thompson et al., Mutants of interleukin 13 with altered reactivity toward interleukin 13 receptors. J Biol Chem. Oct. 15, 1999;274(42):29944-50.
Tian et al., The role of the Wnt-signaling antagonist DKK1 in the development of osteolytic lesions in multiple myeloma. N Engl J Med. Dec. 25, 2003;349(26):2483-94.
Toomes et al., Mutations in LRP5 or FZD4 underlie the common familial exudative vitreoretinopathy locus on chromosome 1 lq. Am J Hum Genet. Apr. 2004;74(4):721-30. Epub Mar. 11, 2004.
Torrance et al., Combinatorial chemoprevention of intestinal neoplasia. Nat Med. Sep. 2000;6(9):1024-8.
Tsuji et al., Antiproliferative activity of REIC/Dkk-3 and its significant down-regulation in non-small-cell lung carcinomas. Biochem Biophys Res Commun. Nov. 23, 20001;289(1):257-63.
Vaickus et al., Immune markers in hematologic malignancies. Crit Rev Oncol Hematol. Dec. 1991;11(4):267-97.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Varallo et al., Beta-catenin expression in Dupuytren's disease: potential role for cell-matrix interactions in modulating beta-catenin levels in vivo and in vitro. Oncogene. Jun. 12, 2003;22(24):3680-4.
Venancio et al., Reconstructing the ubiquitin network: cross-talk with other systems and identification of novel functions. Genome Biol. 2009;10(3):R33. Epub Mar. 30, 2009.
Verdine et al., The challenge of drugging undruggable targets in cancer: lessons learned from targeting BCL-2 family members. Clin Cancer Res. Dec. 15, 2007;13(24):7264-70.
Verma et al., Small interfering RNAs directed against beta-catenin inhibit the in vitro and in vivo growth of colon cancer cells. Clin Cancer Res. Apr. 2003;9(4):1291-300.
Walensky et al., A stapled BID BH3 helix directly binds and activates BAX. Mol Cell. Oct. 20, 2006;24(2):199-210.
Walensky et al., Activation of apoptosis in vivo by a hydrocarbon-stapled BH3 helix. Science. Sep. 3, 2004;305(5689):1466-70.
Walter et al., Critical role for IL-13 in the development of allergen-induced airway hyperreactivity. J Immunol. Oct. 15, 2001;167(8):4668-75.
Wang et al., Inhibition of p53 degradation by Mdm2 acetylation. FEBS Lett. Mar. 12, 2004;561(1-3):195-201.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Williams et al., Asymmetric Synthesis of Monosubstituted and α,α-Disubstituted α-Amino Acids via Diastereoselective Glycine Enolate Alkylations. J Am Chem Soc. 1991;113:9276-86.
Wills-Karp et al., Interleukin-13: central mediator of allergic asthma. Science. Dec. 18, 1998;282(5397):2258-61.

(56) References Cited

OTHER PUBLICATIONS

Wills-Karp, Interleukin-13 in asthma pathogenesis. Immunol Rev. Dec. 2004;202:175-90.
Wills-Karp, The gene encoding interleukin-13: a susceptibility locus for asthma and related traits. Respir Res. 2000;1(1):19-23. Epub Jul. 17, 2000.
Xi et al., Use of DNA and peptide nucleic acid molecular beacons for detection and quantification of rRNA in solution and in whole cells. Appl Environ Microbiol. Sep. 2003;69(9):5673-8.
Xing et al., Crystal structure of a beta-catenin/axin complex suggests a mechanism for the beta- catenin destruction complex. Genes Dev. Nov. 15, 2003;17(22):2753-64. Epub Nov. 4, 2003.
Yang et al., Synthesis and helical structure of lactam bridged BH3 peptides derived from proapoptotic Bcl-2 family proteins. Bioorg Med Chem Lett. 2004;14:1403-06.
Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.
Yu et at, The role of Axin2 in calvarial morphogenesis and craniosynostosis. Development. Apr. 2005;132(8):1995-2005.
Zhou et al., Identification of Ubiquitin Target Proteins Using Cell-Based Arrays. J Proteome Res. 2007;6:4397-4406.
Zhou et al., Lymphoid enhancer factor 1 directs hair follicle patterning and epithelial cell fate. Genes Dev. Mar. 15, 1995;9(6):700-13.
Zhou et al., Tyrosine kinase inhibitor STI-571/Gleevec down-regulates the beta-catenin signaling activity. Cancer Lett. Apr. 25, 2003;193(2):161-70.
Zor et al., Solution structure of the KIX domain of CBP bound to the transactivation domain of c-Myb. J Mol Biol. Mar. 26, 2004;337(3):521-34.
Extended European Search Report for EP 10800148.8 mailed Oct. 16, 2013.
International Preliminary Report on Patentability for PCT/US2012/042738 mailed Jan. 3, 2014.
Invitation to Pay Additional Fees for PCT/US2013/062004 mailed Jan. 2, 2014.
International Search Report and Written Opinion for PCT/US2013/062929 mailed Jan. 30, 2014.
Grossmann et al., Inhibition of oncogenic Wnt signaling through direct targeting of β-catenin. Proc Natl Acad Sci U S A. Oct. 30, 2012;109(44):17942-7. doi: 10.1073/pnas.1208396109. Epub Oct. 15, 2012.
Khalil et al., An efficient and high yield method for the N-tert-butoxycarbonyl protection of sterically hindered amino acids. Tetrahedron Lett. 1996;37(20):3441-44.
Pellois et al., Semisynthetic proteins in mechanistic studies: using chemistry to go where nature can't. Curr Opin Chem Biol. Oct. 2006;10(5):487-91. Epub Aug. 28, 2006.
Schwarzer et al., Protein semisynthesis and expressed protein ligation: chasing a protein's tail. Curr Opin Chem Biol. Dec. 2005;9(6):561-9. Epub Oct. 13, 2005.
Vartak et al., Allosteric Modulation of the Dopamine Receptor by Conformationally Constrained Type VI β-Turn Peptidomimetics of Pro-Leu-Gly-$NH_2$. J Med Chem. 2007;50(26):6725-6729.
Woon et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.
International Search Report and Written Opinion for PCT/US2013/062004, mailed Apr. 23, 2014.
International Search Report and Written Opinion for PCT/US2014/025544, mailed Sep. 10, 2014.
Extended European Search Report for EP 12800679.8, mailed Oct. 2, 2014.
International Search Report and Written Opinion for PCT/US2012/042719, mailed Nov. 1, 2012.
International Preliminary Report on Patentability for PCT/US2012/042719, mailed Jan. 3, 2014.
Artavanis-Tsakonas et al., Notch signaling: cell fate control and signal integration in development. Science. Apr. 30, 1999;284(5415):770-6.
Bray, Notch signalling: a simple pathway becomes complex. Nat Rev Mol Cell Biol. Sep. 2006;7(9):678-89.
Brou et al., A novel proteolytic cleavage involved in Notch signaling: the role of the disintegrin-metalloprotease TACE. Mol Cell. Feb. 2000;5(2):207-16.
Colaluca et al., NUMB controls p53 tumour suppressor activity. Nature. Jan. 3, 2008;451(7174):76-80. doi: 10.1038/nature06412.
Darnell, Transcription factors as targets for cancer therapy. Nat Rev Cancer. Oct. 2002;2(10):740-9.
Del Bianco et al., Mutational and energetic studies of Notch 1 transcription complexes. J Mol Biol. Feb. 8, 2008;376(1):131-40. Epub Nov. 28, 2007.
Dombroski et al., Isolation of an active human transposable element. Science. Dec. 20, 1991;254(5039):1805-8.
Guo et al., Probing the alpha-helical structural stability of stapled p53 peptides: molecular dynamics simulations and analysis. Chem Biol Drug Des. Apr. 2010;75(4):348-59. doi: 10.1111/j.1747-0285.2010.00951.x.
Karle et al., Structural characteristics of alpha-helical peptide molecules containing Aib residues. Biochemistry. Jul. 24, 1990;29(29):6747-56.
Kim et al., Introduction of all-hydrocarbon i,i+3 staples into alpha-helices via ring-closing olefin metathesis. Org Lett. Jul. 2, 2010;12(13):3046-9. doi: 10.1021/o11010449.
Kovall et al., Crystal structure of the nuclear effector of Notch signaling, CSL, bound to DNA. EMBO J. Sep. 1, 2004;23(17):3441-51. Epub Aug. 5, 2004.
Miller et al., Application of Ring-Closing Metathesis to the Synthesis of Rigidified Amino Acids and Peptides. J Am Chem Soc. 1996;118(40):9606-9614.
Miller et al., Synthesis of Conformationally Restricted Amino Acids and Peptides Employing Olefin Metathesis. J Am Chem Soc. 1995;117(21):5855-5856.
Moellering et al., Computational modeling and molecular optimization of stabilized alpha-helical peptides targeting NOTCH-CSL transcriptional complexes. European Journal of Cancer Supplements Nov. 2010; 8(7):30. DOI: 10.1016/S1359-6349(10)71774-2. Abstract 69.
Nam et al., Structural basis for cooperativity in recruitment of MAML coactivators to Notch transcription complexes. Cell. Mar. 10, 2006;124(5):973-83.
Nam et al., Structural requirements for assembly of the CSL.intracellular Notchl.Mastermind-like 1 transcriptional activation complex. J Biol Chem. Jun. 6, 2003;278(23):21232-9. Epub Mar. 18, 2003.
Robert, A hierarchical "nesting" approach to describe the stability of alpha helices with side-chain interactions. Biopolymers. 1990;30(3-4):335-47.
Sali et al., Stabilization of protein structure by interaction of alpha-helix dipole with a charged side chain. Nature. Oct. 20, 1988;335(6192):740-3.
Toniolo, Conformationally restricted peptides through short-range cyclizations. Int J Pept Protein Res. Apr. 1990;35(4):287-300.
Verdine et al., Stapled peptides for intracellular drug targets. Methods Enzymol. 2012;503:3-33. doi: 10.1016/B978-0-12-396962-0.00001-X.
Williams et al., Asymmetric synthesis of 2,6-diamino-6-(hydroxymethyl)pimelic acid: assignment of stereochemistry. J Am Chem Soc. 1991;113(18):6976-6981.
Wilson et al., Crystal structure of the CSL-Notch-Mastermind ternary complex bound to DNA. Cell. Mar. 10, 2006;124(5):985-96.
Wu et al., MAML1, a human homologue of Drosophila mastermind, is a transcriptional co-activator for NOTCH receptors. Nat Genet. Dec. 2000;26(4):484-9.
Zhang et al., A cell-penetrating helical peptide as a potential HIV-1 inhibitor. J Mol Biol. May 2, 2008;378(3):565-80. doi: 10.1016/j.jmb.2008.02.066. Epub Mar. 6, 2008.

* cited by examiner

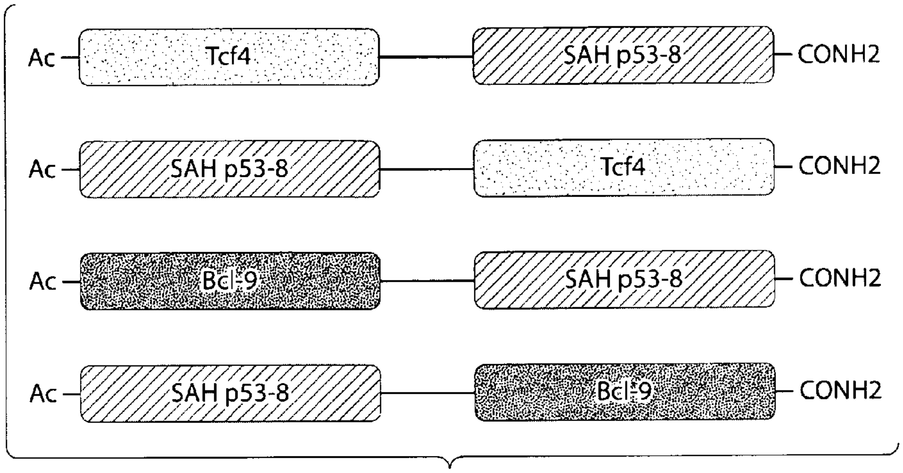

Fig. 7

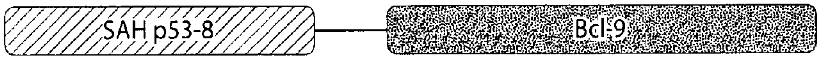

QSQQTF$\mathbf{R}_8$NLWRLL$\mathbf{S}_5$QN-(Ahx)$_n$-SQEQL$\mathbf{R}_8$HRERSL$\mathbf{S}_5$TLRDIQRMLF (SEQ ID NO:1)
QSQQTF$\mathbf{R}_8$NLWRLL$\mathbf{S}_5$QN-(Ahx)$_n$-SQEQLEHRERSL$\mathbf{S}_5$TLR$\mathbf{S}_5$IQRMLF (SEQ ID NO:2)
QSQQTF$\mathbf{R}_8$NLWRLL$\mathbf{S}_5$QN-(Ahx)$_n$-SQEQLEHR$\mathbf{S}_5$RSL$\mathbf{S}_5$TLRDIQRMLF (SEQ ID NO:3)

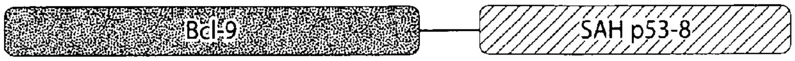

SQEQL$\mathbf{R}_8$HRERSL$\mathbf{S}_5$TLRDIQRMLF-(Ahx)$_n$-QSQQTF$\mathbf{R}_8$NLWRLL$\mathbf{S}_5$QN (SEQ ID NO:4)
SQEQLEHRERSL$\mathbf{S}_5$TLR$\mathbf{S}_5$IQRMLF-(Ahx)$_n$-QSQQTF$\mathbf{R}_8$NLWRLL$\mathbf{S}_5$QN (SEQ ID NO:5)
SQEQLEHR$\mathbf{S}_5$RSL$\mathbf{S}_5$TLRDIQRMLF-(Ahx)$_n$-QSQQTF$\mathbf{R}_8$NLWRLL$\mathbf{S}_5$QN (SEQ ID NO:6)

n=2-4

Ahx: 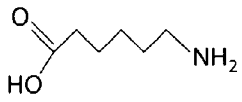

Fig. 8

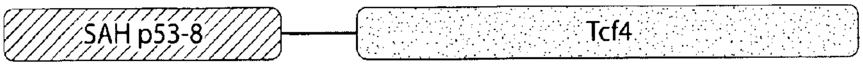

QSQQTF$\mathbf{R}_8$NLWRLL$\mathbf{S}_5$QN-(PEG)$_n$-DELISFKDEGEQE(βAla)$_2$ERDL$\mathbf{S}_5$DVK$\mathbf{S}_5$SLVN (SEQ ID NO:17)
QSQQTF$\mathbf{R}_8$NLWRLL$\mathbf{S}_5$QN-(PEG)$_n$-DELISFKDEGEQE(βAla)$_2$E$\mathbf{R}_8$DLADVK$\mathbf{S}_5$SLVN (SEQ ID NO:18)

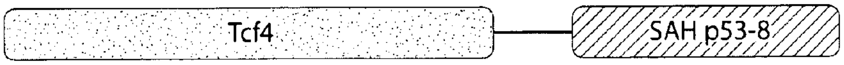

DELISFKDEGEQE(βAla)$_2$ERDL$\mathbf{S}_5$DVK$\mathbf{S}_5$SLVN-(PEG)$_n$-QSQQTF$\mathbf{R}_8$NLWRLL$\mathbf{S}_5$QN (SEQ ID NO:19)
DELISFKDEGEQE(βAla)$_2$E$\mathbf{R}_8$DLADVK$\mathbf{S}_5$SLVN-(PEG)$_n$-QSQQTF$\mathbf{R}_8$NLWRLL$\mathbf{S}_5$QN (SEQ ID NO:20)

n=2-4

βAla: 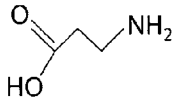

Fig. 11

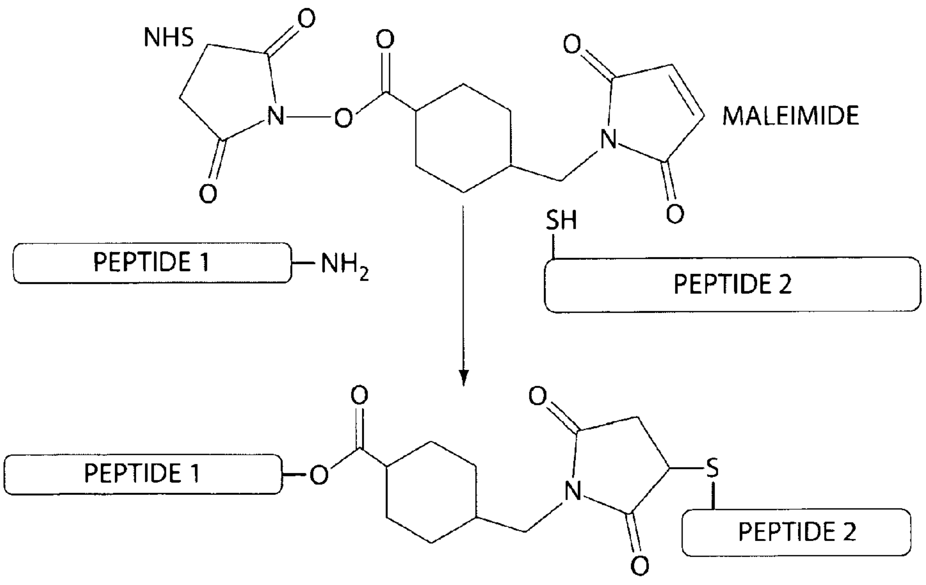

Fig. 12

SM(PEG)$_n$
NHS-PEG$_n$-MALEIMIDE
SUCCINIMIDYL-([N-MALEIMIDOPROPIONAMIDO]-#ETHYLENEGLYCOL) ESTER
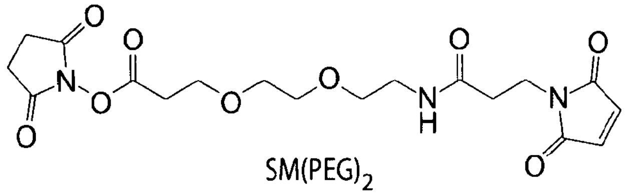
SM(PEG)$_2$
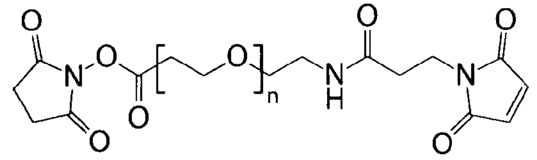
n = 2, 4, 6, 8, 12, 24
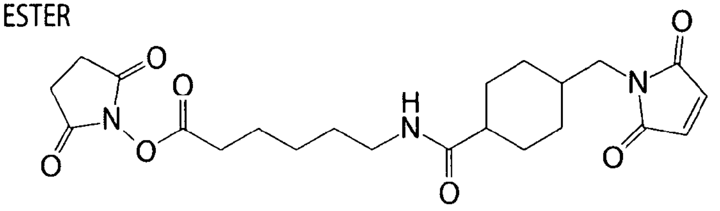
LC-SMCC
M.W. 447.48
SPACER ARM 16.2 A
Fig. 13

| Peptide | Sequence |
|---|---|
| SID long (5-28) | VRMNIQMLLEAADYLERREREAEH (SEQ ID NO:85) |
| SID short (5-24) | VRMNIQMLLEAADYLERRER (SEQ ID NO:86) |
| consens | XXXΦZZΦΦXAAXXΦEX |
| SID1 | βAla-ERLRRRI*MLL*AANYLER (SEQ ID NO:87) |
| SID2 | βAla-VRRRI*MLL*AANYLER (SEQ ID NO:88) |
| SID3 | βAla-VRRRIQRLL*AAN*LER (SEQ ID NO:89) |
| SID4 | βAla-VRMNIQMLLQAANR*ERR*R (SEQ ID NO:90) |
| SID5 | βAla-VRRRIQMLLEAANK*ERR*R (SEQ ID NO:91) |
| SID6 | βAla-VRMNIQMLLQAANRLERR*REA*H (SEQ ID NO:92) |
| SID7 | βAla-VRRRIQMLLEAANKLERR*REA*H (SEQ ID NO:93) |
| SID8 | βAla-VRMNIQMLL*AAN*LER (SEQ ID NO:94) |
| SID9 | βAla-VRMNI*MLL*AANYLER (SEQ ID NO:95) |

Fig. 25A

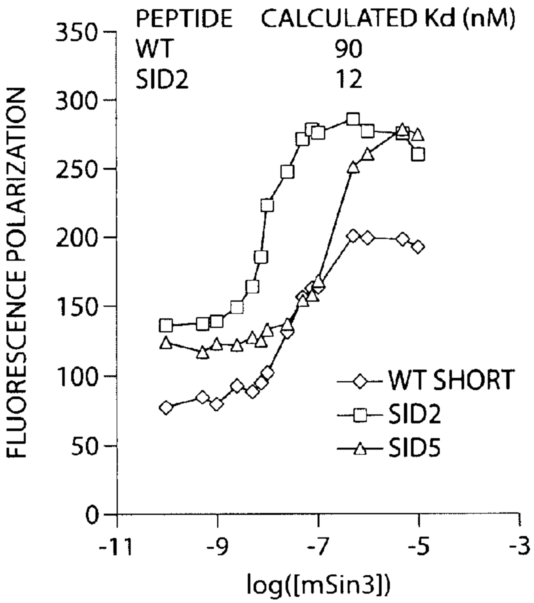

Fig. 25B

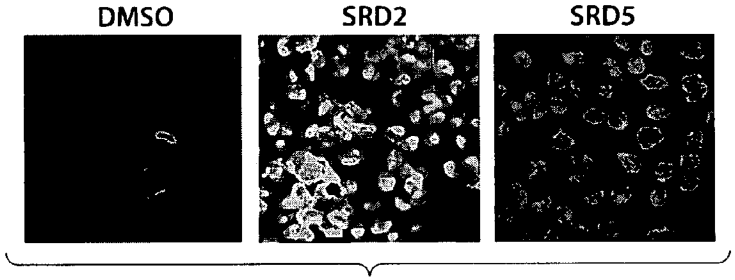

Fig. 25C

| COMPOUND | SEQUENCE | $K_D$ (nM) | Cell Perm | |
|---|---|---|---|---|
| MLL WT | I L P S D I M D F V L K N T | 89 | Low | (SEQ ID NO:99) |
| MLL1-1 | I L P * D I M * F V L K N T | 55 | Low | (SEQ ID NO:81) |
| MLL1-2 | I L P * R I M * F V L K N T | 63 | High | (SEQ ID NO:82) |
| MLL2-1 | I L P S D I M * F V L * N T | NT | Low | (SEQ ID NO:83) |
| MLL2-2 | I L P S R I M * F V L * N T | NT | High | (SEQ ID NO:84) |
| MLLneg1 | I L P * R I M * F V A K N T | NT | NT | (SEQ ID NO:96) |
| MLLneg2 | I L P * R I M * F A L K N T | NT | NT | (SEQ ID NO:97) |
| MLLneg3 | I A P * R I M * F V L K N T | NT | NT | (SEQ ID NO:98) |
| cMYB WT | K E K R I K E L E L L L M S T E N E L K G | NT | Low | (SEQ ID NO:50) |
| cMyb1-1 | K * K R I * E L E L L L M S T E N E L K G | 534 | Low | (SEQ ID NO:73) |
| cMyb1-2 | K * K R I * R L E L L L M S T E N E L K G | 474 | Low | (SEQ ID NO:74) |
| cMyb2-1 | K E * R I K * L E L L L M S T E N E L K G | 213 | Low | (SEQ ID NO:75) |
| cMyb2-2 | K R * R I K * L E L L L M S T E N E L K G | 564 | Low | (SEQ ID NO:76) |
| cMyb3-1 | K E * R I K E L E * L L M S T E N E L K G | 439 | Low | (SEQ ID NO:77) |
| cMyb3-2 | K E * R I K R L E * L L M S T E N E L K G | 332 | Low | (SEQ ID NO:78) |
| cMyb3-3 | K R * R I K E L E * L L M S T E N E L K G | 340 | Low | (SEQ ID NO:79) |
| cMyb4-1 | K E K R I K E L E L L L M S T E * E L K * | 370 | Low | (SEQ ID NO:80) |

Fig. 26A

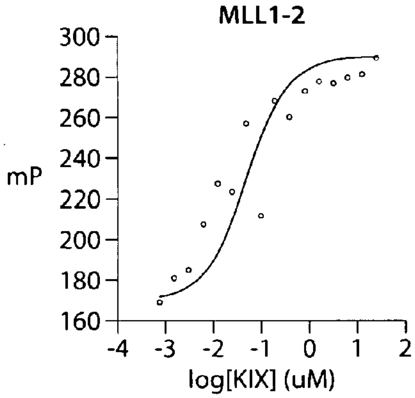

Fig. 26B

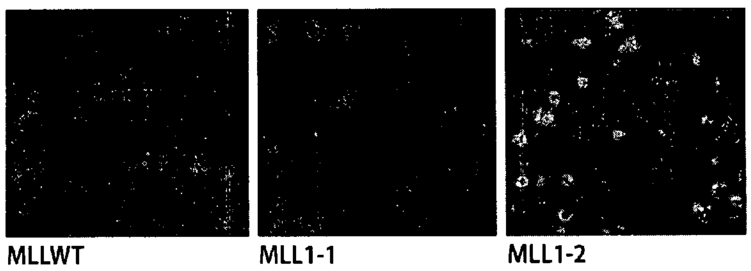

Fig. 26C

BIFUNCTIONAL STAPLED POLYPEPTIDES AND USES THEREOF

RELATED APPLICATIONS

The present application is a national stage filing under 35 U.S.C. §371 of international PCT application, PCT/US2010/001952, filed Jul. 13, 2010, which claims priority under 35 U.S.C. §119(e) to U.S. provisional patent application, U.S. Ser. No. 61/225,191, filed Jul. 13, 2009, each of which is incorporated herein by reference.

BACKGROUND OF THE INVENTION

The important biological roles that peptides and proteins play as hormones, enzyme inhibitors, substrates, and neurotransmitters has led to the use of peptides and/or peptide mimetics as therapeutic agents. The peptide's bioactive conformation, combining structural elements such as alpha-helices, beta-sheets, turns, and/or loops, is important as it allows for selective biological recognition of receptors, enzymes, and nucleic acids, thereby influencing cell-cell communication and/or controlling vital cellular functions, such as metabolism, immune defense, and cell division (Babine et al., *Chem. Rev.* (1997) 97:1359). Unfortunately, the utility of peptides as drugs is severely limited by several factors, including their rapid degradation by proteases under physiological conditions, their poor cell permeability, and their lack of binding specificity resulting from conformational flexibility.

The alpha-helix is one of the major structural components of peptides. However, alpha-helical peptides have a propensity for unraveling and forming random coils, which are, in most cases, biologically less active, or even inactive, and are highly susceptible to proteolytic degradation.

Many research groups have developed strategies for the design and synthesis of more robust peptides as therapeutics. For example, one strategy has been to incorporate more robust functionalities into the peptide chain while still maintaining the peptide's unique conformation and secondary structure (see, for example, Gante, *Angew. Chem. Int. Ed. Engl.* (1994) 33:1699-1720; Liskamp, *Red. Trav. Chim. Pays-Bas* (1994) 113:1; Giannis, *Angew. Chem. Int. Ed. Engl.* (1993) 32:1244; Bailey, *Peptide Chemistry*, Wiley, New York (1990), 182; and references cited therein). Another approach has been to stabilize the peptide via covalent cross-links (see, for example, Phelan et al., *J. Am. Chem. Soc.* (1997) 119:455; Leuc et al., *Proc. Natl. Acad. Sci. USA* (2003) 100: 11273; Bracken et al., *J. Am. Chem. Soc.* (1994) 116:6432; Yan et al., *Bioorg. Med. Chem.* (2004) 14:1403). However, the majority of reported approaches involved the use of polar and/or labile cross-linking groups.

"Peptide stapling" is a term coined for a synthetic methodology used to covalently join two olefin-containing side chains present in a polypeptide chain using an olefin metathesis reaction (*J. Org. Chem.* (2001) 66(16); Blackwell et al., *Angew. Chem. Int. Ed.* (1994) 37:3281). Stapling of a peptide using a hydrocarbon cross-linker created from an olefin metathesis reaction has bee shown to help maintain a peptide's native conformation, particularly under physiological conditions (U.S. Pat. No. 7,192,713; Schafineister et al., *J. Am. Chem. Soc.* (2000) 122:5891-5892; Walensky et al., *Science* (2004) 305:1466-1470; each of which is incorporated herein by reference). This strategy has been applied to the apoptosis-inducing BID-BH3 alpha-helix, resulting in a higher suppression of malignant growth of leukemia in an animal model compared to the unstapled peptide (Walensky et al., *Science* (2004) 305:1466-1470; U.S. Patent Application Publication No. 2005/02506890; U.S. Patent Application Publication No. 2006/0008848; each of which is incorporated herein by reference).

SUMMARY OF THE INVENTION

The present invention stems from the recognition of a new use for stapled or stitched peptides. Given the stability of such peptides, they may be used as agents for recruiting proteins or other biomolecules to a particular protein, nucleic acid, other biomolecule, cell, or organelle (i.e., tethering two cellular components together or brining them into close proximity). In particular, the present invention provides bifunctional peptides, one or both domains of which may be stapled or stitched. One domain of the bifunctional peptide acts as a targeting moiety that binds to a target; the other domain acts as an effector domain to recruit a protein or protein complex to the target. The effector domain typically acts on or modifies the activity of the target. In essence, the bifunctional peptide works to bring two proteins or other biomolecules in close proximity to one another. The targeting domain, the effector domain, or both domains may be stapled or stitched to stabilize the conformation of the peptide. The two domains are linked together via a linker, which may range in structure from simply a covalent bond to a bifunctional molecule to a polymeric linker.

In one aspect, the present invention provides a bifunctional peptide wherein one or both of the targeting domain and effector domain are stapled or stitched. The inventive bifunctional peptide includes a targeting domain associated with an effector domain. Each peptide comprises 5-100 amino acids as needed to act as a ligand for a targeted protein. The peptide may include unnatural amino acids with olefin side chains as necessary to form a staple or stitch used to stabilize the conformation of the peptide. In certain embodiments, the stapled or stitched peptide is a helical peptide. Typically, the two domains are covalently associated with one another through a linker; however, non-covalent associations may also be used. In certain embodiments, the bifunctional peptide is a stapled version of SAH p53-8 associated with a stapled version of Bcl-9. In other embodiments, the bifunctional peptide is a stapled version of SAH p53-8 associated with Tcf4. Such inventive bifunctional peptides promote the degradation of β-catenin by recruiting E3 ubiquitin ligase to β-catenin. E3 ubiquitin ligase then catalyzes the ubiquitination of β-catenin, resulting in its degradation by the proteasome.

In certain embodiments, an inventive bifunctional stapled or stitched peptide comprising a targeting domain, a linker, and an effector domain are the focus of the present invention. The present invention provides bifunctional stapled or stitched peptides, and methods for their preparation and use. The present invention also provides pharmaceutical compositions comprising an inventive bifunctional stapled or stitched peptide and a pharmaceutically acceptable excipient. In certain embodiments, the present invention provides bifunctional, alpha-helical stapled or stitched peptides, wherein at least one of the peptides is alpha-helical and stabilized by stapling or stitching. In certain embodiments, the inventive alpha-helical peptide retains its alpha-helical structure under physiological conditions, such as in the body of a subject (e.g., in the gastrointestinal tract; in the bloodstream).

In certain embodiments, stapled or stitched bifunctional peptides comprising a targeting domain, a linker, and an effector domain are generally arranged as follows:

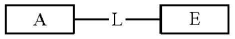

wherein A and E are peptides or peptide-like; A and/or E is a stapled or stitched peptide; and L is a linker (e.g., covalent bond; polyethylene glycol (PEG); aminohexanoic acid-based linker; poly-glycine peptide, monodispers polymer etc.), and wherein if A is a targeting domain and E is an effector domain.

In one aspect, the present invention provides a bifunctional stapled or stitched peptide wherein one or both domains (i.e., A or E) are of the formula:

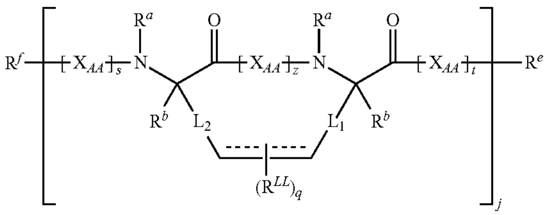

wherein $L_1$, $L_2$, $R^a$, $R^b$, $R^e$, $R^f$, $R^{LL}$, $X_{AA}$, s, t, q, z, j, and ---------- are as described herein.

In another aspect, the present invention provides a bifunctional stitched peptide wherein one or both domains are of the formula (i.e., a peptide with multiple staples):

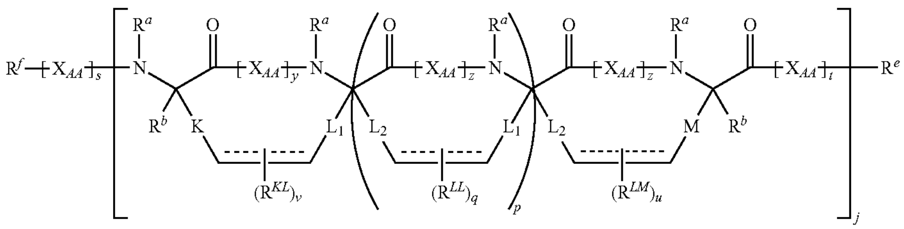

wherein K, $L_1$, $L_2$, M, $R^a$, $R^b$, $R^e$, $R^f$, $R^{KL}$, $R^{LL}$, $R^{LM}$, $X_{AA}$, y, z, j, p, s, t, u, v, q, and ---------- are as described herein.

The amino acid sequence of one or both of the domains may be substantially similar to or homologous to a known peptide. In some embodiments, the targeting domain binds a protein, nucleic acid, or other biomolecule. In certain embodiments, the targeting domain binds β-catenin, c-Myc, Ras, or hypoxia-inducible factor. In some embodiments, the effector domain recruits an enzyme to a target molecule. In certain embodiments, the effector domain is a ligand for a ubiquitinating enzyme (e.g., E3 ubiquitin ligase), a glycosylating enzyme, a histone deacetylase, a histone acyl transferase, a kinase, a protease, a farnesyl transferase, an acetylase, or a phosphatase.

The linker may be proteinogenic or non-proteinogenic. The linker may be as simple as a covalent bond (e.g., a carbon-carbon bond, disulfide bond, carbon-heteroatom bond, etc.), or it may be more complicated such as a polymeric linker (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In other embodiments, the linker comprises a polyethylene glycol moiety (PEG). In other embodiments, the linker comprises amino acids. The linker may included functionalized moieties to facilitate attachment of a nucleophile (e.g., thiol, amino) from the peptide to the linker. In certain embodiments, the linker includes a maleimide group. In certain embodiments, the linker includes a NHS ester. In certain embodiments, the linker includes both a NHS ester and a maleimide group.

To give but one example where a stapled bifunctional peptide may be useful in treating or studying a disease or other biological process, consider the loss of endogenous β-catenin degradation in human cancers. To restore β-catenin degradation, an inventive bifunctional stapled peptide is used. The bifunctional peptide includes a stapled β-catenin ligand (e.g., Bcl-9 or Tcf4) associated with an E3 ubiquitin ligase ligand (SAH p53-8); thereby recruiting ubiquitination machinery to the β-catenin to be degraded. The β-catenin is ubiquitinated by ubiquitin ligase leading to its destruction in the proteasome. As will be appreciated by those of skill in this art, proteins other than β-catenin may be targeted for ubiquitination using this approach, and/or other cellular machinery or enzymes may be recruited to the target besides ubiquitination machinery. For example, enzymes or enzyme complexes such as kinases, phosphatases, proteases, glycosylases, ligases, acetylases, lipidases, etc. may be recruited to a targeted protein. Almost any post-translational modification including degradation of a protein may be promoted using the inventive bifunctional peptide. Such inventive bifunctional peptides may be used in pharmaceutical compositions to treat disease in a subject (e.g., human).

The invention also provides a system for designing and preparing bifunctional peptides. One or both domains of the bifunctional peptide may be already known in the art. The peptide domain may then be modified to increase its affinity for the targeted protein. The peptide may also be modified to include the unnatural amino acids needed to staple or stitch the peptide. In certain embodiments, a library of peptides with various mutations may be screened to identify a peptide with a high affinity for the target protein. The library may include stapled or unstapled, stitched or unstitched peptides. In certain embodiments, a peptide domain may be designed in silico using structural information of the target protein or of a known protein-protein interaction. In designing the peptide domain it may need to be determined where the one or more staples are to be placed and/or substitution in the primary sequence to yield a better bifunctional peptide. The designed peptide(s) may be assayed for the desired activity using techniques known in the art for assessing binding affinity, functionality, stability, pharmacokinetics, etc. Once the bifunctional peptide is designed it can be prepared using available peptide chemistry. For example, a peptide may be synthesized using standard solid phase peptide synthesis methodology. Unnatural amino acids (e.g., $S_5$, $R_5$, $S_8$, $R_8$) as needed or desired may be introduced into the primary sequence. The peptide once synthesized is associated with the other peptide, or the entire bifunctional peptide may be created at once. The peptide may be stapled, stitched, deprotected, or otherwise modified before or after it is associated with the other peptide domain.

The inventive bifunctional peptides may be used as therapeutics as well as research tools. In certain embodiments, the inventive bifunctional peptide is used in the treatment of a disease in a subject (e.g., a proliferative disease, a neurodegenerative disease). For example, the Tcf4-SAH p53 peptide or the Bcl-9-SAH p53 peptide as described herein (see FIGS. 8-11; SEQ ID NO: 1-20) may be used to treat cancer in a subject. As will be appreciated by one of skill in the art, almost any disease, disorder, or condition may be treated using the inventive bifunctional peptide. The effector and targeting domains of the bifunctional peptide may be tailored for the specific use. The inventive bifunctional peptides may also be used as research tools. For example, the bifunctional peptide may be used to probe the function of a particular protein in a cell. Increasing the degradation will allow a researcher to understand how a deficit of the protein affects a pathway or cell. Promoting the phosphorylation or other secondary modification will allow a researcher to understand how the state of a protein affects its role in a biological pathway or cell.

In another aspect, the invention provides a kit with the components necessary for designing and preparing an inventive bifunctional peptide. The kit may include containers, enzymes, buffers, amino acids, reagents, catalysts, software, instructions, etc. needed to make and/or use an inventive bifunctional peptide.

DEFINITIONS

Definitions of specific functional groups and chemical terms are described in more detail below. For purposes of this invention, the chemical elements are identified in accordance with the Periodic Table of the Elements, CAS version, *Handbook of Chemistry and Physics, 75th* Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry, 5th* Edition, John Wiley & Sons, Inc., New York, 2001; Larock, *Comprehensive Organic Transformations*, VCH Publishers, Inc., New York, 1989; Carruthers, *Some Modern Methods of Organic Synthesis, 3rd* Edition, Cambridge University Press, Cambridge, 1987.

"Stapling," "hydrocarbon-stapling" as used herein introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an alpha helix structure. The length and geometry of the cross-linker can be optimized to improve the yield of the desired secondary structure content. The constraint provided can, for example, prevent the secondary structure to unfold and/or can reinforce the shape of the secondary structure. A secondary structure that is prevented from unfolding is, for example, more stable.

A "stapled" peptide is a peptide comprising a selected number of standard or non-standard amino acids, further comprising at least two moieties capable of undergoing reaction to promote carbon-carbon bond formation, that has been contacted with a reagent to generate at least one cross-linker between the at least two moieties, which modulates, for example, peptide stability.

A "stitched" peptide, as used herein, is a stapled peptide comprising more than one, that is multiple (two, three, four, five, six, etc.) cross-linked moieties.

The compounds, proteins, or peptides of the present invention (e.g., amino acids, and unstapled, partially stapled, and stapled peptides and proteins, and unstitched, partially stitched, and stitched peptides and proteins) may exist in particular geometric or stereoisomeric forms. The present invention contemplates all such compounds, including cis- and trans-isomers, R- and S-enantiomers, diastereomers, (D)- and (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substituent. Thus, for example, acyl is acylene; alkyl is alkylene; alkeneyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula $—C(=O)R^A$, $—C(=O)OR^A$, $—C(=O)—O—C(=O)R^A$, $—C(=O)SR^A$, $—C(=O)N(R^A)_2$, $—C(=S)R^A$, $—C(=S)N(R^A)_2$, and $—C(=S)S(R^A)$, $—C(=NR^A)R^A$, $—C(=NR^A)OR^A$, $—C(=NR^A)SR^A$, and $—C(=NR^A)N(R^A)_2$, wherein $R^A$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes ($—CHO$), carboxylic acids ($—CO_2H$), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula ($—OR^i$), wherein $R^i$ is an optionally substituted acyl group, as defined herein, and the oxygen moiety is directly attached to the parent molecule.

The term "acylene," as used herein, refers to an acyl group having the general formulae: $—R^0—(C=X^1)—R^0—$, $—R^0—X^2(C=X^1)—R^0—$, or $—R^0—X^2(C=X^1)X^3—R^0—$, where $X^1$, $X^2$, and $X^3$ is, independently, oxygen, sulfur, or $NR^r$, wherein $R^r$ is hydrogen or aliphatic, and $R^0$ is an optionally substituted alkylene, alkenylene, alkynylene, heteroalkylene, heteroalkenylene, or heteroalkynylene group, as defined herein. Exemplary acylene groups wherein $R^0$ is alkylene includes $—(CH_2)_T—O(C=O)—(CH_2)_T—$; $—(CH_2)_T—NR^r(C=O)—(CH_2)_T—$; $—(CH_2)_T—O(C=NR^r)—(CH_2)_T—$; $—(CH_2)_T—NR^r(C=NR^r)—(CH_2)_T—$; $—(CH_2)_T—(C=O)—(CH_2)_T—$; $—(CH_2)_T—(C=NR^r)—(CH_2)_T—$, $—(CH_2)_T—S(C=S)—(CH_2)_T—$; $—(CH_2)_T—NR^r(C=S)—(CH_2)_T—$; $—(CH_2)_T—S(C=NR^r)—(CH_2)_T—$; $—(CH_2)_T—O(C=S)—(CH_2)_T—$; $—(CH_2)_T—(C=S)—(CH_2)_T—$; or $—(CH_2)_T—S(C=O)—(CH_2)_T—$, and the like, which may bear one or more substituents; and wherein each instance of xx is, independently, an integer between 0 to 20. Acylene groups may be cyclic or acyclic, branched or unbranched, substituted or unsubstituted. Acylene substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “alkylene,” as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “alkenyl,” as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “alkenylene,” as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “alkynyl,” as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “alkynylene,” as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term “amino,” as used herein, refers to a group of the formula ($—NH_2$). A “substituted amino” refers either to a mono-substituted amine ($—NHR^h$) of a disubstituted amine ($—NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the disubstituted amino group ($—NR^h_2$) form a 5- to 6-membered heterocyclic ring.

The term “alkoxy” refers to a “substituted hydroxyl” of the formula ($—OR^i$), wherein $R^i$ is an optionally substituted alkyl group, as defined herein, and the oxygen moiety is directly attached to the parent molecule.

The term "alkylthioxy" refers to a "substituted thiol" of the formula (—$SR^r$), wherein $R^r$ is an optionally substituted alkyl group, as defined herein, and the sulfur moiety is directly attached to the parent molecule.

The term "alkylamino" refers to a "substituted amino" of the formula (—$NR^h{}_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Additionally, arylene groups may be incorporated as a linker group into an alkylene, alkenylene, alkynylene, heteroalkylene, heteroalkenylene, or heteroalkynylene group, as defined herein.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino" refers to a "substituted amino" of the formula (—$NR^h{}_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—$N_3$).

The term "cyano," as used herein, refers to a group of the formula (—CN).

The terms "halo" and "halogen," as used herein, refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heteroalkylamino" refers to a "substituted amino" of the formula (—$NR^h_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—$OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula (—$SR^r$), wherein $R^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the (—$NR^h_2$), wherein $R^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula (—$OR^i$), wherein $R^i$ is an optionally substituted heteroaryl group, as defined herein, and the oxygen moiety is directly attached to the parent molecule.

The term "heteroarylthioxy" refers to a "substituted thiol" of the formula (—$SR^r$), wherein $R^r$ is an optionally substituted heteroaryl group, as defined herein, and the sulfur moiety is directly attached to the parent molecule.

The term "hydroxy," or "hydroxyl," as used herein, refers to a group of the formula (—OH). A "substituted hydroxyl" refers to a group of the formula (—$OR^i$), wherein $R^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula (═$NR^r$), wherein $R^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "isocyano," as used herein, refers to a group of the formula (—NC).

The term "nitro," as used herein, refers to a group of the formula (—$NO_2$).

The term "oxo," as used herein, refers to a group of the formula (═O).

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis,* 2nd edition, Pierce Chemical Company, Rockford, 1984, the entire contents of each of which are hereby incorporated herein by reference. Exemplary resins which may be employed by the present invention include, but are not limited to:

(1) alkenyl resins (e.g., REM resin, vinyl sulfone polymer-bound resin, vinyl-polystyrene resin);

(2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2-Chlorotrityl Knorr resin, 2-N-Fmoc-Amino-dibenzocyclohepta-1,4-diene, polymer-bound resin, 4-[4-(1-Fmoc-aminoethyl)-2-methoxy-5-nitrophenoxy] butyramidomethyl-polystyrene resin, 4-Benzyloxybenzylamine, polymer-bound, 4-Carboxybenzenesulfonamide, polymer-bound, Bis(tert-butoxycarbonyl) thiopseudourea, polymer-bound, Dimethylaminomethyl-polystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound);

(3) benzhydrylamine (BHA) resins (e.g., 2-Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound);

(4) Br-functionalized resins (e.g., 4-(Benzyloxy)benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S-Br, TentaGel S-Br);

(5) Chloromethyl resins (e.g., 5-[4-(Chloromethyl)phenyl] pentyl]styrene, polymer-bound, 4-(Benzyloxy)benzyl chloride polymer bound, 4-Methoxybenzhydryl chloride, polymer-bound);

(6) CHO-functionalized resins (e.g., (4-Formyl-3-methoxyphenoxymethyl)polystyrene, (4-Formyl-3-methoxyphenoxymethyl)polystyrene, 3-Benzyloxybenzaldehyde, polymer-bound, 4-Benzyloxy-2,6-dimethoxybenzaldehyde, polymer-bound, Formylpolystyrene, HypoGel® 200 CHO, Indole resin, Polystyrene A-$CH(OEt)_2$, TentaGel HL-$CH(OEt)_2$);

(7) Cl functionalized resins (e.g., Benzoyl chloride polymer bound, (chloromethyl)polystyrene, Merrifield's resin);

(8) $CO_2H$ functionalized resins (e.g., Carboxyethylpolystryrene, HypoGel® 200 COOH, Polystyrene AM-COOH, TentaGel HL-COOH, TentaGel MB-COOH, TentaGel S—COOH);

(9) Hypo-Gel resins (e.g., HypoGel® 200 FMP, HypoGel® 200 PHB, HypoGel® 200 Trt-OH, HypoGel® 200 HMB);

(10) I-functionalized resins (e.g., 4-Iodophenol, polymer-bound, Iodopolystyrene); Janda-Jels™ (JandaJel$^{ä}$-Rink amide, JandaJel-$NH_2$, JandaJel-Cl, JandaJel-4-Mercaptophenol, JandaJel-OH, JandaJel-1-(3-Dimethylaminopropyl)-3-ethylcarbodiimide, JandaJel-1,3,4,6,7,8-hexahydro-2H-pyrimido-[1,2-a]pyrimidine, JandaJel-morpholine, JandaJel-polypyridine, JandaJel-Triphenylphosphine, JandaJel-Wang);

(11) MBHA resins (3[4'-(Hydroxymethyl)phenoxy]propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine));

(12) $NH_2$ functionalized resins ((Aminomethyl)polystyrene, (Aminomethyl)polystyrene, HypoGel® 200 NH2, Polystyrene AM-$NH_2$, Polystyrene Microspheres 2-aminoethylated, Polystyrol Microspheres 2-bromoethylated, Polystyrol Microspheres 2-hydroxyethylated, TentaGel HL-$NH_2$, Tentagel M Br, Tentagel M $NH_2$, Tentagel M OH, TentaGel MB-$NH_2$, TentaGel S—$NH_2$, TentaGel S—$NH_2$);

(13) OH-functionalized resins (e.g., 4-hydroxymethylbenzoic acid, polymer-bound, Hydroxymethyl Resins, OH-functionalized Wang Resins);

(14) oxime resins (e.g., 4-Chlorobenzophenone oxime polymer bound, Benzophenone oxime polymer bound, 4-Methoxybenzophenone oxime polymer bound);

(15) PEG resins (e.g., ethylene glycol polymer bound);

(16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys{Boc-Lys(Boc)-Lys[Boc-Lys(Boc)]}-b-Ala-O-PAM resin, Boc-Lys(Fmoc)-Lys[Boc-Lys(Fmoc)]-Lys{Boc-Lys(Fmoc)-Lys[Boc-Lys(Fmoc)]}-b-Ala-O-PAM resin, Boc-Lys(Boc)-Lys[Boc-Lys(Boc)]-Lys{Boc-Lys(Boc)-Lys[Boc-Lys(Boc)]}-Cys(Acm)-b-Ala-O-PAM resin, Preloaded PAM resins);

(17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys{Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols);

(19) thiol-functionalized resins (e.g., HypoGel® 200 S-Trt, Polystyrene AM-S-Trityl, TentaGel HL-S-Trityl, TentaGel MB-S-Trityl, TentaGel S—S-Trityl); and

(20) Wang resins (e.g., Fmoc-Ala-Wang resin, Fmoc-Arg (Pbf)-Wang resin, Fmoc-Arg(Pmc)-Wang resin, Fmoc-Asn (Trt)-Wang resin, Fmoc-Asp(OtBu)-Wang resin, Fmoc-Cys (Acm)-Wang resin, Fmoc-Cys(StBu)-Wang resin, Fmoc-Cys (Trt) Wang resin, Fmoc-Gln(Trt)-Wang resin, Fmoc-Glu (OtBu)-Wang resin, Fmoc-Gly-Wang resin, Fmoc-His(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr(tBu)-Wang resin, Fmoc-Trp(Boc) Wang resin, Fmoc-Trp-Wang resin, Fmoc-Tyr(tBu)-Wang resin, Fmoc-Val-Wang resin).

The term "stable moiety," as used herein, preferably refers to a moiety which possess stability sufficient to allow manufacture, and which maintains its integrity for a sufficient period of time to be useful for the purposes detailed herein.

A "suitable amino-protecting group," as used herein, is well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl) 6 chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethypbenzenesulfonamide (DNMBS), benzylsulfonamide, trifluoromethylsulfonamide, and phenacylsulfonamide.

A "suitable carboxylic acid protecting group" or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group," as used herein, is well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, a-naphthyldiphenylmethyl, p-methoxyphenyldiphenylmethyl, di(p-methoxyphenyl)phenylmethyl, tri (p-methoxyphenyl)methyl, 4-(4'-bromophenacyloxyphenyl) diphenylmethyl, 4,4',4"-tris(4,5-dichlorophthalimidophenyl) methyl, 4,4',4"-tris(levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-climethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio" or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (=S).

As used herein, a "pharmaceutically acceptable form thereof" includes any pharmaceutically acceptable salts, prodrugs, tautomers, enantiomers, diastereomers, stereoisomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in "*The Organic Chemistry of Drug Design and Drug Interaction*" Richard Silverman, published by Academic Press (1992).

As used herein, the term "tautomer" includes two or more interconvertable compounds resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "amino acid" refers to a molecule containing both an amino group and a carboxyl group. Amino acids include alpha-amino acids and beta-amino acids, the structures of which are depicted below. In certain embodiments, an amino acid is an alpha amino acid.

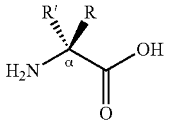

alpha-amino acid

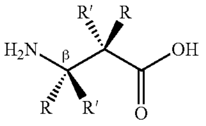

beta-amino acid

Suitable amino acids include, without limitation, natural alpha-amino acids such as D- and L-isomers of the 20 common naturally occurring alpha-amino acids found in peptides and proteins (e.g., A, R, N, C, D, Q, E, G, H, I, L, K, M, F, P, S, T, W, Y, V, as depicted in Table 1 below), unnatural alpha-amino acids (as depicted in Tables 2 and 3 below), natural beta-amino acids (e.g., beta-alanine), and unnatural beta-amino acids.

Amino acids used in the construction of peptides of the present invention may be prepared by organic synthesis, or obtained by other routes, such as, for example, degradation of or isolation from a natural source. In certain embodiments of the present invention, the formula —$[X_{AA}]$— corresponds to the natural and/or unnatural amino acids having the following formulae:

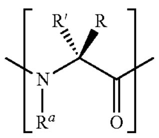

or

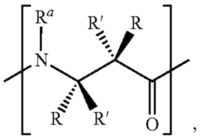

, wherein R and R' correspond a suitable amino acid side chain, as defined herein, and $R^a$ is as defined herein.

TABLE 1

| Exemplary natural | Suitable amino acid side chains | |
|---|---|---|
| alpha-amino acids | R | R' |
| L-Alanine (A) | —$CH_3$ | —H |
| L-Arginine (R) | —$CH_2CH_2CH_2$—NHC(=NH)$NH_2$ | —H |
| L-Asparagine (N) | —$CH_2C$(=O)$NH_2$ | —H |
| L-Aspartic acid (D) | —$CH_2CO_2H$ | —H |
| L-Cysteine (C) | —$CH_2SH$ | —H |
| L-Glutamic acid (E) | —$CH_2CH_2CO_2H$ | —H |
| L-Glutamine (Q) | —$CH_2CH_2C$(=O)$NH_2$ | —H |
| Glycine (G) | —H | —H |
| L-Histidine (H) | —$CH_2$-2-(1H-imidazole) | —H |
| L-Isoleucine (I) | -sec-butyl | —H |
| L-Leucine (L) | -iso-butyl | —H |
| L-Lysine (K) | —$CH_2CH_2CH_2CH_2NH_2$ | —H |
| L-Methionine (M) | —$CH_2CH_2SCH_3$ | —H |
| L-Phenylalanine (F) | —$CH_2Ph$ | —H |
| L-Proline (P) | -2-(pyrrolidine) | —H |
| L-Serine (S) | —$CH_2OH$ | —H |
| L-Threonine (T) | —$CH_2CH(OH)(CH_3)$ | —H |
| L-Tryptophan (W) | —$CH_2$-3-(1H-indole) | —H |
| L-Tyrosine (Y) | —$CH_2$-(p-hydroxyphenyl) | —H |
| L-Valine (V) | -isopropyl | —H |

TABLE 2

| Exemplary unnatural | Suitable amino acid side chains | |
|---|---|---|
| alpha-amino acids | R | R' |
| D-Alanine | —H | —$CH_3$ |
| D-Arginine | —H | —$CH_2CH_2CH_2$—NHC(=NH)$NH_2$ |
| D-Asparagine | —H | —$CH_2C$(=O)$NH_2$ |
| D-Aspartic acid | —H | —$CH_2CO_2H$ |
| D-Cysteine | —H | —$CH_2SH$ |
| D-Glutamic acid | —H | —$CH_2CH_2CO_2H$ |
| D-Glutamine | —H | —$CH_2CH_2C$(=O)$NH_2$ |
| D-Histidine | —H | —$CH_2$-2-(1H-imidazole) |
| D-Isoleucine | —H | -sec-butyl |
| D-Leucine | —H | -iso-butyl |
| D-Lysine | —H | —$CH_2CH_2CH_2CH_2NH_2$ |
| D-Methionine | —H | —$CH_2CH_2SCH_3$ |
| D-Phenylalanine | —H | —$CH_2Ph$ |
| D-Proline | —H | -2-(pyrrolidine) |
| D-Serine | —H | —$CH_2OH$ |
| D-Threonine | —H | —$CH_2CH(OH)(CH_3)$ |
| D-Tryptophan | —H | —$CH_2$-3-(1H-indole) |
| D-Tyrosine | —H | —$CH_2$-(p-hydroxyphenyl) |
| D-Valine | —H | -isopropyl |
| Di-vinyl | —CH=$CH_2$ | —CH=$CH_2$ |
| Exemplary unnatural alpha-amino acids | | R and R' are equal to: |
| α-methyl-Alanine (Aib) | —$CH_3$ | —$CH_3$ |
| α-methyl-Arginine | —$CH_3$ | —$CH_2CH_2CH_2$—NHC(=NH)$NH_2$ |
| α-methyl-Asparagine | —$CH_3$ | —$CH_2C$(=O)$NH_2$ |
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2C$(=O)$NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |
| α-methyl-Methionine | —$CH_3$ | —$CH_2CH_2SCH_3$ |
| α-methyl-Phenylalanine | —$CH_3$ | —$CH_2Ph$ |
| α-methyl-Proline | —$CH_3$ | -2-(pyrrolidine) |
| α-methyl-Serine | —$CH_3$ | —$CH_2OH$ |
| α-methyl-Threonine | —$CH_3$ | —$CH_2CH(OH)(CH_3)$ |
| α-methyl-Tryptophan | —$CH_3$ | —$CH_2$-3-(1H-indole) |
| α-methyl-Tyrosine | —$CH_3$ | —$CH_2$-(p-hydroxyphenyl) |
| α-methyl-Valine | —$CH_3$ | -isopropyl |
| Di-vinyl | —CH=$CH_2$ | —CH=$CH_2$ |
| Norleucine | —H | —$CH_2CH_2CH_2CH_3$ |

TABLE 3

| Exemplary unnatural alpha-amino acids | Suitable amino acid side chains R and R' is equal to hydrogen or —$CH_3$, and: |
|---|---|
| Terminally unsaturated alpha-amino acids and bis alpha-amino acids (e.g., modified cysteine, modified cysine, modified tryptophan, modified serine, modified threonine, modified proline, modified histidine, modified alanine, and the like). | —$(CH_2)_g$—S—$(CH_2)_g$CH=$CH_2$,<br>—$(CH_2)_g$—O—$(CH_2)_g$CH=$CH_2$,<br>—$(CH_2)_g$—NH—$(CH_2)_g$CH=$CH_2$,<br>—$(CH_2)_g$—(C=O)—S—$(CH_2)_g$CH=$CH_2$,<br>—$(CH_2)_g$—(C=O)—O—$(CH_2)_g$CH=$CH_2$,<br>—$(CH_2)_g$—(C=O)—NH—$(CH_2)_g$CH=$CH_2$,<br>—$CH_2CH_2CH_2CH_2$—NH—$(CH_2)_g$CH=$CH_2$,<br>—$(C_6H_5)$—p—O—$(CH_2)_g$CH=$CH_2$,<br>—$CH(CH_3)$—O—$(CH_2)_g$CH=$CH_2$,<br>—$CH_2CH$(—O—CH=$CH_2$)$(CH_3)$,<br>-histidine-N($(CH_2)_g$CH=$CH_2$),<br>-tryptophan-N($(CH_2)_g$CH=$CH_2$), and<br>—$(CH_2)_{g+1}$(CH=$CH_2$),<br>wherein:<br>each instance of g is, independently, 0 to 10, inclusive. |

TABLE 3-continued

| Exemplary unnatural alpha-amino acids | |
| --- | --- |
| 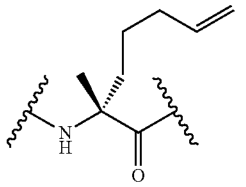 [SMILES: *N[C@](C)(CCCC=C)C(*)=O] | $R_5$ |
| 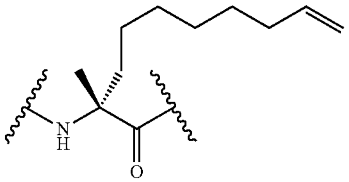 [SMILES: *N[C@](C)(CCCCCCC=C)C(*)=O] | $R_8$ |
| 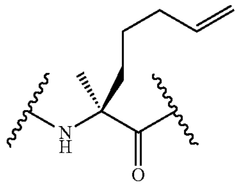 [SMILES: *N[C@@](C)(CCCC=C)C(*)=O] | $S_5$ |
| 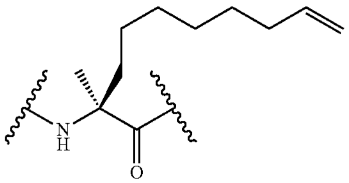 [SMILES: *N[C@@](C)(CCCCCCC=C)C(*)=O] | $S_8$ |
| 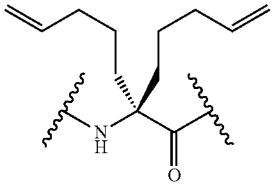 | $B_5$ |

There are many known unnatural amino acids any of which may be included in the peptides of the present invention. See, for example, S. Hunt, *The Non-Protein Amino Acids: In Chemistry and Biochemistry of the Amino Acids*, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with $—C(=O)C_6H_5$; $—CF_3$; —CN; -halo; $—NO_2$; $—CH_3$), disubstituted phenylalanines, substituted tyrosines (e.g., further substituted with $—C(=O)C_6H_5$; $—CF_3$; —CN; -halo; $—NO_2$; $—CH_3$), and statine. Additionally, the amino acids suitable for use in the present invention may be derivatized to include amino acid residues that are hydroxylated, phosphorylated, sulfonated, acylated, lipidated, and glycosylated, to name a few.

The term "amino acid side chain" refers to a group attached to the alpha- or beta-carbon of an amino acid. A "suitable amino acid side chain" includes, but is not limited to, any of the suitable amino acid side chains as defined above, and as provided in Tables 1 to 3.

For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in a crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide," "protein," "polypeptide," or "peptidic" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex. A peptide or polypeptide may be just a fragment of a naturally occurring protein or peptide. A peptide or polypeptide may be naturally occurring, recombinant, or synthetic, or any combination thereof.

The following definitions are more general terms used throughout the present application:

The term "subject," as used herein, refers to any animal. In certain embodiments, the subject is a mammal. In certain embodiments, the term "subject", as used herein, refers to a human (e.g., a man, a woman, or a child) of either sex at any stage of development.

The terms "administer," "administering," or "administration," as used herein refers to implanting, applying, absorbing, ingesting, injecting, or inhaling, the inventive polypeptide or compound.

The terms "treat" or "treating," as used herein, refers to partially or completely alleviating, inhibiting, ameliorating, and/or relieving the disease or condition from which the subject is suffering.

The terms "effective amount" and "therapeutically effective amount," as used herein, refer to the amount or concentration of a biologically active agent conjugated to an inventive polypeptide of the presently claimed invention, or amount or concentration of an inventive polypeptide, that, when administered to a subject, is effective to at least partially treat a condition from which the subject is suffering.

As used herein, when two entities are "associated with" one another they are linked by a direct or indirect covalent or non-covalent interaction. In certain embodiments, the association is covalent and the entities are "conjugated." In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently associated through a linker.

As used herein, a "label" refers to a moiety that has at least one element, isotope, or functional group incorporated into the moiety which enables detection of the inventive polypeptide to which the label is attached. Labels can be directly attached (i.e., via a bond) or can be attached by a tether (such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a tether). It will be appreciated that the label may be attached to or incorporated into the inventive polypeptide at any position.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label FITC); d) a label which has one or more photo affinity moieties; and e) a label which has a ligand moiety with one or more known binding partners (such as biotin-streptavidin, FK506-FKBP, etc.).

In certain embodiments, a label comprises a radioactive isotope, preferably an isotope which emits detectable particles, such as β particles.

In certain embodiments, the label comprises a fluorescent moiety. In certain embodiments, the label is the fluorescent label FITC. In certain embodiments, the label comprises a ligand moiety with one or more known binding partners. In certain embodiments, the label comprises the ligand moiety biotin.

BRIEF DESCRIPTION OF THE DRAWING

FIG. 7 depicts examples of bifunctional stapled peptides Tcf4-SAH p53-8, SAH p53-8-Tcf4, Bcl-9-SAH p53-8, SAH p53-8-Bcl-9 with difference orientations.

FIG. 8 depicts example sequences of bifunctional stapled peptides SAH p53-8-Bcl-9 (SEQ ID NO: 1-3) and Bcl-9-SAH p53-8 (SEQ ID NO: 4-6) with Ahx linker.

FIG. 11 depicts example sequences of bifunctional stapled peptides SAH p53-8-Tcf4 (SEQ ID NO: 17, 18) and Tcf4-SAH p53-8 (SEQ ID NO: 19, 20) with PEG linker.

FIG. 12 depicts examples using cross-linkers to join the two peptide domains (targeting domain and effector domain).

FIG. 13 depicts examples of different types of spacers between NHS and maleimide.

FIG. 25 includes the sequences and biological activity of exemplary repressive domains. (A) Sequences of SID peptide and stapled versions thereof. Asterisks indicate the incorporation of non-natural amino acids for peptide stapling. (B) Sample fluorescent polarization experiment data for SID2 and SID5 as compared to wild type SID used to determine dissociation constants ($K_D$). (C) Confocal microscopy of Hela cells treated with FITC-conjugated SID-series peptides. SID2 and SID5 reveal robust cellular penetration.

FIG. 26 includes the sequences and biological activity of exemplary activation domains. (A) Sequences of MLL and cMyb peptides and stapled versions thereof. Asterisks indicate the incorporation of non-natural amino acids for peptide stapling. NT: not tested. (B) Sample fluorescent polarization experiment data for MLL1-2 used to determine dissociation constants ($K_D$). (C) Confocal microscopy of U2OS cells treated with FITC-conjugated MLL-series peptides. MLL1-2 reveals robust cellular penetration.

DETAILED DESCRIPTION OF THE INVENTION

Introduction

Figure 1:
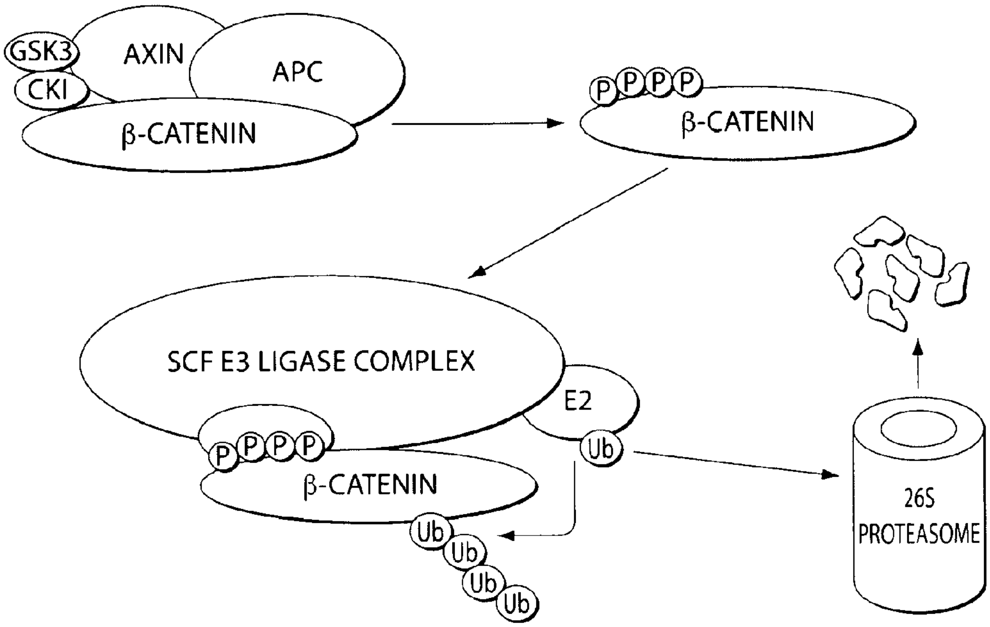
FIG. 1 depicts the endogenous β-catenin degradation pathway as adapted from Barker and Clevers, *NRDD,* 5, 998-1014 (2006), incorporated herein by reference.

The present invention stems from the recognition of a new use for stapled or stitched peptides. Given the stability of such peptides they may be used as agents for recruiting proteins or other biomolecules to a particular protein, nucleic acid, other biomolecule, cell, or organelle or other cellular entities. The invention thus relates to bifunctional stapled or stitched peptides that can tether, or bring together cellular entities. One domain of the bifunctional peptide acts as a targeting moiety that binds to a target; the other domain acts as an effector domain to recruit a protein, protein complex, or other biomolecule to the target. In essence, the bifunctional peptide works to bring two proteins or other biomolecules in proximity to one another. The targeting domain, the effector domain, or both domains may be stapled or stitched to stabilize the conformation of the peptide.

In certain embodiments, bifunctional stapled or stitched peptides of the invention can be used to tether any two biomolecules (such as polypeptides) together. A polypeptide can be, for example, a single polypeptide, such as a protein, or can be a complex comprising two or more polypeptides that associate with each other, such as a protein complex.

To tether, as used herein, means to bring into close proximity cellular entities (e.g., proteins, nucleic acids, membranes, organelles, etc.). In certain embodiments, when two polypeptides are brought together (or tethered) by a bifunctional stapled peptide of the invention, they might be coming into such close molecular contact that one polypeptide (an "effector" biomolecule) might alter or modify the other polypeptide (a "target" biomolecule).

Structure of an Inventive Bifunctional Peptide

In certain embodiments, stapled or stitched bifunctional peptides comprise three building blocks: A-L-E, comprising a targeting domain (A), a linker (L), and an effector domain (E) that are generally arranged as follows:

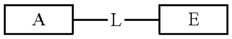

wherein A and/or E is a stapled or stitched peptide, and L is a linker; wherein A is a targeting domain and E is an effector domain. A and E are targeting or effector domains, that are sequences of amino acids that may or may not be stapled that specifically associate or bind to polypeptides, such as a target biomolecule or an effector biomolecule. Any part of the peptide A may be linked to any part of the peptide E through the linker L. In certain embodiments, the linkage is N-terminus to N-terminus. In certain embodiments, the linkage is C-terminus to N-terminus. In certain embodiments, the linkage is C-terminus to C-terminus. In still other embodiments, the linkage may be through interior amino acids of one or both peptides. As will be appreciated by one on skill in the art, the linkage is typically positioned in such a way as to avoid interfering with the binding activity of the peptide. The linkage may also be positioned in such a way to avoid interfering with the stapling of the peptide.

In certain embodiments, where A is the targeting domain and specifically associates or binds to a target, E is the effector domain and specifically associates or binds an effector biomolecule capable of modifying the target bound or associated with the targeting domain A. L is a chemical linker that covalently links A and E. The linker L may be aliphatic or heteroaliphatic. In certain embodiments, linker L is 1-50 atoms, in length, and may be optionally substituted. In certain embodiments, linker L is 1-25 atoms, in length, and may be optionally substituted.

A and E can have any length, that is they may comprise any number of amino acids. The number of amino acids can be four or more, 5, 6, 7, 8, 9, 10, 11, 12, 13, 14, 15, 16, 17, 18, 19, 20, 25, 30, 35, 40, 45, 50, 100 or more, or any number of amino acids in between 4 and 100. A and E can comprise a number of amino acids that is the minimal number of amino acids sufficient to specifically bind or associate with either the target or the effector biomolecule. The amino acid sequence of one or both of the domains may be substantially similar to or homologous to a known peptide.

In one aspect, the present invention provides a bifunctional stapled peptide wherein one or both domains comprise the formula:

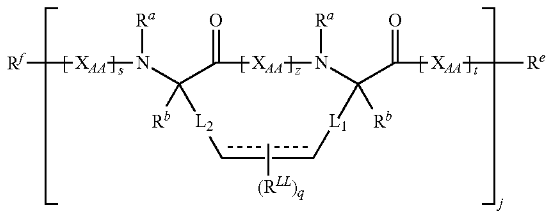

wherein each instance of $L_1$ and $L_2$ is, independently, a bond; cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, a bond to the linker moiety, $-R^E$, $-OR^E$, $-N(R^E)_2$, or $-SR^E$, wherein each instance of $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups of $-N(R^E)_2$ together form a substituted or unsubstituted 5- to 6-membered heterocyclic or heteroaromatic ring;

each instance of $R^f$ is, independently, a bond to the linker moiety; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ of a terminal amino acid together form a substituted or unsubstituted 5- to 6-membered heterocyclic or heteroaromatic ring;

each instance of $R^{LL}$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{LL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of z is, independently, an integer between 2 to 6;

each instance of j is, independently, an integer between 1 to 10;

each instance of s and t is, independently, an integer between 0 and 100;

each instance of q is, independently, an integer between 0 to 2; and

----------  corresponds to a single or double bond.

In another aspect, the present invention provides a bifunctional stitched peptide wherein one or both domains comprise the formula (i.e.; a peptide with multiple staples):

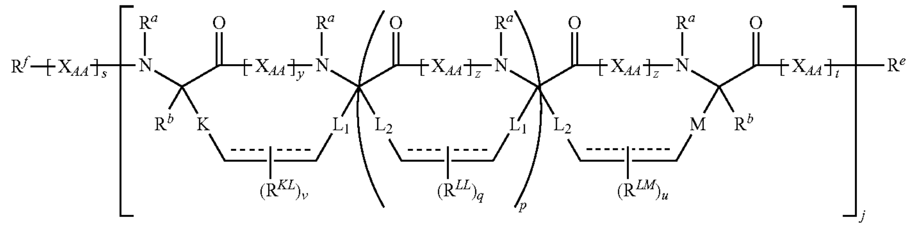

wherein each instance of K, $L_1$, $L_2$, and M, is, independently, a bond; cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl;

substituted or unsubstituted thiol; substituted or unsubstituted amino; cyano; isocyano; halo; or nitro;

each instance of $R^e$ is, independently, a bond to the linker moiety, —$R^E$, —$OR^E$, —$N(R^E)_2$, or —$SR^E$, wherein each instance of $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups of —$N(R^E)_2$ together form a substituted or unsubstituted 5- to 6-membered heterocyclic or heteroaromatic ring;

each instance of $R^f$ is, independently, a bond to the linker moiety; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 2; and $\overline{\phantom{xxxxx}}$ corresponds to a single or double bond.

In certain embodiments, one or both of peptides A and E is an alpha-helical polypeptide. In certain embodiments, peptide A is substantially alpha-helical. In certain embodiments, peptide E is substantially alpha-helical. As used herein, the phrase "substantially alpha-helical" refers to a polypeptide adopting, on average, backbone (φ, ψ) dihedral angles in a range from about (−90°, −15°) to about (−35°, −70°). Alternatively, the phrase "substantially alpha-helical" refers to a polypeptide adopting dihedral angles such that the ψ dihedral angle of one residue and the φ dihedral angle of the next residue sums, on average, about −80° to about −125°. In certain embodiments, the polypeptide adopts dihedral angles such that the ψ dihedral angle of one residue and the φ dihedral angle of the next residue sums, on average, about −100° to about −110°. In certain embodiments, the polypeptide adopts dihedral angles such that the ψ dihedral angle of one residue and the φ dihedral angle of the next residue sums, on average, about −105°. Furthermore, the phrase "substantially alpha-helical" may also refer to a polypeptide having at least 50%, 60%, 70%, 80%, 90%, or 95% of the amino acids provided in the polypeptide chain in an alpha-helical conformation, or with dihedral angles as specified herein. Confirmation of a polypeptide's alpha-helical secondary structure may be ascertained by known analytical techniques, such as x-ray crystallography, electron crystallography, fiber diffraction, fluorescence anisotropy, circular dichroism (CD), and nuclear magnetic resonance (NMR) spectroscopy.

The linker associating polypeptide A with polypeptide E may be any chemical moiety capable of associating the two polypeptides under conditions in which the bifunctional polypeptide will be used. The linker may be as simple as a covalent bond, or it may be a polymeric linker many atoms in length. In certain embodiments, the linker is a polypeptide or based on amino acids. In other embodiments, the linker is not peptide like. In certain embodiments, the linker is a covalent bond (e.g., a carbon-carbon bond, disulfide bond, carbon-heteroatom bond, etc.). In certain embodiments, the linker is a carbon-nitrogen bond of an amide linkage. In certain embodiments, the linker is a cyclic or acyclic, substituted or unsubstituted, branched or unbranched aliphatic or heteroaliphatic linker. In certain embodiments, the linker is polymeric (e.g., polyethylene, polyethylene glycol, polyamide, polyester, etc.). In certain embodiments, the linker comprises a monomer, dimer, or polymer of aminoalkanoic acid. In certain embodiments, the linker comprises an aminoalkanoic acid (e.g., glycine, ethanoic acid, alanine, beta-alanine, 3-aminopropanoic acid, 4-aminobutanoic acid, 5-pentanoic acid, etc.). In certain embodiments, the linker comprises a monomer, dimer, or polymer of aminohexanoic acid (Ahx). In certain embodiments, the linker is based on a carbocyclic moiety (e.g., cyclopentane, cyclohexane). In other embodiments, the linker comprises a polyethylene glycol moiety (PEG). In other embodiments, the linker comprises amino acids. In certain embodiments, the linker comprises a peptide. In certain embodiments, the linker comprises an aryl or heteroaryl moiety. In certain embodiments, the linker is based on a phenyl ring. In certain embodiments, the linker comprises a triazole moiety (i.e., the product of a Huisgen cycloaddition reaction). The linker may include functionalized moieties to facilitate attachment of a nucleophile (e.g., thiol, amino) from the peptide to the linker. Any electrophile may be used as part of the linker. Exemplary electrophiles include, but are not limited to, activated esters, activated amides, Michael acceptors, alkyl halides, aryl halides, acyl halides, and isothiocyanates. In certain embodiments, the linker includes a maleimide group. In certain embodiments, the linker includes a NHS ester. In certain embodiments, the linker includes both a NHS ester and a maleimide group. For example, a cyclohexane ring may be substituted with an NHS ester and a maleimide group. Examples of covalent conjugation strategies and suitable chemical conditions using a variety of linkers and/or functional groups to associate polypeptide A with polypeptide E are set forth in FIGS. 27 to 32. In certain embodiments, thiol-maleimide conjugates are generated. In other embodiments, 1,4- or 1,5-triazole conjugates are generated.

Uses of the Bifunctional Peptide

Bifunctional peptides of the invention may be used to tether two cellular entities together. In certain embodiments, by tethering two cellular entities, it is desired that one entity brings about a change in the other entity. One entity that brings about the change in the other entity is an effector biomolecule that modifies the other entity, which is the target. The modification of the target biomolecule modifies or alters some characteristic (e.g., biological activity) of the target. In some embodiments, by tethering two cellular entities, it is desired that the two entities are essentially irreversibly tethered together. For example, certain effector biomolecules may associate with a target or dissociate from a target naturally upon certain stimuli or molecular signals. Bifunctional peptides of the invention may be used to tether two cellular entities together irreversibly so that they do not dissociate upon such stimuli or other signals and remain associated. The effector biomolecule, for example, can be a cellular inhibitor of the target, or a particular molecular complex, that associates with the target to keep it in a certain intracellular localization (e.g., cytosolic or nuclear). In other embodiments, bifunctional peptides can be used to tether biomolecules together that would only associate naturally upon certain stimuli or molecular signals, in the absence of such stimuli. In other embodiments, biomolecules can be tethered together that do not naturally associate with each other. "Naturally" as used herein means in a cellular context under physiological conditions including diseased conditions.

In certain embodiments, bifunctional stapled peptides can be used to alter one or more characteristics of the target. In certain embodiments, the characteristics of the target are altered in such a way that this alteration affects cell fate and/or cell behavior. In certain embodiments, changes in cell fate or cell behavior as a result of changes in one or more characteristics of the target affect the disease state of a subject, such as a mammal, for example, a human. In certain embodiments, bifunctional stapled peptides can be used to treat disease. In certain embodiments bifunctional stapled peptides can be used to probe or elucidate biological pathways in research. The probing of a biological pathway can be performed both in vitro such as in cell or tissue culture, or in vivo, such as in an animal, e.g., humans, mice, rats, hamsters, fish, or primates.

In some embodiments, the two cellular entities are polypeptides, such as proteins and associated protein complexes. In certain embodiments, alterations or modifications of one entity (the target biomolecule) can be the result of an enzymatic activity of the other entity (the effector molecule). For proteins, for example, such alterations or modifications may comprise any of the posttranslational modifications known in the art.

Posttranslational modifications include, but are not limited to, ubiquitination, phosphorylation, acetylation, glycosylation, methylation, sumoylation, urmylation, neddylation, proteolysis, lipidation, acylation, farnesylation, geranylgeranylation and/or ligation. It will be appreciated by one of ordinary skill in the art that posttranslational modifications can include the addition of a chemical moiety as well as the removal of such a chemical moiety, as used herein, are any chemical groups (such as proteins, sugars, or inorganic molecules, for example phosphate) that can be added or removed to and from a polypeptide entity. Examples of such chemical moieties are proteins, such as ubiquitin (Ub), and ubiquitin-like proteins (Ubl) SUMO, Urm1, and Nedd8, carbohydrates such as glycans, and small organic or inorganic groups such as phosphate, acetyl-, acyl-, or methyl-groups, or lipids. Chemical moieties may also include nucleic acids. Chemical moieties may be attached or removed from a target biomolecule by a variety of enzymatically active effector biomolecules.

In certain embodiments, the effector domain of the bifunctional peptide recruits a ubiquitinating enzyme or ubiquitination machinery to a target protein. Ubiquitination of a target protein typically results in degradation of the ubiquitinated protein by the proteasome. Ubiquitin is attached to a protein, by ubiquitin ligases, such as E3 ligase. E3 ligases can be single polypeptide chain enzymes, such as MDM2 or E6AP, or protein complexes, such as Skp1-Cullin-F-box (Skp1, Cul1/Cdc53, Roc1/Hrt/Rbx1, SCF), anaphase-promoting complex (APC), or BRCA1-Bard1 complex. These complexes may associate with adaptor proteins, such as cdh1 and cdc20 for APC, and various F-box proteins for SCF, that provide natural substrate specificity, and further associate with E2 ubiquitin conjugating enzymes (UBCs).

Typically, ubiquitin is attached to a target protein through a series of catalytic steps. Ubiquitin is first activated by a ubiquitin activating enzyme E1. The E1 enzyme catalyzes two reactions—ATP-dependent adenylation of the carboxylate followed by thiocarboxylate formation with an internal cysteine of E1. This is followed by a trans-thiolation reaction that transfers Ub/Ubl to the active cysteine of the E2 enzyme. E2s then directly transfer the Ub/Ubl to the target lysine of the target protein, often aided by E3 ligase. Ub/Ubls can be transferred by a further trans-thiolation reaction to HECT E3 ligases, which then transfer the Ub/Ubl to substrates. In many cases multiple rounds of ubiquitination are catalyzed by a specialized E3 ligase resulting in poly-Ub adducts.

Ubiquitins can be removed by de-ubiquitinating enzymes (DUBs), which are proteases. Examples of cysteine protease DUBs are: the ubiquitin-specific processing protease (USP/UBP) superfamily; the ubiquitin C-terminal hydrolyase (UCH) superfamily; the ovarian tumor (OTU) superfamily; and the Machado-Josephin domain (MJD) superfamily.

SUMO (small ubiquitin-related modifier) can be attached by sumoylation-dependent ubiquitin ligases, such as the sumoylation-dependent E3 ligases RanBP2, Pc2 and members of the PIAS family. In humans and mice, the SUMO family consists of three members, SUMO-1, SUMO-2, and SUMO-3, which are encoded by separate genes. SUMO conjugation requires sequential E1-dependent activation, E2-dependent conjugation, and E3-dependent ligation steps. The human SUMO E1 enzyme comprises a heterodimer of the SAE1 and SAE2 proteins and forms a thioester bond with glycine 97 of SUMO-1. Subsequently, SUMO-1 is transferred by transesterification to the SUMO-specific E2-conjugating enzyme, Ubc9. Ubc9 can directly conjugate the carboxy terminal glycine of SUMO to lysines in target proteins that are situated in the consensus motif yKxE/D, where y stands for valine, leucine, isoleucine, methionine, or phenylalanine; and x stands for any amino acid.

SUMO can be removed by desumoylation proteins or SUMO proteases, such as SuPr1, SENP1 (sentrin/SUMO-specific proteases), or ULPs (ubiquitin-like protein specific proteases).

Nedd8, a ubiquitin-like small protein modifier can be attached by a process called neddylation, which is similar to ubiquitination. Neddylation utilizes the E1 activating-enzyme complex composed of two subunits, APP-BP1 and UBA3, and the E2 conjugating-enzyme, UBC12. Known substrates of neddylation are Cullin family proteins: Cul1, Cul2, Cul3, Cul4A, Cul4B, and Cul5. Neddylation of certain cullins (e.g., Cullin-1), which are part of the SCF complexes might enhance E2-ubiquitin recruitment to SCF and might be required for ubiquitination by SCF of certain E3 ligase substrates.

Deneddylation, which removes the Nedd8 moiety, might be accomplished by isopeptidase activity such as that of the COP9/signalosome (CSN) and CAND1.

In certain embodiments, the effector domain recruits an enzyme that catalyzes the acetylation of the of the target protein. Acetyl groups can be attached by acetylases, such as, for example, PCAF/GCN5, p300/CBP, TAF250, SRC1 and MOZ, TIP60 or BRCA2, which may modify histone and/or non-histone proteins. Acetylases may be part of large molecular weight complexes, such as TIP60, STAGA (SPT3-TAF9-GCN5/PCAF), ATAC (Ada Two-A containing), or NuA4 histone acetylase complex or may associate with transcriptions factors, such as, for example, E2Fs, TAFs, p53, and MyoD.

Acetyl groups can be removed by deacetylases, such as, for example, HDAC1, 2, 3, 4, 5, 6, 7, 8, 9, 10, and 11, that may modify histone and/or non-histone proteins. HDACs may be part of large molecular weight complexes, such as NuRD, Sin3, SMRT, and N-CoR complex or may associate with transcriptions factors, such as, for example, Rb, YY1, Sp1, MEF2, BRCA1, p53, c-Ski, and Ikaros.

In other embodiments, phosphorylation is typically accomplished by kinases. Kinases transfer a phosphate group from ATP or other nucleotides to the substrate via the side chain of an amino acid. Most kinases transfer the phosphate group to serine or threonine (such as MAP kinases, ERK, JNK, and p38), others to tyrosine, and a number (dual-specificity kinases) to all three amino acids. There are also protein kinases that phosphorylate other amino acids, including histidine kinases that phosphorylate histidine residues.

Dephosphorylation might be accomplished by phosphatases that remove a phosphate group from its substrate by hydrolyzing phosphoric acid monoesters into a phosphate ion and a molecule with a free hydroxyl or amino group. Phosphatases include Cysteine-Dependent Phosphatases (CDPs) and metallo-phosphatases. Serine/threonine-specific protein phosphatases include, for example, PP1 (α, β, γ1, γ2), PP2 (formerly 2A), PP3 (formerly 2b, also known as calcineurin), PP2C, PP4, PP5, and PP6. Tyrosine-specific phosphatase include, for example, PTP1B. Dual specificity phosphatases include, for example, VHR, DUSP1-DUSP28. Histidine Phosphatases include, for example, PHP. Lipid Phosphatases include, for example, PTEN.

Methyl groups may be added to arginines of substrates by protein methylases, such as protein methylase I, II, or III; and PRMT1 and PRMT5 (protein arginine methyltransferases 1 and 5), yielding for example, monomethyl or dimethyl arginines. Methylases can transfer methyl groups using, for example, S-adenosyl-L-methionine as a donor. Known protein methylation substrates include myelin basic protein (MBP), and heterogeneous ribonucleoprotein A1 (hnRNP A1). Methylases, known as HMT (histone methyl transferases), such as, for example, SUV39H1, G9a, EHMT1, Trithorax, Ash1 and Dot1, or other enzymes, modify primarily histone proteins, particularly on lysine and arginine residues resulting in mono-, di-, or tri-methylated substrates.

Demethylation might be accomplished by demethylases, such as LSD1, JMJD, or JHDM. Known targets of demethylases are for example histone proteins.

Carbohydrate moieties can be added to proteins or lipids by glycosyltransferases, such as GlcNAc-transferase (GnTI, II, II, IV, V), galactosyltransferase, glucuronyltransferase, sialyltransferase, xylosyltransferase, fucosyltransferase, and mannosyltransferase. Glycosyltransferases transfer a monosaccharide unit from an activated sugar phosphate to an acceptor molecule, for example, tyrosine, serine, or threonine to give O-linked glycoproteins, or to asparagine to give N-linked glycoproteins. Mannosyl groups may be transferred to tryptophan to generate C-mannosyl tryptophan. The result of glycosyl transfer can be a monosaccharide glycoside, an oligosaccharide, or a polysaccharide. Common donors for glycosyltransferases are, for example, UDP-glucose, UDP-galactose, UDP-GlcNAc, UDP-GalNAc, UDP-xylose, UDP-glucuronic acid, GDP-mannose, GDP-fucose, and CMP-sialic acid. Lipid linked glycosyl donors can also be used, where the lipid is frequently a terpenoid such as dolichol or polyprenol.

Carbohydrates can be removed from proteins or lipids by glycosidases (glycoside hydrolases) that catalyze the hydrolysis of the glycosidic linkage of sugars.

Prenylation is a lipid posttranslational modification of proteins which typically occurs at a cysteine residue. The specific sequence recognized by prenyltransferases consists either of the CaaX box for farnesyltransferase (FTase) and geranylgeranyltransferase 1 (GGTase1) or C-terminal cysteines of Rab GTPases in the case of geranylgeranyltransferase 2 (GGTase2). The anchor can be of farnesyl (3 isoprenyl units) or of geranylgeranyl (4 isoprenyl units) type. This modification allows membrane attachment or association of the pyrenylated protein. Farnesylation involves the enzyme farnesyltransferase (FTase) transferring a farnesyl group from farnesyl pyrophosphate (FPP) to a substrate, e.g., Ras protein. A related enzyme, geranylgeranyltransferase I (GeTase I), transfers a geranylgeranyl group to the substrate, e.g., K and N-Ras.

It will be appreciated by one of ordinary skill that any of the modification described herein may occur at one or more sites (or target amino acids) on the target biomolecule. For example, a target entity can be phosphorylated at multiple sites, that is one, two, three, four or more sites. Chemical moieties can be attached as monomers or multimers to the same site, for ubiquitin, and the same amino acid target site can be modified one or more times with the same chemical moiety, such as, for example, mono-, di-, or tri-methylation.

It should further be appreciated that addition, removal, or replacement of chemical moieties may have different effects on the target biomolecule. Many of these effects are well known in the art. Some of the modifications can be additive, for example, in activating a target biomolecule to carry out a certain function, some modifications may have opposing effects, for example protecting a substrate from or marking it for degradation.

For example, SUMO-1 and ubiquitin can compete for the same sites on a target biomolecule and can have opposing effects. Poly-ubiquitination of the target biomolecule can lead to degradation by the 26S proteasome, while SUMOylation can protect the target biomolecule from degradation (this is known, for example for IkappaB). DNA damage-induced acetylation on specific sites of the tumor suppressor protein Rb can prevent phosphorylation on these sites (e.g., by CDKs) and keeping Rb in an active conformation. Phosphorylation of specific sites of the E2F1 transcription factor (e.g., by ATM/ATR) promotes E2F1 acetylation (e.g., by CBP/p/CAF).

High expression of some glycosyl epitopes promotes invasion and metastasis, such as, for example, β6GlcNAc branching in N-linked structure; sialyl-Tn in O-linked structure; sialyl-Lex, sialyl-Lea, and Ley in either N-linked, O-linked, or lipid-linked structure; GM2, GD3, and sialyl-Gb5 in lipid-linked structure. High expression of other glycosyl epitopes suppresses tumor progression, such as, for example, β4GlcNAc competitive with β6GlcNAc; histo-blood group A and B competitive with sialylated structures including sialyl-Lex and sialyl-Lea; Gb5 competitive with sialyl-Gb5.

For example, one common glycosylation change associated with malignancy is enhanced β6GlcNAc side chain branching of N-linked structure, caused by enhanced activity of GnT-V, and counteracting β4GlcNAc (bisecting GlcNAc) synthesized by GnT-III. The level of both glycosyl epitopes is determined by the balance between GnT-V and GnT-III. Enhanced GnT-III gene can inhibit β6GlcNAc branching, which can lead to suppression of metastasis. In metastasis, one of the targets appears to be E-cadherin, in which enhanced β4GlcNAc reduces β6GlcNAc branching, leading to enhanced cadherin-dependent cell-to-cell adhesion and consequent suppression of metastasis. A bifunctional peptide of the invention comprising an effector domain that specifically binds to GnT-III and a targeting domain that specifically binds to E-cadherin is used to tether GnTIII to E-cadherin in cancer cells, leading to increased β4GlcNAc modification on E-cadherin and suppression of metastasis.

Further, it is well known in the art that certain modifications result in the subsequent recruitment of additional enzymes to the modified target biomolecule that add or remove other modifications. For example, p53 accumulation and activation are regulated through posttranslational modifications such as phosphorylation, acetylation and ubiquitination. Phosphorylation of Ser15, Thr18, Ser20 and Ser37 stabilizes p53 by disrupting interaction between p53 and MDM2, whereas phosphorylation at the p53 C-terminus such as at Ser315 and Ser392 are reported to regulate the oligomerization state and sequence-specific DNA binding ability of p53.

The PI3K family including ATM (ataxia telangiectasia mutated) and ATR (ATM- and Rad3-related) are mainly responsible for p53 phosphorylation. ATM mainly phosphorylates the Ser15 residue in response to irradiation and chemotherapeutic drugs, while ATR especially phosphorylates both Ser15 and Ser37 residues in response to UV and inhibitors of replication.

Phosphorylation of p53 leads to subsequent acetylation. For example, phosphorylation at N-terminal serines, such as Ser15, Ser33 and Ser37 recruits p300/CBP and PCAF to induce p53 acetylation in response to DNA damage. Phosphorylation of p53 at Ser20 or Thr18 can stabilize the p300-p53 complex and thus induce p53 acetylation. p300/CBP acetylates p53 at K305, K372, K373, K381 and K382, whereas PCAF acetylates p53 at K320. Tip60 specifically acetylates p53 at K120 in response to DNA damage. p53 acetylation can increase p53 sequence-specific DNA-binding capacity or enhance its stabilization by inhibiting ubiquitination of p53 mediated by MDM2.

A bifunctional peptide of the invention comprising an effector domain that specifically binds to ATM or ATR and a targeting domain that specifically binds to p53 is used to tether the PI3 kinase to p53 in cancer cells, in which p53 is not fully inactivated as a result of mutations, to promote phosphorylation and subsequent p53 acetylation, leading to stabilization and activation of p53.

A bifunctional peptide of the invention comprising an effector domain that specifically binds to p300 or PCAF and a targeting domain that specifically binds to p53 is used to tether the acetylase to p53 in cancer cells, in which p53 is not fully inactivated as a result of mutations, to promote p53 acetylation, leading to stabilization and activation of p53.

In some embodiments, the effector biomolecule adds, removes or replaces one or more chemical moieties on one or more amino acid sites of the target biomolecule. In certain embodiments, the modification leads to a desired change in fate of the target biomolecule, such as activation, de-activation, changes in intracellular localization, stabilization, de-stabilization, changes in substrate specificity or enzyme fidelity, or changes in protein folding of the target biomolecule.

It should therefore be appreciated that by controlling one or more specific posttranslational modifications one can control many characteristics of a target biomolecule, such as, for example, the enzymatic activity, substrate specificity, intracellular localization, degradation, half-life, localization, protein-protein interaction, protein-nucleic acid interaction, and stability of the target biomolecule. In certain embodiments, these changes in fate of the target biomolecule lead to a change in the fate of the cell harboring the target biomolecule.

In certain embodiments, bifunctional stapled peptides of the invention can be used to tether an effector biomolecule with a target biomolecule to modify the folding state of the target biomolecule. For example, certain nascent polypeptide chains can encounter problems during the protein folding process. Improperly folded or misfolded proteins might lose some or all of their activity, might gain ectopic activities, might be mislocalized within the cell or might form disruptive protein aggregates. Misfolded proteins are known to be involved in the development of many diseases, particularly neuronal or brain diseases. For example, misfolded alpha-synuclein is associated with Parkinson's Disease.

In certain embodiments, bifunctional stapled peptides of the invention can be used to tether chaperones to misfolded proteins or proteins at risk of misfolding. Chaperones can also be tethered to protein complexes to aid complex formation. There are several families of chaperones, such as, for example, 40-kDa heat shock protein (HSP40; DnaJ), 60-kDa heat shock protein (HSP60; GroEL), 70-kDa heat shock protein (HSP70; DnaK), 90-kDa heat shock protein (HSP90; HtpG), and 100-kDa heat shock protein (HSP100; Clp). Other chaperones include BiP, GRP94, GRP170, calnexin, calreticulin, HSP47, ERp29, protein disulfide isomerase, peptidyl prolyl cis-trans-isomerase, and ERp57.

The present invention provides a method of treating a disease, disorder, or condition comprising administering to a subject diagnosed with or having susceptibility to the disease, disorder, or condition, a therapeutically effective amount of an inventive bifunctional polypeptide, or pharmaceutically acceptable form thereof. Exemplary diseases, disorders, or conditions which may be treated by administration of an inventive bifunctional polypeptide comprise proliferative, neurological, immunological, endocrinologic, cardiovascular, hematologic, and inflammatory diseases, disorders, or conditions, and conditions characterized by premature or unwanted cell death.

As used herein a proliferative disease, condition, or disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Examples of cancers treatable by the above method include carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi's sarcoma.

Examples of hematopoietic neoplastic disorders treatable by the above method includes diseases involving hyperplastic/neoplastic cells of hematopoietic origin, e.g., arising from myeloid, lymphoid or erythroid lineages, or precursor cells thereof. In certain embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Examples of proliferative breast disease treatable by the above method includes epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of proliferative disorders of the lung treatable by the above method include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, non-inflammatory pleural effusions, pneumothorax, and pleural tumors, including solitary fibrous tumors (pleural fibroma) and malignant mesothelioma.

Examples of proliferative disorders of the colon treatable by the above method include, but are not limited to, non-neoplastic polyps, adenomas, familial syndromes, colorectal carcinogenesis, colorectal carcinoma, and carcinoid tumors.

Examples of proliferative disorders of the liver treatable by the above method include, but are not limited to, nodular hyperplasias, adenomas, and malignant tumors, including primary carcinoma of the liver and metastatic tumors.

Examples of proliferative disorders of the ovary treatable by the above method include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

The bifunctional polypeptides described herein can also be used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia. The polypeptides of the invention that act to decrease apoptosis can be used to treat disorders associated with an undesirable level of cell death. Thus, the anti-apoptotic peptides of the invention can be used to treat disorders such as those that lead to cell death associated with viral infection, e.g., infection associated with infection with human immunodeficiency virus (HIV).

A wide variety of neurological diseases are characterized by the gradual loss of specific sets of neurons, and the anti-apoptotic peptides can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. The anti-apoptotic peptides of the invention can be used to treat all such disorders associated with undesirable cell death.

Some examples of neurologic disorders that can be treated with the bifunctional polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob disease, Gerstmann Straussler-Scheinker Syndrome, Bovine Spongiform Encephalitis, a Prion-mediated disease, Huntington's disease, Pick's disease, Amyotrophic Lateral Schlerosis (ALS), Parkinson's disease, and Lewy Body Disease.

Some examples of endocrinologic disorders that can be treated with the bifunctional polypeptides described herein include but are not limited to diabetes, hypothyroidism, hypopituitarism, hypoparathyroidism, hypogonadism, fertility disorders, etc.

Some examples of immunologic disorders that can be treated with the polypeptides described herein include but are not limited to organ transplant rejection, arthritis, lupus, IBD, Crohn's disease, asthma, multiple sclerosis, diabetes, Graft versus host diseases, autoimmune diseases, psoriasis, rheumatoid arthritis, etc.

Examples of cardiovascular disorders that can be treated or prevented with the polypeptides of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices.

The inventive bifunctional polypeptides may serve to treat the above-described diseases, disorders, or conditions, by tethering cellular entities, such as proteins, together, as described herein.

Pharmaceutical Compositions

The present invention provides pharmaceutical compositions comprising an inventive bifunctional polypeptide, or a pharmaceutically acceptable form thereof, and a pharmaceutically acceptable excipient. Such pharmaceutical compositions may optionally comprise one or more additional biologically active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive bifunctional polypeptide, as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds, such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy,* $21^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include, but are not limited to, natural emulsifiers {e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays {e.g. bentonite [aluminum silicate] and Veegum [magnesium aluminum silicate]), long chain amino acid derivatives, high molecular weight alcohols {e.g. stearyl alcohol, cetyl alcohol, oleyl alcohol, triacetin monostearate, ethylene glycol distearate, glyceryl monostearate, and propylene glycol monostearate, polyvinyl alcohol), carbomers {e.g., carboxy polymethylene, polyacrylic acid, acrylic acid polymer, and carboxyvinyl polymer), carrageenan, cellulosic derivatives {e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as CREMOPHOR, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients, such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

In some embodiments, a therapeutically effective amount of an inventive pharmaceutical composition is delivered to a patient and/or organism prior to, simultaneously with, and/or after diagnosis with a disease, disorder, and/or condition. In some embodiments, a therapeutic amount of an inventive composition is delivered to a patient and/or organism prior to, simultaneously with, and/or after onset of symptoms of a disease, disorder, and/or condition. In some embodiments, the amount of inventive conjugate is sufficient to treat, alleviate, ameliorate, relieve, delay onset of, inhibit progression of, reduce severity of, and/or reduce incidence of one or more symptoms or features of the disease, disorder, and/or condition.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the bifunctional polypeptides of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that inventive bifunctional polypeptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive polypeptide may be administered concurrently with another biologically active agent used to treat the same disorder), and/or they may achieve different effects (e.g., control of any adverse effects). In some embodiments, polypeptides of the invention are administered with a second biologically active agent that is approved by the U.S. Food and Drug Administration.

In will further be appreciated that biologically active agents utilized in this combination may be administered together in a single composition or administered separately in different compositions.

In general, it is expected that biologically active agents utilized in combination be utilized at levels that do not exceed the levels at which they are utilized individually. In some embodiments, the levels utilized in combination will be lower than those utilized individually.

In some embodiments, inventive pharmaceutical compositions may be administered in combination with any biologically active agent or therapeutic regimen that is useful to treat, alleviate, ameliorate, relieve, delay onset of, inhibit progression of, reduce severity of, and/or reduce incidence of one or more symptoms or features of cancer. For example, inventive compositions may be administered in combination with traditional cancer therapies including, but not limited to, surgery, chemotherapy, radiation therapy, hormonal therapy, immunotherapy, complementary or alternative therapy, and any combination of these therapies.

In some embodiments, inventive compositions are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g., chemotherapy, radiation therapy, hormonal therapy, immunotherapy, complementary or alternative therapy) may be employed.

In some embodiments, inventive compositions are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g., a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, inventive compositions are administered in combination with immunotherapy. Immunotherapy is the use of immune mechanisms against tumors which can be used in various forms of cancer, such as breast cancer (e.g., trastuzumab/Herceptin®), leukemia (e.g., gemtuzumab ozogamicin/Mylotarg®), and non-Hodgkin's lymphoma (e.g., rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful at preventing infection with these types of HPV and, thus, are able to prevent the majority of cervical cancer cases (Harper et al., 2004, *Lancet,* 364:1757).

In some embodiments, inventive compositions are administered in combination with complementary and alternative medicine treatments. Some exemplary complementary measures include, but are not limited to, botanical medicine (e.g., use of mistletoe extract combined with traditional chemotherapy for the treatment of solid tumors); acupuncture for managing chemotherapy-associated nausea and vomiting and in controlling pain associated with surgery; prayer; psychological approaches (e.g., "imaging" or meditation) to aid in pain relief or improve mood. Some exemplary alternative measures include, but are not limited to, diet and other lifestyle changes (e.g., plant-based diet, the grape diet, and the cabbage diet).

In some embodiments, inventive compositions are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, inventive compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g., morphine, oxycodone, antiemetics, etc.); nausea and vomiting can be treated with 5-$HT_3$ inhibitors (e.g., dolasetron/Anzemet®, granisetron/Kytril®, ondansetron/Zofran®, palonsetron/Aloxi®) and/or substance P inhibitors (e.g., aprepitant/Emend®); immunosuppression can be treated with a blood transfusion; infection and/or sepsis can be treated with antibiotics (e.g., penicillins, tetracyclines, cephalosporins, sulfonamides, aminoglycosides, etc.); and so forth.

In some embodiments, inventive compositions may be administered and/or inventive diagnostic methods may be performed in combination with any therapeutic agent or therapeutic regimen that is useful to diagnose one or more symptoms or features of cancer (e.g., detect the presence of and/or locate a tumor). In some embodiments, inventive conjugates may be used in combination with one or more other diagnostic agents. To give but one example, conjugates used to detect tumors may be administered in combination with other agents useful in the detection of tumors. For example, inventive conjugates may be administered in combination with traditional tissue biopsy followed by immunohistochemical staining and serological tests (e.g., prostate serum antigen test). Alternatively or additionally, inventive conjugates may be administered in combination with a contrasting agent for use in computed tomography (CT) scans and/or MRI.

Methods of Preparing and Synthesizing Bifunctional Stapled or Stitched Peptides

In certain embodiments, the targeting and effector domains A and E of the bifunctional stapled or stitched peptides of the invention are designed and synthesized de novo. In certain embodiments, the targeting and effector domains A and E comprise one or more non-natural amino acids (Tables 1 and 2). In certain embodiments, the targeting and effector domains A and E can be stapled or stitched, as described herein, by crosslinking moieties to stabilize the secondary structure of the A and E domains.

In general, the synthesis of these stabilized secondary structures involves (1) synthesizing a peptide from a selected number of natural or non-natural amino acids, wherein said peptide comprises at least two reactive moieties capable of undergoing a C—C bond forming reaction; and (2) contacting said peptide with a reagent to generate at least one crosslinker and to effect stabilization of a specific secondary structure motif (e.g., an α-helix).

As one of ordinary skill in the art will realize, the number, stereochemistry, and type of amino acid structures (natural or non-natural) selected will depend upon the size and shape of the secondary structure to be prepared (e.g., length of an α-helix), the ability of the particular amino acids to generate a secondary structural motif that are desirable to mimic. The secondary structure to be prepared depends on the desired biological activity, that is the ability to target an effector biomolecule or a target biomolecule with an affinity sufficient to be specific and to follow the two biomolecules together.

It will be appreciated, that the number of crosslinking moieties is not limited to one or two, rather the number of crosslinking moieties utilized can be varied with the length of the targeting and/or effector domain as desired, and as compatible with the desired structure and activity to be generated.

The synthesis of an inventive bifunctional polypeptide first involves the selection of a desired sequence and number of amino acids and amino acid analogues. As one of ordinary skill in the art will realize, the number, stereochemistry, and type of amino acid structures (natural or non-natural) selected will depend upon the size of the polypeptide to be prepared, the ability of the particular amino acids to generate a desired structural motif (e.g., an alpha-helix), and any particular motifs that are desirable to mimic to generate protein domains that effectively bind to the target or effector biomolecule.

Once the amino acids are selected, synthesis of the inventive polypeptide can be achieved using standard deprotection and coupling reactions. Formation of peptide bonds and polypeptide synthesis are techniques well-known to one skilled in the art, and encompass both solid phase and solution phase methods; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis,* 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, *Bioorganic chemistry: Peptides and Proteins*, Hecht, Oxford University Press, New York: 1998, the entire contents of which are incorporated herein by reference.

In certain embodiments, the method comprises a solution phase synthesis of an inventive bifunctional polypeptide. Solution phase synthesis, as mentioned above, is a well-known technique for the construction of polypeptides. An exemplary solution phase synthesis comprises the steps of: (1) providing an amino acid protected at the N-terminus with a suitable amino protecting group; (2) providing an amino acid protected at the C-terminus with a suitable carboxylic acid protecting group; (3) coupling the N-protected amino acid to the C-protected amino acid; (4) deprotecting the product of the coupling reaction; and (5) repeating steps (3) to (4) until a desired polypeptide is obtained, wherein at least two of the amino acids coupled at any of the above steps each comprise at least one terminally unsaturated amino acid side chain, and at least one α,α-disubstituted amino acid comprises two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

In certain embodiments, the method comprises a solid phase synthesis of an inventive bifunctional polypeptide or portion thereof. Solid phase synthesis, as mentioned above, is a well-known technique for the construction of polypeptides. An exemplary solid phase synthesis comprises the steps of: (1) providing a resin-bound amino acid; (2) deprotecting the resin bound amino acid; (3) coupling an amino acid to the deprotected resin-bound amino acid; (4) repeating steps (3) until a desired peptide is obtained, wherein at least two of the amino acids coupled at any of the above steps each comprise at least one terminally unsaturated amino acid side chain, and at least one α,α-disubstituted amino acid comprises two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

After a desired polypeptide is synthesized using an appropriate technique, the polypeptide is contacted with a specific catalyst to promote "stapling" or "stitching" of the polypeptide. For example, the resin-bound polypeptide may be contacted with a catalyst to promote "stapling" or "stitching," or may first be cleaved from the resin, and then contacted with a catalyst to promote "stitching."

Different amino acids have different propensities for forming different secondary structures. For example, methionine (M), alanine (A), leucine (L), glutamate (E), and lysine (K) all have especially high alpha-helix forming propensities. In contrast, proline (P) and glycine (G) are alpha-helix disruptors.

In certain embodiments, the one or more reaction steps further comprise the use of a coupling reagent. Exemplary coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethyllaminopropyl)carbodiimide (EDC), N,N'-carbonyldiimidazole (CDI), 3-(diethoxyphosphoryloxy)-1,2,3-benzotriazin-4(3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl) uranium tetrafluoroborate (TDBTU), and O—(N-succinimidyl)-1,1,3,3-tetramethyl uranium tetrafluoroborate (TSTU)).

In certain embodiments, the above reaction of step (iv) further comprises a suitable base. Suitable bases include, but are not limited to, potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo [5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine ($NEt_3$).

In certain embodiments, one or more reaction steps are carried out in a suitable medium. A suitable medium is a solvent or a solvent mixture that, in combination with the combined reacting partners and reagents, facilitates the progress of the reaction there between. A suitable solvent may solubilize one or more of the reaction components, or, alternatively, the suitable solvent may facilitate the suspension of one or more of the reaction components; see generally, *March's Advanced Organic Chemistry: Reactions, Mechanisms, and Structure*, M. B. Smith and J. March, $5^{th}$ Edition, John Wiley & Sons, 2001, and *Comprehensive Organic Transformations*, R. C. Larock, $2^{nd}$ Edition, John Wiley & Sons, 1999, the entire contents of each of which are incorporated herein by reference. Suitable solvents for include ethers, halogenated hydrocarbons, aromatic solvents, polar aprotic solvents, or mixtures thereof. In other embodiments, the solvent is diethyl ether, dioxane, tetrahydrofuran (THF), dichloromethane (DCM), dichloroethane (DCE), acetonitrile (ACN), chloroform, toluene, benzene, dimethylformamide (DMF), dimethylacetamide (DMA), dimethylsulfoxide (DMSO), N-methylpyrrolidinone (NMP), or mixtures thereof.

In other embodiments, one or more reaction steps are conducted at suitable temperature, such as between about 0° C. and about 100° C.

In certain embodiments, one or more reaction steps involve a catalyst. One of ordinary skill in the art will realize that a variety of catalysts can be utilized. Selection of a particular catalyst will vary with the reaction conditions utilized and the functional groups present in the particular peptide. In certain embodiments, the catalyst is a ring closing metathesis (RCM) catalyst. In certain embodiments, the RCM catalyst is a tungsten (W), molybdenum (Mo), or ruthenium (Ru) catalyst. In certain embodiments, the RCM catalyst is a ruthenuim catalyst. Suitable RCM catalysts are described in see Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem.* Soc. (1999) 121:9453; and *Chem. Eur. J.* (2001) 7:5299; the entire contents of each of which are incorporated herein by reference.

In certain embodiments, the RCM catalyst is a Schrock catalyst, a Grubbs catalyst, a Grubbs-Hoveyda catalyst, a Blechart Catalyst; a Neolyst™ Ml; or a Furstner catalyst.

It will also be appreciated, that in addition to RCM catalysts, other reagents capable of promoting carbon-carbon bond formation can also be utilized. For example, other reactions that can be utilized, include, but are not limited to palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi (Furstner et al., *J. Am. Chem. Soc.* 1996, 118, 12349)) coupling reactions. Thus, the appropriate reactive moieties are first incorporated into desired amino acids or unnatural amino acids, and then the peptide is subjected to reaction conditions to effect "stapling" or "stitching" and subsequent stabilization of a desired secondary structure.

In another aspect, the present invention provides a method of synthesizing an inventive polypeptide comprising the steps of: (1) providing a selected number of amino acids comprising (i) at least two amino acids, each comprising at least one terminally unsaturated amino acid side chain, and (ii) at least one α,α-disubstituted amino acid comprising two terminally unsaturated amino acid side chains; (2) coupling the selected number of amino acids together to generate a first peptide; and (3) treating the first peptide with a suitable catalyst to provide a stapled or stitched peptide.

In certain embodiments, divinyl amino acid as "an α,α-disubstituted amino acid comprising two terminally unsaturated amino acid side chains" is specifically excluded.

In certain embodiments, each terminally unsaturated amino acid side chain is reactive toward ring closing metathesis. In certain embodiments, the suitable catalyst is a ring metathesis catalyst. In certain embodiments, the ring closing metathesis catalyst may generate at least two cross-linked rings by the above method. Depending upon the nature of the selected amino acids and their specific location in the peptide chain, stitched peptides of the present invention may comprise at least 2, 3, 4, 5, 6, or 7, cross-links, and may comprise one or more constitutional/structural isomers (i.e., compounds with the same molecular weight but having different connectivity).

In certain embodiments, the synthetic method generates one stitched product as a preferred product. As used herein a "preferred product" refers to one constitutional isomer present as the major constituent in a mixture of isomers. In certain embodiments, a "preferred product" refers to one constitutional isomer present as a component in at least about 50%, 55%, 60%, 65%, 70%, 75%, 80%, 85%, 90%, 95%, 98%, or 99%, of an isomeric mixture.

The synthetic method may be further modified to include at least three cross-linking staples by: (1) providing a selected number of natural or unnatural amino acids, wherein said number comprises: (i) at least four amino acids, each comprising at least one terminally unsaturated amino acid side chain, and (ii) at least one α,α-disubstituted amino acid comprising two terminally unsaturated amino acid side chains; (2) coupling the selected number of amino acids together to generate a first peptide; and (3) treating the first peptide with a suitable catalyst.

Additionally, the synthetic method may be modified to include at least three cross-linking staples by: (1) providing a selected number of natural or unnatural amino acids, wherein said number comprises: (i) at least two amino acids, each comprising at least one terminally unsaturated amino acid side chain, and (ii) at least two α,α-disubstituted amino acids, each comprising two terminally unsaturated amino acid side chains; (2) coupling the selected number of amino acids together to generate a first peptide; and (3) treating the first peptide with a suitable catalyst.

The present invention contemplates any and all types of modifications in order to provide at least 2, 3, 4, 5, 6, or 7, cross-linked staples into the polypeptides of the invention.

The above amino acids comprising one to two terminally unsaturated amino acid side chains are so incorporated into the polypeptide chain in order to provide proximal terminally unsaturated side chains. These proximal terminally unsaturated side chains may be in the same plane as, or same side of the polypeptide chain as, each other in any given conformation of the polypeptide. Upon treatment with a suitable catalyst, these proximal side chains react with each other via "stapling" to provide a stitched, conformationally stabilized, polypeptide. In certain embodiments, the proximal terminally unsaturated side chains are arranged such that the resulting "staple" does not interfere with the biological/therapeutic activity of the stitched polypeptide.

Additional Synthetic Modifications

After "stitching" of the polypeptide, as described above, the method may further comprise additional synthetic modification(s). Any chemical or biological modification may be made. In certain embodiments, such modifications include reduction, oxidation, and nucleophilc or electrophilic additions to a functional group (e.g., a double bond provided from a metathesis reaction) of the cross-link to provide a synthetically modified stitched polypeptide. Other modifications may include conjugation of a stitched polypeptide, or a synthetically modified stitched polypeptide, with a biologically active agent, label or diagnostic agent anywhere on the stitched polypeptide scaffold, e.g., such as at the N-terminus of the stitched polypeptide, the C-terminus of the stitched polypeptide, on an amino acid side chain of the stitched polypeptide, or at one or more modified or unmodified stitched sites (i.e., to a staple). Such modification may be useful in delivery of the peptide or biologically active agent to a cell, tissue, or organ. Such modifications may allow for targeting to a particular type of cell or tissue.

Thus, in certain embodiments, the above synthetic method further comprises: (vii) treating the polypeptide with a suitably reactive agent under suitable conditions to provide a synthetically modified stitched polypeptide.

One of ordinary skill in the art will appreciate that a wide variety of reactions, conditions, and "suitably reactive agent(s)" may be employed to promote such a transformation, therefore, a wide variety of reactions, conditions, and reactive agents are envisioned; see generally, *March's Advanced Organic Chemistry: Reactions, Mechanisms, and Structure*, M. B. Smith and J. March, 5$^{th}$ Edition, John Wiley & Sons, 2001; *Advanced Organic Chemistry, Part B: Reactions and Synthesis*, Carey and Sundberg, 3$^{rd}$ Edition, Plenum Press, New York, 1993; and *Comprehensive Organic Transformations*, R. C. Larock, 2$^{nd}$ Edition, John Wiley & Sons, 1999, the entirety of each of which is hereby incorporated herein by reference. Exemplary "suitably reactive agents" may be any agent reactive with a multiple bond (e.g., a double or triple bond). In certain embodiments, suitably reactive agents are able to react with a double bond or triple bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond or double bond. As one of ordinary skill in the art will clearly recognize, these above-described transformations will introduce functionalities compatible with the particular stabilized structures and the desired biological interactions; such functionalities include, but are not limited to, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

In another aspect, in certain embodiments, the method further comprises treating the polypeptide with a suitably reactive agent to provide a synthetically modified stitched polypeptide, and treating the modified stitched polypeptide with a biologically active agent to provide a modified stitched polypeptide conjugated to a biologically-active agent.

In another aspect, in certain embodiments, the above method further comprises treating the polypeptide with a suitable reagent to provide a synthetically modified stitched polypeptide, and treating the modified stitched polypeptide with a diagnostic agent to provide a modified stitched polypeptide conjugated to a diagnostic agent.

Conjugation of an agent (e.g., a label, a diagnostic agent, a biologically active agent) to the inventive polypeptide may be achieved in a variety of different ways. The agent may be covalently conjugated, directly or indirectly, to the polypeptide at the site of stapling, or to the N-terminus or the C-terminus of the polypeptide chain. Alternatively, the agent may be noncovalently conjugated, directly or indirectly, to the polypeptide at the site of stapling, or to the N-terminus or the C-terminus of the polypeptide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or noncovalent linking group.

Any suitable bond may be used in the conjugation of a biologically active agent and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological conditions (e.g., enzymatically cleavable, cleavable with a high or low pH, with heat, light, ultrasound, x-ray, etc.). However, in some embodiments, the bond is not cleavable.

Combinatorial Synthesis of Novel Stapled or Stitched Polypeptides

It will also be appreciated by one of ordinary skill in the art that the synthetic methods as described above can also be applied to combinatorial synthesis of stapled or stitched polypeptides. Although combinatorial synthesis techniques can be applied in solution, it is more typical that combinatorial techniques are performed on the solid phase using split-and-pool techniques. During the course of the combinatorial synthesis, various parameters can be varied, including, but not limited to, placement of amino acids with terminally unsaturated side chains, stereochemistry of amino acids, terminally unsaturated side chain length and functionality, and amino acid residues utilized.

The present invention, in one aspect, provides methods for the synthesis of libraries of stapled or stitched polypeptides, as described above, comprising (1) providing a collection of resin-bound amino acids; (2) deprotecting each of said resin bound amino acids; (3) separating said collection of deprotected resin bound amino acids into n equal portions, wherein n represents the number of different types of amino acids to be coupled; (4) coupling of each of n types of amino acids to the deprotected amino acid; (5) combining each of the n portions together; and (6) repeating steps (2)-(5) until a desired polypeptide is obtained, wherein at least two of the amino acids coupled at any of the above steps each comprise at least one terminally unsaturated amino acid side chain, and at least one α,α-disubstituted amino acid comprises two terminally unsaturated amino acid side chains. After a desired polypeptide is synthesized, the resin-bound polypeptide may be contacted with a catalyst to promote "stitching," or may first be cleaved from the resin, and then contacted with a catalyst to promote "stitching."

It will be appreciated by one of ordinary skill in the art that the libraries of compounds having stabilized secondary structures can be further diversified at specific functional moieties after the desired stabilized structures are formed. For example, free or latent amino acid functionalities may be diversified, or alternatively or additionally, free or latent functionality present on the cross-linkers may be diversified. In particularly preferred embodiments, in but one example, the hydrophilicity of stabilized structures may be increased by the introduction of hydroxyl moieties. As one of ordinary skill in the art will realize, the diversification reactions will be selected to introduce functionalities compatible with the particular stabilized structures and the desired biological interactions, and these functionalities include, but are not limited to hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol; halo; cyano; nitro; azido; imino; oxo; and thiooxo.

The targeting and effector domains A and E of the bifunctional stapled peptides of the invention can be designed by any method known in the art. For example, A and B can be designed according to known binding or interaction domains from the literature. Many interaction domains for well characterized viral and cellular oncogenes (e.g., c-Myc, Ras), tumor suppressors (e.g., p53, Rb), transcription factors (e.g., HIF, E2F), modifying enzymes (e.g., ubiquitin ligases, acetylases, phosphorylases, methylases), structural proteins, signaling receptors and signaling pathway molecules (e.g., beta-catenin), growth factors (e.g., EGFR) are known in the art.

Effector domains can be designed, for example, for binding to and recruitment of co-repressor proteins such as Groucho/TLE1, SHARP, NCoR, NCoR2, SMRT, BCoR or others. For example, the engrailed homology (Eh1) domains that are found in transcription factors and are known to be essential and sufficient for recruiting Groucho/TLE1 co-repressors to target promoters may serve to design the effector domain.

In another embodiment, the amphipathic alpha-helix of Mad1 that binds and retains the Sin-3 repressive complex through its PAH domain may be used to design the effector domain. In another embodiment, the effector domain (E) is designed according to the FXXFF motif capable of binding and recruiting MDM2 or MDMX or according to the p53 activation domain 1 (Ac-LSQETFSDLWKLLPE-$CONH_2$ (SEQ ID NO:35)).

In another embodiment, the effector domain (E) is designed to bind and recruit molecules belonging to the nuclear export machinery, such as exportins, e.g. CRM1.

In another embodiment, the effector domain (E) is designed as a signal peptide or small molecule comprising or mimicking a nuclear localization sequence (NLS) to bind nuclear import proteins, e.g. NLS sequences that are known to target and bind Imp$\alpha$. Examples of NLS sequences are SV40 T-antigen: Ac-PKKKRKVE-$CONH_2$ (SEQ ID NO:42); Nucleoplasmin: Ac-KRPAATKK-AGQAKKKKLD-$CONH_2$ (SEQ ID NO:43); and c-Myc: Ac-PAAKRVKLD-$CONH_2$ (SEQ ID NO:44) (Gorlich D and Kutay U. *Annu. Rev. Cell Dev. Biol.* 1999, 15: 607-60).

In another embodiment, the effector domain (E) is designed as a peptide or small molecule capable of binding and recruiting specific transcriptional co-activator proteins or components of the basal transcriptional apparatus, for example, TAFII proteins or RNA polymerases or an effector domain according to the KIX domain of CBP/p300 that has two distinct binding sites targeted by transcription factors to localize and retain the co-activator protein. These domains may include p53 AD1: Ac-LSQETFSDLWKLLPE-$CONH_2$ (SEQ ID NO:45); p53 AD2: Ac-MLSPDDIEQWFTEDPG-$CONH_2$ (SEQ ID NO:46); MLL: Ac-ILPSDIMDFVLKNTP-$CONH_2$ (SEQ ID NO:47); c-Jun: Ac-LASPELERLIIQSSN-$CONH_2$ (SEQ ID NO:48); HLTV-TAX: Ac-YIDGFVIGSALQFLIPRLP-$CONH_2$ (SEQ ID NO:49); c-MYB: Ac-KEKRIKELELLLMSTENELKG-$CONH_2$ (SEQ ID NO:50); pKID: Ac-ILSRRPSYRKILNDLSS-DAPG-$CONH_2$ (SEQ ID NO:51), or derived from p-KID, where any serine residues, in particular Ser133, can be found phosphorylated, as is present in the native pKID:KIX interaction.

In another embodiment, the effector domain (E) is designed comprising peptides or small molecules capable of binding and recruiting specific post-translational modifying enzymes or complexes including kinases, acetyltransferases, phosphatases, glycotransferases, lipid transferases and others to alter transcription factor function.

In another embodiment, the targeting domain is designed according to a transcription factor targeting ligand, such as SAHM1, capable of binding the Notch:CSL transcription factor complex.

High affinity targeting and effector domains (A and E) can also be designed rationally according to available crystallographic data or data derived from published affinity screens, such as phage display.

The targeting and effector domains A and E of the bifunctional stapled peptides of the invention can be obtained for any protein that is desired using, for example, high throughput affinity screens. For example, the targeting domains can be designed to associate or bind to any candidate oncogene, tumor suppressor, transcription factor, such as the NF-kappaB and AP-1 families of transcription factors, the STAT family members, the steroids receptors, Ets factors, ATF family members, basic helix-loop-helix transcription factors, telomerases, growth factors, and growth factor receptors. These factors might be, for example, misfunctional, mislocalized, deregulated, ectopically active, inactive, or misfolded and may contribute to cellular transformation, changes in cell fate, de-differentiation, apoptosis, necrosis, ectopic cell signaling or other changes that cause a disease state in a subject. These candidate proteins associated with one targeting domain of the bifunctional stapled peptides of the invention can then be tethered to an effector biomolecule, as described herein, such as ubiquitin ligases, DUBs, acetylases, deacetylases, kinases phosphatases, methylases, demethylases, glycosyltransferases, glycosidases, or chaperones. The targeting and effector domains can, in certain embodiments, be substantially similar to or homologous with a known bioactive polypeptide, e.g., a polypeptide that is known to bind or associate with a target biomolecule or effector biomolecule.

Figure 15:
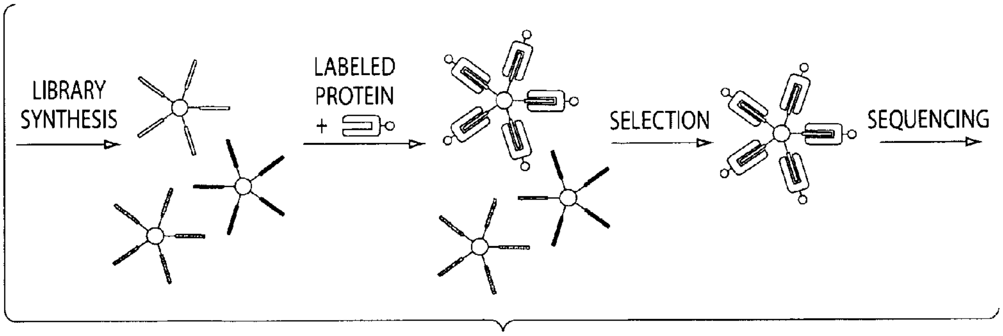
FIG. 15 depicts an example of a screening procedure for high affinity binding of synthetic libraries of stapled peptides to targets.
Figure 16:
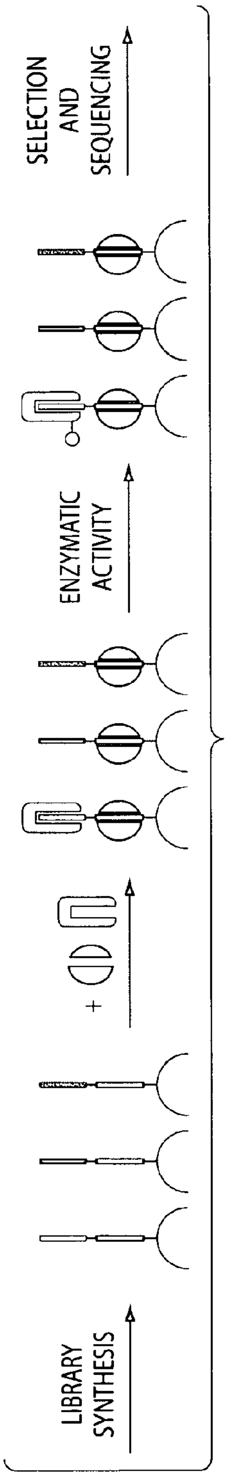
FIG. 16 depicts an example of a screening procedure for high affinity binding of synthetic libraries of stapled peptides to targets. The screening procedure includes the detection of a modification of a second protein as a criterion for selection.

In certain embodiments, the targeting and effector domains A and E comprising one or more non-natural amino acids and/or one or more cross-linking moieties are selected for high binding affinity and binding specificity as well as activity using any high throughput affinity screens know in the art, such as phage display, or as described in FIGS. 15 and 16.

In certain embodiments, the targeting and effector domains A and E are covalently associated by a linker L. This linker can have any length or other characteristic and minimally comprises two reactive terminal groups that can chemically interact with (and covalently bind to) the polypeptide chains of targeting and effector domains A and E.

In some embodiments, the linker L can comprise natural or non-natural amino acids and/or may comprise other molecules with terminal reactive groups. For example, linkers may comprise PEG (polyethylene glycol) and NHS or maleimide reactive terminal groups, such as, $SM(PEG)_n$ Succinimidyl-([N-maleimidopropionamido]-n-ethyleneglycol). It will be appreciated that the length of the linker L is variable and can be designed based on the required flexibility or rigidity necessary to link the targeting and effector domains A and E, respectively. Examples of covalent conjugation strategies and suitable reaction conditions using a variety of linkers and/or functional groups to associate polypeptide A with polypeptide E are set forth in FIGS. 27 to 32. In certain embodiments, thiol-maleimide conjugates are generated. In other embodiments, 1,4- or 1,5-triazole conjugates are generated from the reaction of an azide with an alkyne.

The distance of the targeting and effector domains A and E can be varied by the length of linker L based on several parameters, including, but not limited to: 1) the molecular size of the respective target biomolecule and effector biomolecule, and/or 2) the relative molecular distance between the catalytic site of the effector biomolecule and the site of modification on the target biomolecule, and/or 3) the relative distance of the sites on the effector biomolecule and the target biomolecule that are bound by the targeting domains A and E, and/or 4) cell permeability of the bifunctional stapled peptide, and/or 5) bioavailability of the bifunctional stapled peptide, and/or 6) stability of the bifunctional stapled peptide, and/or other structural or chemical considerations.

EXAMPLES

Example 1

Figure 2:
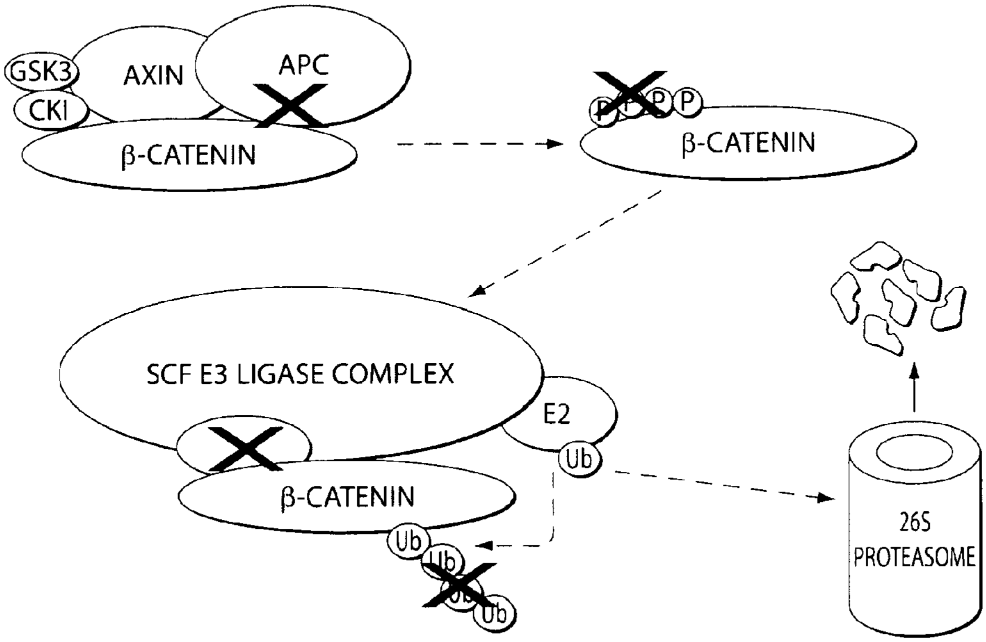
FIG. 2 shows the loss of endogenous β-catenin degradation in human cancers.

Bifunctional Stapled Peptide for Degradation of β-Catenin

β-catenin is an essential component of the Wnt signaling pathway. The canonical Wnt pathway plays critical roles in embryonic development, stem cell growth, and tumorigenesis. Stimulation of the Wnt pathway leads to the association of O-catenin with Tcf and BCL9 in the nucleus, resulting in the transactivation of Wnt target genes. The level of β-catenin in the cytosol is regulated by β-catenin destruction complex. In the absence of a Wnt signal, β-catenin is phosphorylated, leading to its ubiquitination by the SCF E3 ubiquitin ligase complex and subsequent degradation by the 26S proteasome (FIG. 1). In the presence of a Wnt signal, the destruction complex is inhibited and cytosolic levels of β-catenin rise, allowing its translocation to the nucleus where β-catenin interacts with Tcf and other transcription factors to activate target genes. Genetic aberrations in components of this pathway are associated with a variety of cancers [Barker and Clevers, *NRDD,* 5, 998-1014 (2006)]. Because most colon cancers are caused by an excess accumulation of β-catenin, the Wnt signaling pathway might be a good target for the development of Wnt signaling inhibitors for cancer treatment. The molecular structure of β-catenin has been resolved [Sampietro et al., *Mol. Cell.* 24, 293-300 (2006)]. The sites of interaction of β-catenin with the transcriptional co-activator Bcl9 and the DNA-binding transactivator Tcf-4 have been identified and resolved as a triple complex in a crystal structure [Sampietro et al., *Mol. Cell.* 24, 293-300 (2006)]. For example, the BCL9 β-catenin binding domain (CBD) forms an a helix that binds to the first armadillo repeat of β-catenin. In many cancers, mutations of proteins involved in β-catenin ubiquitination and degradation are frequently found, resulting in aberrant levels of β-catenin (FIG. 2). For example, most colorectal cancers have mutations of the adenomatous polyposis coli (APC) gene or the beta-catenin gene that stabilize beta-catenin and activate beta-catenin target genes leading to cancer.

Figure 3:
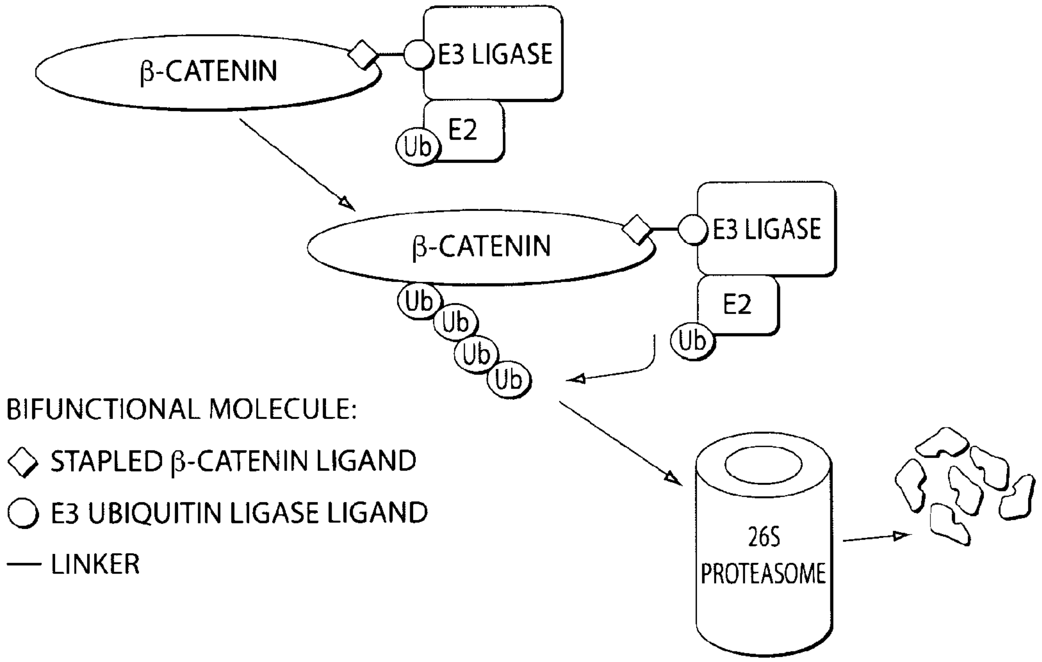
FIG. 3 depicts restoration of β-catenin destruction using a bifunctional stapled peptide.
Figure 4:
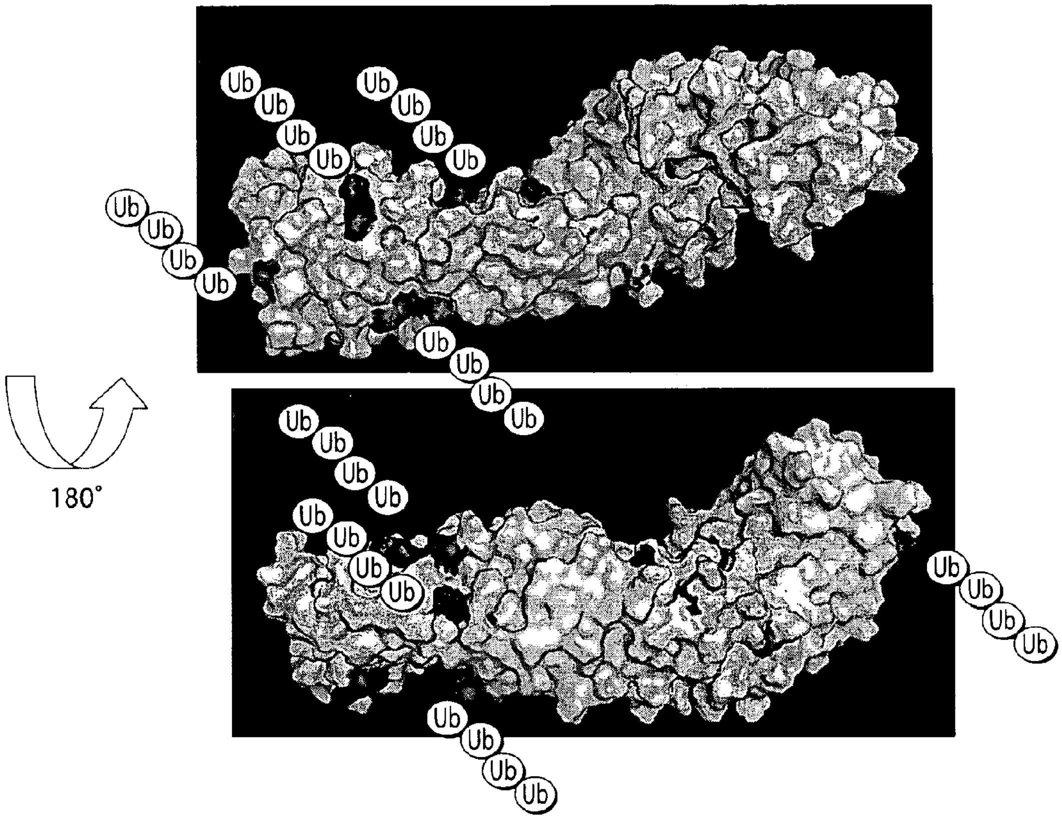
FIG. 4 shows surface exposed lysines on the β-catenin Arm repeat domain that are putative sites for ubiquitination.

Bifunctional stapled peptides are used to restore β-catenin destruction through polyubiquitination in cancer cells that harbor mutations in the β-catenin destruction pathway (for example mutated or truncated adenomatous polyposis coli, APC). The bifunctional stapled peptides have two moieties, a targeting and an effector domain. The targeting domain is a β-catenin binding moiety and the effector domain is a E3 ubiquitin ligase recruiting moiety. The E3 ubiquitin ligase binding moiety recruits E3 ubiquitin ligase in proximity to β-catenin and thereby facilitates β-catenin polyubiquitination (FIG. 3). There are several surface exposed lysine residues in the Arm-domain of β-catenin (FIG. 4).

Suitable bifunctional stapled peptides are transfected in vitro into cancer cells, for example colon cancer cells (SW480, DLD-1, and HT29, HCT-116), breast cancer cells (MCF7), or prostate cancer cells (PC3, LNCAP), and transfected cells are screened by western blot analysis for a reduction of soluble and/or membrane-bound (cytosolic and/or nuclear) β-catenin protein levels or appearance of poly-ubiquitinated forms of β-catenin, and using reporter assays (e.g., luciferase) to detect down-regulation of co-transfected LEF/TCF target genes. Cellular distribution of β-catenin (nuclear, cytosolic) is followed by immunofluorescence, using β-catenin specific antibodies and standard staining protocols. As a positive control, CELECOXIB is used.

Figure 5:
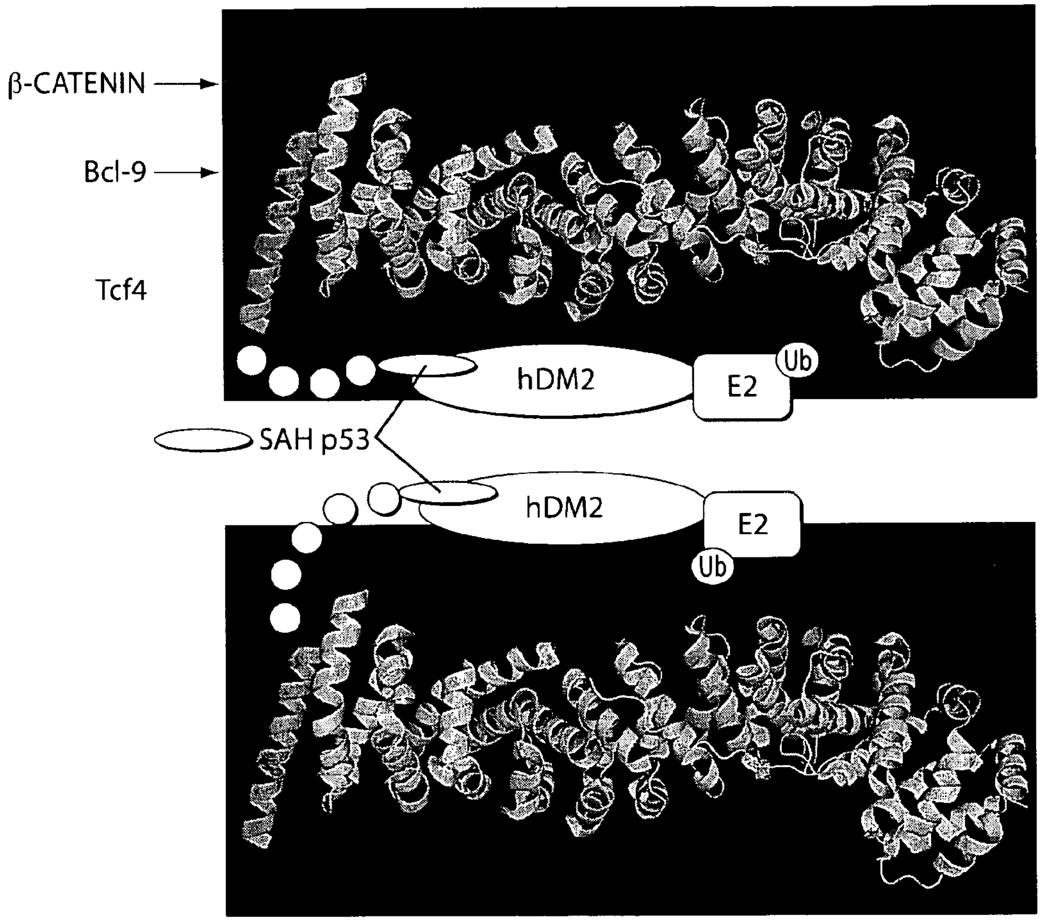
FIG. 5 shows an example of a bifunctional stapled peptide based on Bcl9 and p53 that can bring hDM2 in close proximity to O-catenin to effect ubiquitination.
Figure 6:
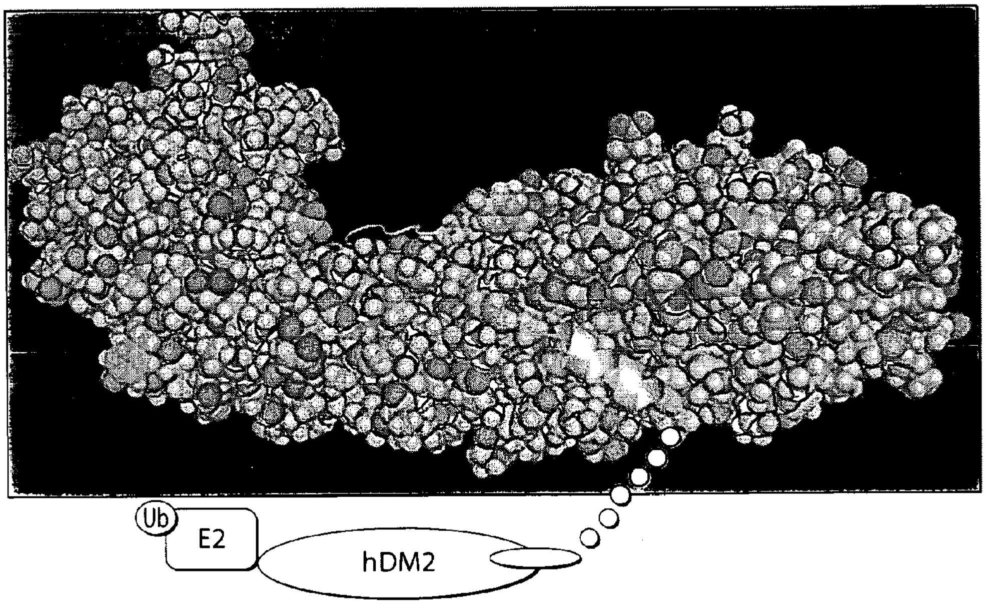
FIG. 6 shows an example of a bifunctional stapled peptide based on Tcf4 and p53 that can bring hDM2 in close proximity to β-catenin to effect ubiquitination.

Several bifunctional stapled peptides are tested for their ability to restore polyubiquitination of β-catenin: Bcl 9-SAH p53-8 and Tcf-4-SAH p53. hDM2 is a E3 ligase well known to promote p53 degradation via ubiquitination. A stapled peptide SAHp53 was previously synthesized as a dominant negative that binds to hDM2. The SAHp53-8 is used as the E3 ligase recruiting moiety (effector domain) to bring hDM2 in proximity to β-catenin. Bcl-9 and Tcf4 peptides possess α-helical structure that can be stapled. The Bcl-9 or Tcf4 peptides are fused with SAH p53-8. The resulting bifunctional peptide bridges β-catenin and hDM2 and thereby facilitates β-catenin ubiquitination (FIGS. 5 and 6).

Bifunctional stapled peptides with different orientations are produced. In the design of bifunctional stapled peptides, SAH p53-8 is placed at either N- or the C-terminus (FIG. 7). Peptides are then screened to select the optimal orientation. The following bifunctional peptides are synthesized:

Group 1: SAH p53-8- Bcl 9

(SEQ ID NO: 1)
$QSQQTFR_8NLWRLLS_5QN-(Ahx)_n-SQEQLR_8HRERSLS_5TLRDIQRMLF$ (SEQ ID NO: 2)
$QSQQTFR_8NLWRLLS^5QN-(Ahx)_n-SQEQLEHRERSLS_5TLRS_5IQRMLF$ (SEQ ID NO: 3)
$QSQQTFR_8NLWRLLS_5QN-(Ahx)_n-SQEQLEHRS_5RSLS_5TLRDIQRMLF$
n = 2-4, Ahx: aminohexanoic acid Group 2: Bcl 9- SAH p53-8

(SEQ ID NO: 4)
$SQEQLR_8HRERSLS_5TLRDIQRMLF-(Ahx)_n-QSQQTFR_8NLWRLLS_5QN$ (SEQ ID NO: 5)
$SQEQLEHRERSLS_5TLRS_5IQRMLF-(Ahx)_n-QSQQTFR_8NLWRLLS_5QN$ (SEQ ID NO: 6)
$SQEQLEHRS_5RSLS_5TLRDIQRMLF-(Ahx)_n-QSQQTFR_8NLWRLLS_5QN$
n = 2-4, Ahx: aminohexanoic acid Group 3: SAH p53-8- Bcl 9

(SEQ ID NO: 7)
$QSQQTFR_8NLWRLLS_5QN-(PEG)_n-SQEQLR_8HRERSLS_5TLRDIQRMLF$

```
                                                     (SEQ ID NO: 8)
QSQQTFR₈NLWRLLS₅QN-(PEG)ₙ-SQEQLEHRERSLS₅TLRS₅IQRMLF

                                                     (SEQ ID NO: 9)
QSQQTFR₈NLWRLLS₅QN-(PEG)ₙ-SQEQLEHRS₅RSLS₅TLRDIQRMLF
n = 2-4, PEG: Polyethyleneglycol

Group 4: Bcl 9- SAH p53-8
                                                    (SEQ ID NO: 10)
SQEQLR₈HRERSLS₅TLRDIQRMLF-(PEG)ₙ-QSQQTFR₈NLWRLLS₅QN

                                                    (SEQ ID NO: 11)
SQEQLEHRERSLS₅TLRS₅IQRMLF-(PEG)ₙ-QSQQTFR₈NLWRLLS₅QN

                                                    (SEQ ID NO: 12)
SQEQLEHRS₅RSLS₅TLRDIQRMLF-(PEG)ₙ-QSQQTFR₈NLWRLLS₅QN
n = 2-4, PEG: Polyethyleneglycol
```

Figure 9:
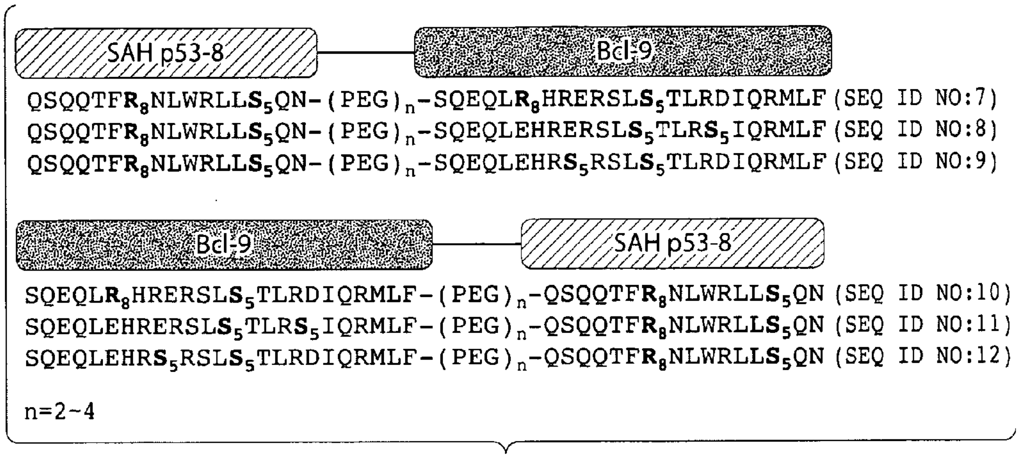
FIG. 9 depicts example sequences of bifunctional stapled peptides SAH p53-8-Bcl-9 (SEQ ID NO: 7-9) and Bcl-9-SAH p53-8 (SEQ ID NO: 10-12) with PEG linker.

Aminohexanoic acid (Ahx) or polyethyleneglycol (PEG) ranging from 2-4 residues is used as a linker to connect the two stapled peptides (FIGS. 8 and 9). The optimal length of the Ahx linker is determined empirically based on biochemical as well as cell based assays.

```
Group 5: SAH p53-8- Tcf-4
                                                    (SEQ ID NO: 13)
QSQQTFR₈NLWRLLS₅QN-(Ahx)ₙ-DELISFKDEGEQE(β-Ala)₂ERDLS₅DVKS₅SLVN

                                                    (SEQ ID NO: 14)
QSQQTFR₈NLWRLLS₅QN-(Ahx)ₙ-DELISFKDEGEQE(β-Ala)₂ER₈DLADVKS₅SLVN
n = 2-4, Ahx: aminohexanoic acid, β-Ala: β-Alanine

Group 6: Tcf-4- SAH p53-8
                                                    (SEQ ID NO: 15)
DELISFKDEGEQE(β-Ala)₂ERDLS₅DVKS₅SLVN-(Ahx)ₙ-QSQQTFR₈NLWRLLS₅QN

                                                    (SEQ ID NO: 16)
DELISFKDEGEQE(β-Ala)₂ER₈DLADVKS₅SLVN-(Ahx)ₙ-QSQQTFR₈NLWRLLS₅QN
n = 2-4, Ahx: aminohexanoic acid, β-Ala: β-Alanine

Group 7: SAH p53-8- Tcf-4
                                                    (SEQ ID NO: 17)
QSQQTFR₈NLWRLLS₅QN-(PEG)ₙ-DELISFKDEGEQE(β-Ala)₂ERDLS₅DVKS₅SLVN

                                                    (SEQ ID NO: 18)
QSQQTFR₈NLWRLLS₅QN-(PEG)ₙ-DELISFKDEGEQE(β-Ala)₂ER₈DLADVKS₅SLVN

Group 8: Tcf-4- SAH p53-8
                                                    (SEQ ID NO: 19)
DELISFKDEGEQE(β-Ala)₂ERDLS₅DVKS₅SLVN-(PEG)ₙ-QSQQTFR₈NLWRLLS₅QN

                                                    (SEQ ID NO: 20)
DELISFKDEGEQE(β-Ala)₂ER₈DLADVKS₅SLVN-(PEG)ₙ-QSQQTFR₈NLWRLLS₅QN
```

Figure 10:
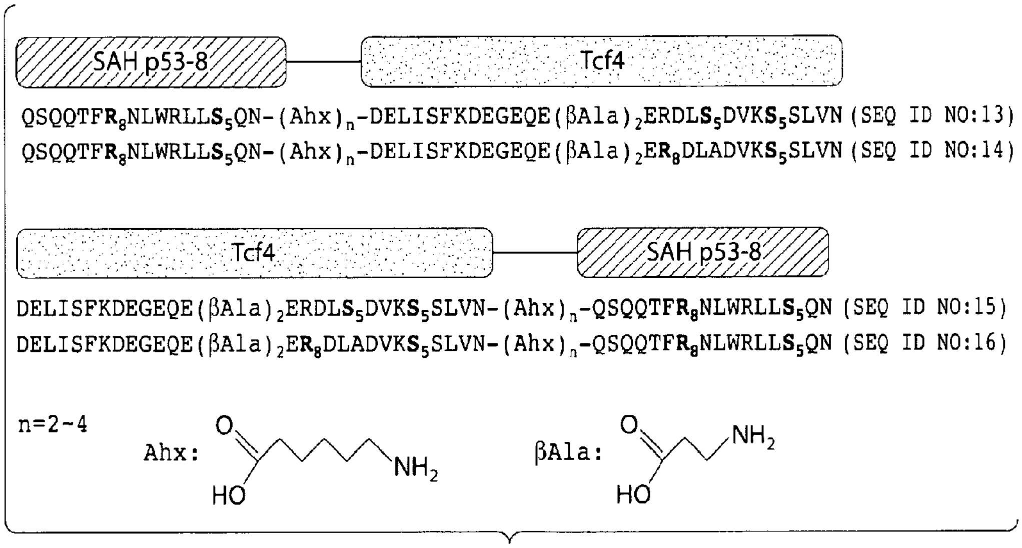
FIG. 10 depicts example sequences of bifunctional stapled peptides SAH p53-8-Tcf4 (SEQ ID NO: 13, 14) and Tcf4-SAH p53-8 (SEQ ID NO: 15, 16) with Ahx linker.

Aminohexanoic acid (Ahx) or polyethyleneglycol (PEG) ranging from 2-4 residues is used as a linker to connect the two stapled peptides (FIGS. 10 and 11). The optimal length of the Ahx linker is determined empirically based on biochemical as well as cell based assays.

Figure 14:
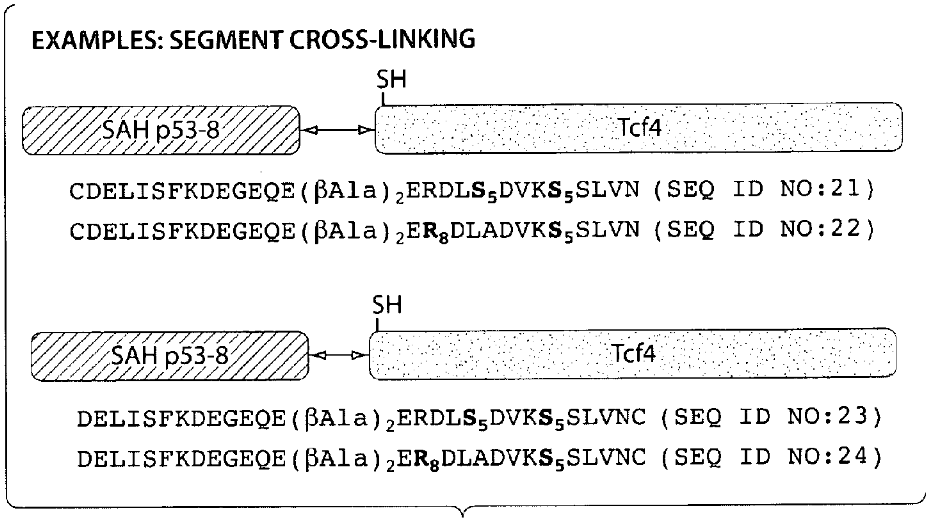
FIG. 14 depicts examples of segment cross-linking in different orientations.

Heterofunctional crosslinkers are used to join the two peptide domains together. The NHS ester attacks the primary amine on peptide 1 to form an amide bond, and the maleimide group reacts to free thiol groups such as cysteines on peptide 2 (FIG. 12). FIG. 13 shows typical spacers between NHS and Maleimide, ranging from 2-24 units. The advantage of using this type of crosslinker is that the crosslinked product peptide does not have to be in a specific orientation since the cysteines can be placed at either end of peptide 2 (if peptide 1 is already reacted). FIG. 14 shows that with the NHS-maleimide crosslinker, the two functional peptides can be joined either in the orientation of N to C or N to N as long as there is a cysteines incorporated in the peptide either at the N-terminal or C-terminal end. This results in segment cross-linking in two orientations:

```
Orientation 1:
                                                    (SEQ ID NO: 21)
SAH p53-8-CDELISFKDEGEQE(β-Ala)₂ERDLS₅DVKS₅SLVN

                                                    (SEQ ID NO: 22)
SAH p53-8-CDELISFKDEGEQE(β-Ala)₂ER₈DLADVKS₅SLVN

Orientation 2:
                                                    (SEQ ID NO: 23)
SAH p53-8-DELISFKDEGEQE(β-Ala)₂ERDLS₅DVKS₅SLVNC

                                                    (SEQ ID NO: 24)
SAH p53-8-DELISFKDEGEQE(β-Ala)₂ER₈DLADVKS₅SLVNC
```

Example 2

Screening Procedures to Obtain High Affinity Targeting and Effector Domains

Bifunctional stapled peptides are screened for high affinity binding using various approaches:

1) Synthetic libraries of stapled peptides: The purpose of such a screening is the identification of stapled peptide sequences capable of binding to a specific protein. Libraries are constructed by split-pool synthesis. The peptide sequences is synthesized on bead (split and pool) and is composed of a constant subunit (such as p53, TCF4, or Axin derived stapled peptides) and of a variable subunit (FIG. 15). The variable subunit can be designed based on i,i+4 and i,i+7 architecture (X=random amino acid), e.g.:

$i,i+4: XXX—S_5—XXS—S_5—XX$     1

$i,i+7: XXX—R_8—XXSSXX—S_5$     2

A combinatorial library analogue to sequence 2 was assembled. For X a reduced set of 10 amino acids was chosen (R, Q, F, L, A, W, V, S, H, Y). The assembled sequences were determined by Edman degradation. Dye-labeled target proteins are screened for their ability to interact with the beads (FIG. 15). Sequences of hits are read out by Edman sequencing. In another approach (FIG. 16), a constant region is used to mediate binding to an enzyme (e.g., p53-MDM2 interaction). Due to the enzymatic activity a second protein bound to the variable sequence can be modified. In a subsequent step the induced modification is detected and used as selection criterion.

2) Phage Display: A template helical peptide, APP, is expressed on the pIII coat protein of M13 phage. At least 10 positions are randomized, using all codons encoding all 20 naturally occurring amino acids. Positives are identified by panning. Sequences are optimized by error-prone PCR. High-affinity hits are confirmed using synthetic peptides.

3) Yeast Cell Surface Display: The procedure is carried out as outlined in 2), however the APP is expressed on the outside surface of *Saccharomyces cerevisiae*.

Example 3

Axin-Derived Stapled α-Helices for Use in Bifunctional Peptides

Additional variant bifunctional peptides are synthesized:

(SEQ ID NO: 23)
SAH p53-8-DELISFKDEGEQE(β-Ala)$_2$ERDLS$_5$DVKS$_5$SLVNC

Tcf-4: Kd ~100 nM, as in Example 1.
Axin-derived stapled α-helices are used
SEQ ID NO: 25, Kd ~3 μM).
(ENPESILDEHVQRVMR, (SEQ ID NO: 26)
SAH p53-8-NPE-S$_5$-ILD-S$_5$-HVQRVMR (SEQ ID NO: 27)
SAH p53-8-NPESILD-S$_5$-HVQ-S$_5$-VMR (SEQ ID NO: 28)
SAH p53-8-NPE-R$_8$-ILDEHV-R$_5$-RVMR Affinity is increased as compared to the non-stapled wild type sequence SEQ ID NO: 25 (Kd~3 μM). In addition these shorter all-helical peptides exhibit higher cell permeability than the TCF4 derived sequences, which consist of a helical and an unstructured subunit.

Example 4

Bifunctional Stapled Peptides for Degradation of c-Myc c-Myc is a master regulator of genes involved in cell growth, protein synthesis and metabolism and a key positive cell cycle regulator. It is inappropriately activated in ca. 30% of all human tumors and as such is considered, after K-Ras, to be the second most frequently activated oncoprotein in human cancer [see *Nat. Rev. Mol. Cell Biol.* 9, 810-5 (2008); *Nature* 455, 679-83 (2008); *Nat. Rev. Mol. Cell Biol.* 6, 635-45 (2005); *Nat. Rev. Mol. Cell Biol.* 5, 805-10]. Structurally, c-Myc is a member of the basic helix-loop-helix leucine zipper (bHLH-Zip) transcription factor family. C-Myc is itself a momoneric protein, but its ability to regulate gene expression is dependent upon formation of a DNA-binding heterodimer with partner proteins of the bHLH-Zip family, namely Mad, Max, and Mxi-1. The structure of the c-Myc is known [Nair and Burley, *Cell* 112, 193-205 (2003)]. Max specifically dimerizerizes with c-Myc, and c-Myc/Max heterodimers function as transcriptional activators, binding the E-box hexanucleotide motif Mad, and Mxi-1 are antagonizing the cell cycle promoting activity of the c-Myc/Max heterodimers. Mad and Mxi can heterodimerize with Max, depriving c-Myc of a partner. The Max/Mad or Max/Mxi-1 partners either fail to activate or actively repress transcription, leading to a state of growth inhibition, quiescence, and/or cell differentiation. Max proteins are metabolically stable and are constitutively expressed, while c-Myc, Mad, and Mxi-1 are unstable, responding to the level of mitotic stimulation in the cell.

c-Myc activity and stability are regulated by phosphorylation and ubiquitination. For example, increased phosphorylation of c-Myc at Thr58 can induce degradation of c-Myc via ubiquitination-proteasomal degradation. The E3 ligase complex responsible for the degradation of c-Myc is a SCF complex associated with the F-box protein FBW7. Fbxw7 (also known as Fbw7, Sel-10, hCdc4, or hAgo) induces the degradation of positive regulators of the cell cycle, such as c-Myc, c-Jun, cyclin E, and Notch. FBXW7 is often mutated in a subset of human cancers.

Increased levels of c-myc, for example as a result of reduced degradation via proteasome can lead to cancer. However, ectopically active SCF (for example by overexpression of Skp2) can also contribute to cancer, because SCF also targets $p27^{KIP1}$ for proteasomal degradation. $p27^{KIP1}$ is an inhibitor of cyclin-dependent kinases (e.g., CDK1 and CDK2) and an important negative regulator of the cell cycle. Degradation of p27 CKI leads to increase tumor aggressiveness and worsening of prognosis in several types of human cancers.

A main advantage of specifically targeting SCF or another E3 ligase to c-Myc using the bifunctional peptides described herein is that c-Myc degradation can be specifically induced without simultaneously inducing the degradation of other factors, such as, for example, $p27^{KIP1}$.

Bifunctional peptides comprising a targeting domain and an effector domain are synthesized that tether c-Myc and an E3 ligase to promote the degradation of c-Myc. In addition, bifunctional peptides comprising a targeting domain and an effector domain are synthesized that tether c-Myc and a kinase increasing c-Myc phosphorylation, for example, the phosphorylation of Thr58 to promote the degradation of c-Myc. In addition, bifunctional peptides comprising a targeting domain and an effector domain are synthesized that tether Max constitutively (that means independent of mitogenic stimuli) to either Mad or Mxi-1 to deprive c-Myc of its activating partner and to inactivate c-Myc.

Example 5

Bifunctional Stapled Peptides for Degradation of HIF

Hypoxia-inducible factor (HIF) is a transcriptional regulatory protein that controls genes involved in angiogenesis, glucose utilization, and resistance to hypoxic stress. HIF is believed to be essential for the growth of solid tumors, as escape from hypoxia-induced apoptosis is a necessary precondition for the formation of a tumor mass larger than a few tenths of a millimeter. More recently, it has been appreciated that HIF also has a profound role in energy utilization, upregulating the expression of glycolytic genes in cell states during which they would ordinarily be quiescent. This raises the intriguing possibility that HIF inhibition will be useful in treating both solid and blood-borne cancers. HIF is a heterodimer comprising one unit of an inducible subunit, HIF-1α, and a constitutive subunit known as ARNT or HIF-1β. Both subunits are members of the basic-helix-loop-helix structural family (bHLH) and so are structurally related to cMyc, but both HIF subunits lack the leucine zipper motif of c-Myc.

HIFα activity is regulated by enzymatic oxygen-dependent hydroxylation of two specific prolyl residues and one critical asparaginyl residue by the oxoglutarate-dependent dioxygenases PHD 1-3 and a protein termed factor inhibiting HIF (FIH). Prolyl hydroxylation results in von Hippel-Lindau (VHL) complex-mediated ubiquitination of HIFα and consequent degradation by the proteasome. Similarly, asparaginyl hydroxylation inhibits CBP/p300 coactivator recruitment by HIFα chains (Bruick & McKnight, 2002). Inactivation of the VHL gene (e.g., by mutation) is associated with the development of highly vascularized tumors.

Bifunctional peptides comprising a targeting domain and an effector domain are synthesized that tether HIF-1α or HIF-1β and an E3 ligase to promote the degradation of HIF-1α or HIF-1β.

Example 6

Bifunctional Peptides for Promotion of GTPase Functions of Mutated Ras

Ras is a small GTP binding protein that operates as a molecular switch regulating the control of gene expression, cell growth, and differentiation through a pathway from receptors to mitogen-activated protein kinases (MAPKs). Oncogenic mutations in the human Ras genes (H-, N-, and K-Ras) are observed in 30% of human cancers. Pancreas, colon, and lung tumors are most often associated with Ras mutations. Most mutations have been detected in the K-Ras gene, and they typically involve missense substitutions of the encoded GTPase in one of three amino acid positions (12, 13, or 61) that occupy the catalytic site of GTP hydrolysis. The mutated forms of Ras remain GTP-bound, and transduce constitutive signals for cell proliferation.

The intrinsic catalytic activity of the Ras GTPase is inefficient and requires a GTPase-activating protein (GAPs) to function as an off-switch. Four types of Ras-specific GAPs have been identified, including p120 Ras GAP, neurofibromin (NF-1), SynGAP, and the GAP1 family. Ras mutational substitutions lead to diminished intrinsic GTPase activity, and to resistance to GTPase stimulation by Ras-specific GAPs.

The GTPase defect in oncogenic Ras is based in part on glutamine 61 of Ras that activates a water molecule for nucleophilic attack, and its substitution by any other amino acid abolishes both intrinsic and GAP-stimulated GTPase activity. The crystal structure of the Ras-RasGAP complex revealed that any mutation of glycine 12 or glycine 13 positions a side-chain that both displaces glutamine 61 and sterically occludes the catalytic 'arginine finger' of GAP (R789), resulting in a loss of intrinsic and GAP-stimulated GTPase activity [Scheffzek et al. *Science*, (1997) 277: 333-338], with the exception of a Ras proline 12 mutant, which activates intrinsic GTPase activity. Ras proline 12 cannot transform cultured cells, suggesting that partial restoration of the GTPase activity of oncogenic Ras mutants might prevent oncogenesis.

Small molecule-based therapies designed to target Ras are currently based on inhibition of the enzyme FTase. FTase catalyzes the COOH-terminal farnesylation of Ras, a post-translational modification that is essential for Ras function. However, these inhibitors do not selectively target the oncogenic forms of Ras, and, may disrupt the functions of wild-type Ras that are required in normal cells. Fischbach et al. [*Cancer Research* (2003) 63, 4089-4094] have shown that nucleoside diphosphate kinase (Ndk, human ortholog NM23) is a metastasis suppressor effectively inactivates several of the oncogenic forms of Ras that are seen frequently in human cancers, including RasD12 and does not detectably affect wild-type Ras or an activated form of the Ras-related Rho GTPase.

Bifunctional peptides of the invention are used to tether GAPs and/or Ndk to mutated Ras to promote GTPase function.

Example 7

Bifunctional Peptides of Phosphorylation of STAT

In alternative approaches to directly modifying Ras and/or c-Myc downstream effectors, such as STAT3 and STAT5 can be modified using the bifunctional peptides of the invention. STAT 3 and STAT 5 are phosphorylated and active in many cancers, for example in Ras and/or c-Myc transformed cancers. Inactivation of oncogenic Ras or c-Myc leads, in certain cancers, to de-phosphorylation of STAT 3 and STAT 5 and regression of the cancer. Bifunctional peptides of the invention are used to tether a specific phosphatase to STAT3 and/or STAT 5 to dephosphorylate STAT3 and/or STAT 5.

Example 8

Transcription Factor Degradation Through Targeted Ubiquitination

Figure 17:
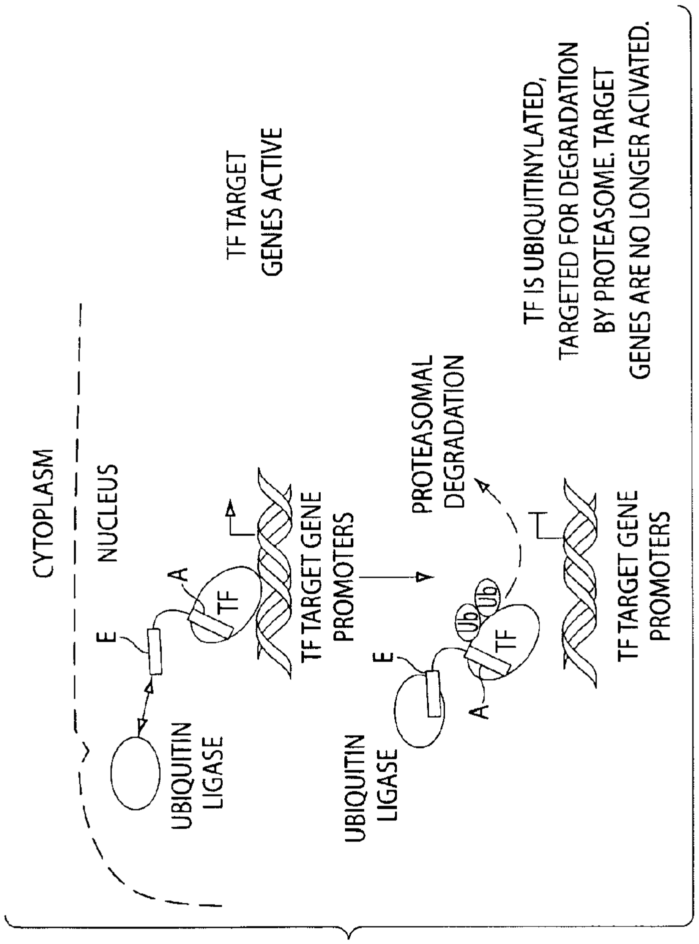
FIG. 17 depicts a diagram showing degradation through targeted ubiquitination.

The effector domain (E) is designed as a signal peptide or small molecule capable of binding and recruiting a ubiquitin-ligase protein, such as MDM2 or FBXW7. The proximity of the ubiquitin-ligase protein bound to the effector domain (E) and a transcription factor (or transcription factor complex) bound to the targeting domain (A) leads to enhanced ubiquitination or restored ubiquitination, if, for example, wild-type ubiquitination sites on the target protein have been mutated and ubiquitination no longer occurs at these sites, for example in β-catenin, Notch, and c-Myc. Ubiquitination of the transcription factor leads to proteasomal degradation (see FIG. 17). For example, the effector domain (E) is designed according to the FXXFF motif-containing stapled peptides capable of binding and recruiting MDM2 or MDMX; the p53 activation domain 1: Ac-LSQETFSDLWKLLPE-$CONH_2$ (SEQ ID NO:35), which can be stapled, and/or may comprise non-natural amino acids; small molecules capable of binding MDM2, such as Nutlin-3; or peptides capable of binding FBXW7 E3-Ubiquitin ligase. The following stapled peptides are useful as effector domains:

| | |
|---|---|
| Ac-LSQETFS*LWK*LPE-$CONH_2$ | (SEQ ID NO: 36) |
| Ac-QSQQTF#NLWRKK*QN-$CONH_2$ | (SEQ ID NO: 37) |
| Ac-QSQQTF*NLW*KKQN-$CONH_2$ | (SEQ ID NO: 38) |
| Ac-LSQNTFS*LWK*LPQ-$CONH_2$ | (SEQ ID NO: 39) |

Where "*" is the non-natural amino acid S5 and "#" is the non-natural amino acid R8. In any arrangement, these amino acids are cross-linked.

Any part of the targeting domain A may be linked to any part of the effector domain E through the linker L. For example, the linkage is N-terminus to N-terminus, the linkage is C-terminus to N-terminus, the linkage is C-terminus to C-terminus, or the linkage is through interior amino acids of one or both peptides. The linkage is typically positioned in such a way as to avoid interfering with the binding activity of the peptide and/or to avoid interfering with the stapling of the peptide. The linker can be proteinogenic or non-proteinogenic. The linker can be a covalent bond (e.g., a carbon-carbon bond, disulfide bond, carbon-heteroatom bond), or it can be a polymeric linker (e.g., polyethylene, polyethylene glycol, polyimide, polyester). The linker can comprise a monomer, dimer, or polymer of aminoalkanoic acid, or the linker can comprise an aminoalkanoic acid (e.g., glycine, ethanoic acid, alanine, beta-alanine, 3-aminopropanoic acid, 4-aminobutanoic acid, 5-pentanoic acid). For example, the linker can comprise a monomer, dimer, or polymer of aminohexanoic acid (Ahx) or polyethylene glycol moiety (PEG). The linker can comprise amino acids. The linker can include funtionalized moieties to facilitate attachment of a nucleophile (e.g., thiol, amino) from the peptide to the linker. The linker can include a maleimide group or a NHS ester or the linker includes both a NHS ester and a maleimide group.

Example 9

Figure 18:
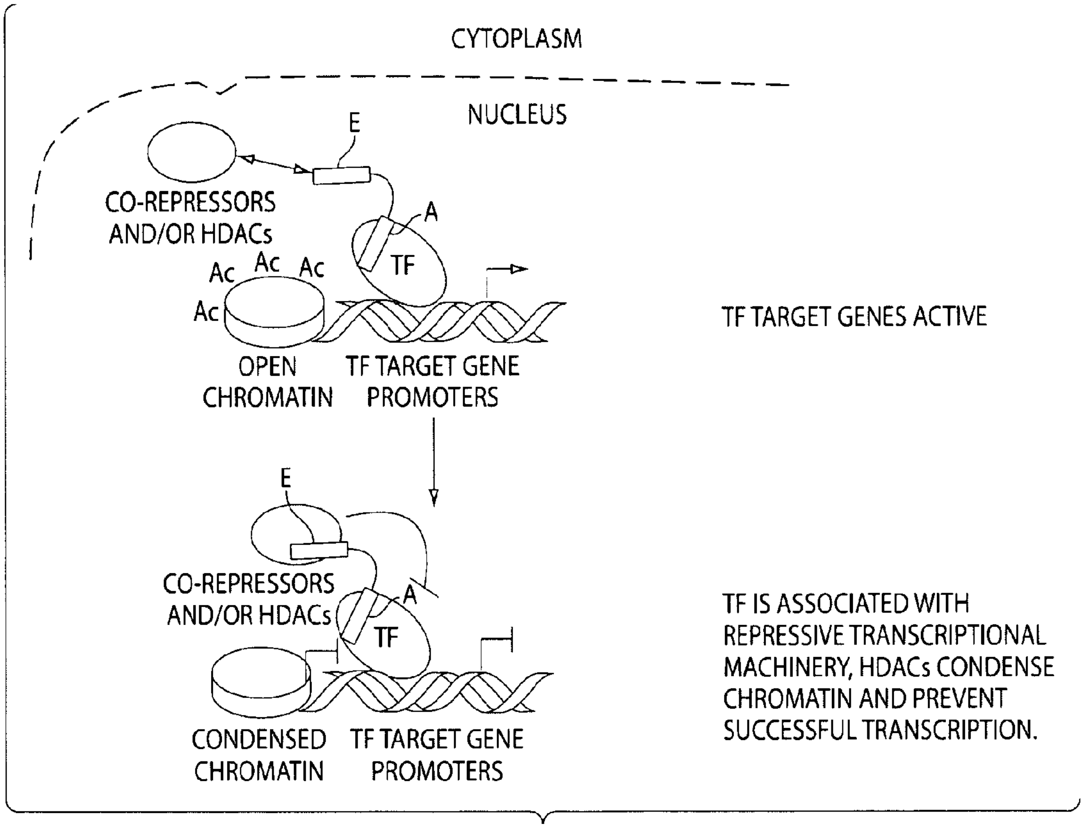
FIG. 18 depicts a diagram showing target gene repression through recruitment of co-repressors.

Transcription Factor Target Gene Repression Through Recruitment of Co-Repressors The effector domain (E) is designed as a domain capable of binding and recruiting co-repressors, histone deacetylases (HDACs), or other general transcription repressors, imposing active repression at transcription factor target-gene promoters and/or repression through epigenetic changes, e.g. through HDAC-mediated chromatin condensation (see FIG. 18). The effector domain (E) is designed as a signal peptide or small molecule capable of binding co-repressor proteins such as Groucho/TLE1, SHARP, NCoR, NCoR2, SMRT, BCoR, or others.

For example, engrailed homology (Eh1) domains that are found in transcription factors and are known to be essential and sufficient for recruiting Groucho/TLE1 co-repressors to target promoters are designed. This domain relies on a short peptide sequence for the interaction: Ac-TPFYIEDILG-$CONH_2$ (SEQ ID NO:40). "E" peptides or peptidomimetics of this domain tethered to "A" enact target-gene repression.

Figure 24A:
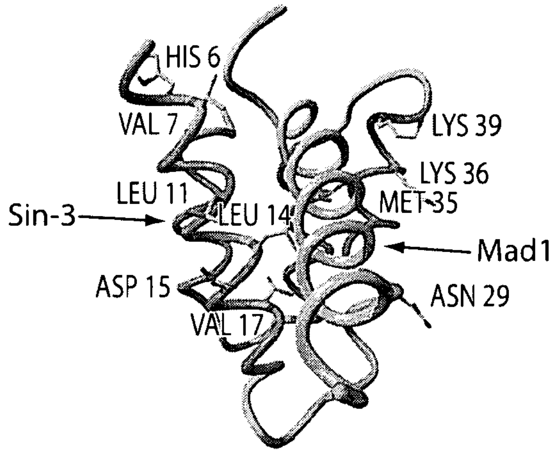
FIG. 24 depicts molecular models for (A) Sin3/Mad1 interaction (Geuzennec et al., *J. Biol. Chem.,* 2004. 279, 25823-9; incorporated herein by reference) and (B) KIX/c-Myb and KIX-MLL interaction (KIX:c-Myb: Zor et al., *JMB,* 2004, 337, 521-34, incorporated herein by reference; KIX:MLL: Guzman et al., *JMB,* 2005, 355, 1005-13, incorporated herein by reference).

In another example, the amphipathic alpha-helix of Mad1 that binds and retains the Sin-3 repressive complex through its PAH domain is designed (see FIG. 24A). A natural or stapled variant of this peptide sequence serves as an effective "E" domain: Ac-VRMNIQMLLEAADYLERRER-$CONH_2$ (SEQ ID NO:41).

Examples of stapled "E" domains from Mad1:

```
Ac-VRMNIQMLLEA*DYL*RRER-CONH2     (SEQ ID NO: 67)

Ac-VRMNIQM*LEA*DYLERRER-CONH2     (SEQ ID NO: 68)

Ac-VRMNIQML#EAADYL*RRER-CONH2     (SEQ ID NO: 69)

Ac-VRM*IQM*LEAADYLERRER-CONH2     (SEQ ID NO: 70)
```

Where "*" is the non-natural amino acid S5 and "#" is the non-natural amino acid R8. In any arrangement, these amino acids are cross-linked.

Example 10

Figure 19:
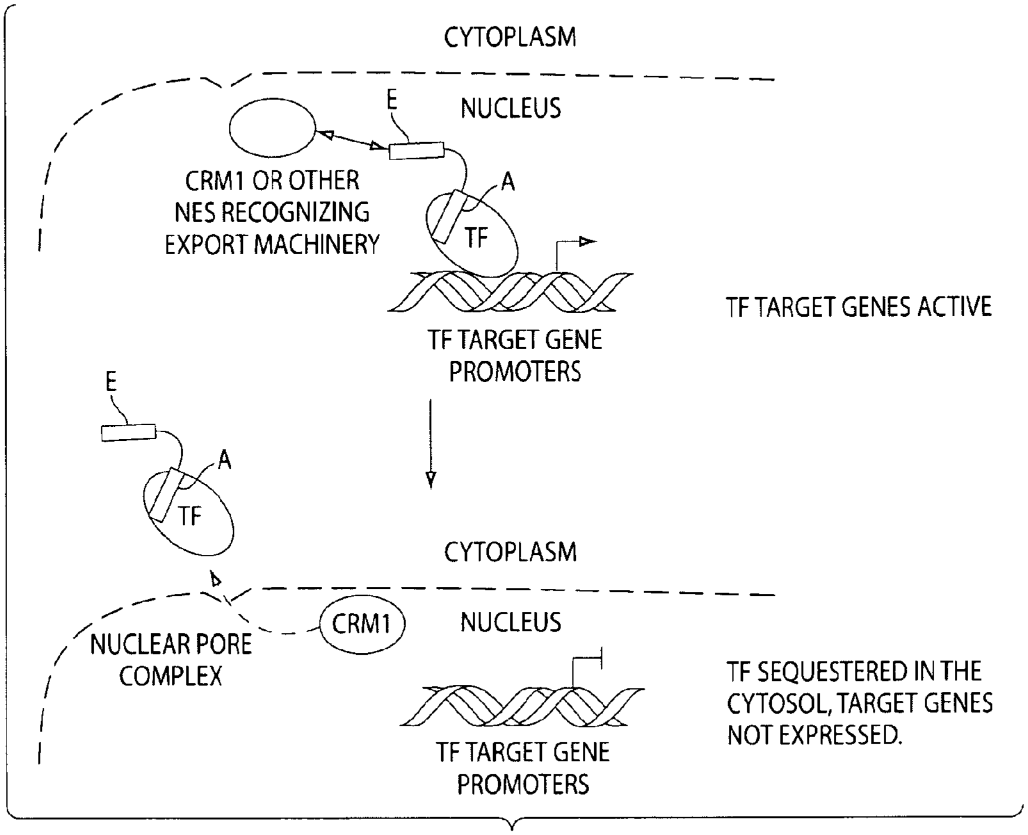
FIG. 19 depicts a diagram showing transcription factor inhibition by targeted nuclear export with Nuclear Export Sequence (NES)-containing bi-functional peptides.

Transcription Factor Inhibition by Targeted Nuclear Export with Nuclear Export Sequence (NES)-Containing Bi-Functional Peptides The effector domain (E) is designed as a domain capable of binding and recruiting the nuclear export machinery, thus targeting the "A"-transcription factor complex for nuclear export to the cytosol. Active export by exportins such as CRM1 disable the transcription factor-specific gene expression programs by spatially preventing transcription factor function (see FIG. 19). The effector domain "E" is designed as signal peptides or small molecules capable of binding nuclear export proteins such as CRM1 (Exportin 1). Many CRM1-interacting NES domains have been discovered and usually consist of a 10-20 residue peptide with a 5-6 residue hydrophobic core. For example, the HR3 domain in the dengue virus NS5 protein, which has been found to export a variety of fused protein cargo is such domain. An "E" fusion of the peptide: Ac-LLTKPWDIIPMVTQMAM-$CONH_2$ (SEQ ID NO:71) is made which promotes nuclear export of the target transcription factor (Rawlinson S M et al., *J.B.C.* 2009, 284, 15589-97). Another example of a short, well-characterized NES that interacts with CRM1 is from the activation domain of the HIV-1 REV protein. An "E" fusion: Ac-CLRRLERLTL-$CONH_2$ (SEQ ID NO:72) has been shown to promote export of fusion proteins and furthermore a mutant (LE to DL) is inactive, indicating a specific interaction. (Fischer U et al., *Cell,* 1995, 82, 475-83).

Example 11

Figure 20:
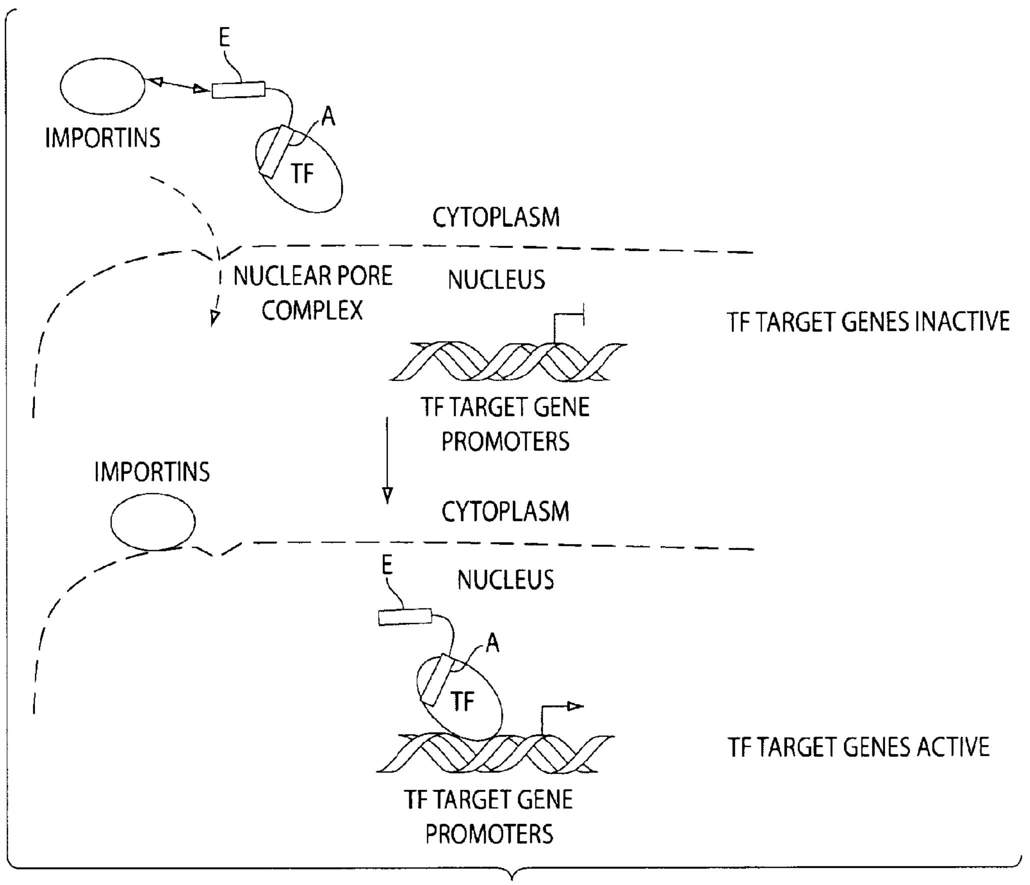
FIG. 20 depicts a diagram showing transcription factor activation by targeted nuclear import with nuclear localization sequence (NLS)-containing bifunctional peptides.

Transcription Factor Activation by Targeted Nuclear Import with Nuclear Localization Sequence (NLS)-Containing Bi-Functional Peptides The effector domain (E) is designed as signal peptides or small molecules comprising or mimicking a nuclear localization sequence (NLS) to bind nuclear import proteins (see FIG. 20). NLS sequences that are known to target and bind Impα are designed.

Exemplary NLS sequences are:

```
                                              (SEQ ID NO:42)
SV40 T-antigen:     Ac-PKKKRKVE-CONH2;

                                              (SEQ ID NO: 43)
Nucleoplasmin:      Ac-KRPAATKKAGQAKKKKLD-CONH2;

                                              (SEQ ID NO: 44)
c-Myc:              Ac-PAAKRVKLD-CONH2.
```

(Gorlich D and Kutay U. *Annu. Rev. Cell Dev. Biol.* 1999, 15: 607-60)

Example 12

Figure 21:
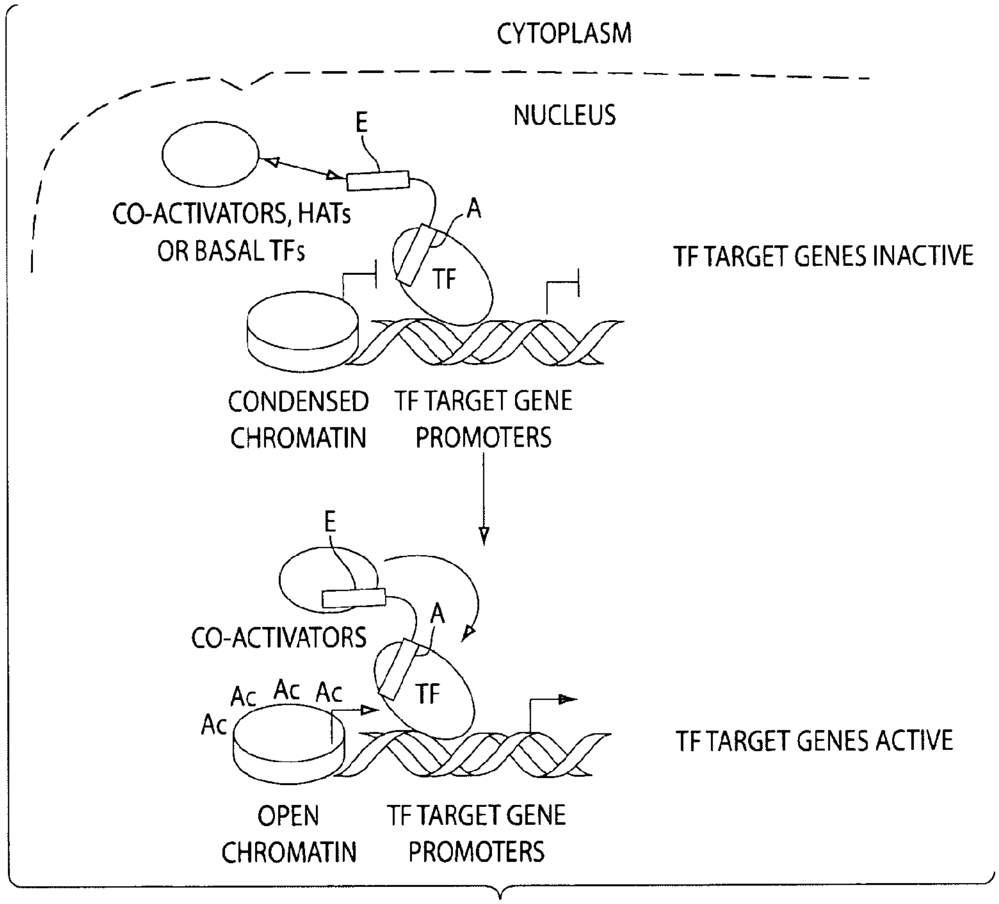
FIG. 21 depicts a diagram showing synthetic transcription factor activation by recruitment of co-activator proteins.

Synthetic Transcription Factor Activation by Recruitment of Co-Activator Proteins The effector domain (E) is designed as peptides or small molecules capable of binding and recruiting specific transcriptional co-activator proteins or components of the basal transcriptional apparatus. Synthetic transcriptional activation enables augmented gene expression driven by specific transcription factors or a return to basal gene expression levels for transcription factors that have been inappropriately suppressed, for example, by mutation (see FIG. 21).

Figure 24B:
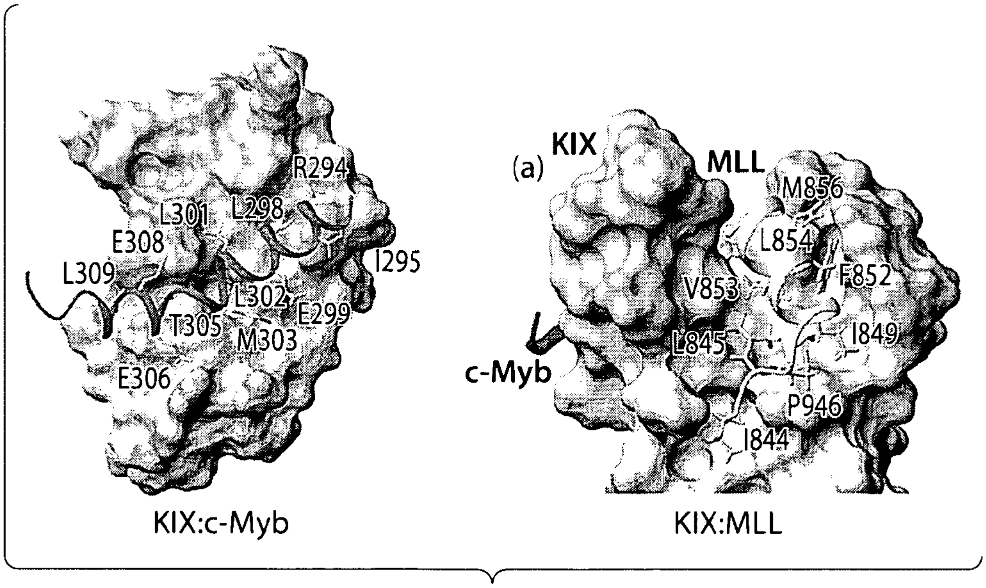

Signal peptides or small molecules comprising or mimicking co-activator binding domains are designed. Also, molecules capable of specifically recognizing and recruiting basal transcriptional proteins such as TAFII proteins and/or RNA polymerases are designed as wild-type or synthetically modified by non-natural amino acids and peptide stapling. Specifically, the KIX domain of CBP/p300 has two distinct binding sites targeted by transcription factors to localize and retain the co-activator protein (see FIG. 24B). Suitable alpha-helical peptide "E" domains targeting these binding sites include:

| | | |
|---|---|---|
| p53 AD1: | Ac-LSQETFSDLWKLLPE-$CONH_2$ | (SEQ ID NO: 45) |
| p53 AD2: | Ac-MLSPDDIEQWFTEDPG-$CONH_2$ | (SEQ ID NO: 46) |
| MLL: | Ac-ILPSDIMDFVLKNTP-$CONH_2$ | (SEQ ID NO: 47) |
| c-Jun: | Ac-LASPELERLIIQSSN-$CONH_2$ | (SEQ ID NO: 48) |
| HLTV-TAX: | Ac-YIDGFVIGSALQFLIPRLP-$CONH_2$ | (SEQ ID NO: 49) |
| c-MYB: | Ac-KEKRIKELELLLMSTENELKG-$CONH_2$ | (SEQ ID NO: 50) |
| pKID: | Ac-ILSRRPSYRKILNDLSSDAPG-$CONH_2$ | (SEQ ID NO: 51) |

Stapled "E" peptides derived from c-Myb are:

| | |
|---|---|
| Ac-KEKRIKELEL*LMS*ENELKG-$CONH_2$ | (SEQ ID NO: 52) |
| Ac-KEKRIK*LEL*LMSTENELKG-$CONH_2$ | (SEQ ID NO: 53) |
| Ac-KE*RIK*LELLLMSTENELKG-$CONH_2$ | (SEQ ID NO: 54) |
| Ac-KEKRIK#LELLLM*TENELKG-$CONH_2$ | (SEQ ID NO: 55) |
| K*KRI*ELELLLMSTENELKG | (SEQ ID NO: 73) |
| K*KRI*RLELLLMSTENELKG | (SEQ ID NO: 74) |
| KE*RIK*LELLLMSTENELKG | (SEQ ID NO: 75) |
| KR*RIK*LELLLMSTENELKG | (SEQ ID NO: 76) |
| KE*RIKELE*LLMSTENELKG | (SEQ ID NO: 77) |
| KE*RIKRLE*LLMSTENELKG | (SEQ ID NO: 78) |
| KR*RIKELE*LLMSTENELKG | (SEQ ID NO: 79) |
| KEKRIKELELLLMSTE*ELK* | (SEQ ID NO: 80) |

Stapled "E" peptides derived from MLL:

| | |
|---|---|
| Ac-*ILP*DIMDFVLKNTP-$CONH_2$ | (SEQ ID NO: 56) |
| Ac-ILP*DIM*FVLKNTP-$CONH_2$ | (SEQ ID NO: 57) |
| Ac-ILPSDIM*FVL*NTP-$CONH_2$ | (SEQ ID NO: 58) |
| Ac-ILPSDIMDFV*KNT*-$CONH_2$ | (SEQ ID NO: 59) |
| Ac-#ILPSDI*DFVLKNTP-$CONH_2$ | (SEQ ID NO: 60) |
| ILP*DIM*FVLKNT | (SEQ ID NO: 81) |
| ILP*RIM*FVLKNT | (SEQ ID NO: 82) |
| ILPSDIM*FVL*NT | (SEQ ID NO: 83) |
| ILPSRIM*FVL*NT | (SEQ ID NO: 84) |

Stapled "E" peptides derived from p-KID (where any serine residues, in particular Ser133, can be phosphorylated, as is present in the native pKID:KIX interaction):

| | |
|---|---|
| Ac-ILSRRPSY*KIL*DLSSDAPG-$CONH_2$ | (SEQ ID NO: 61) |
| Ac-ILSRRPSYRKIL*DLS*DAPG-$CONH_2$ | (SEQ ID NO: 62) |
| Ac-ILSR*PSY*KILNDLSSDAPG-$CONH_2$ | (SEQ ID NO: 63) |
| Ac-ILSRRPSYR*ILN*LSSDAPG-$CONH_2$ | (SEQ ID NO: 64) |
| Ac-ILSRRP#YRKILN*LSSDAPG-$CONH_2$ | (SEQ ID NO: 65) |
| Ac-ILSRRPSYRKILNDLSSDAPG-$CONH_2$ | (SEQ ID NO: 66) |

Where "*" is the non-natural amino acid S5, and "#" is the non-natural amino acid R8. In any arrangement, these amino acids are cross-linked.

Example 13

Figure 22:
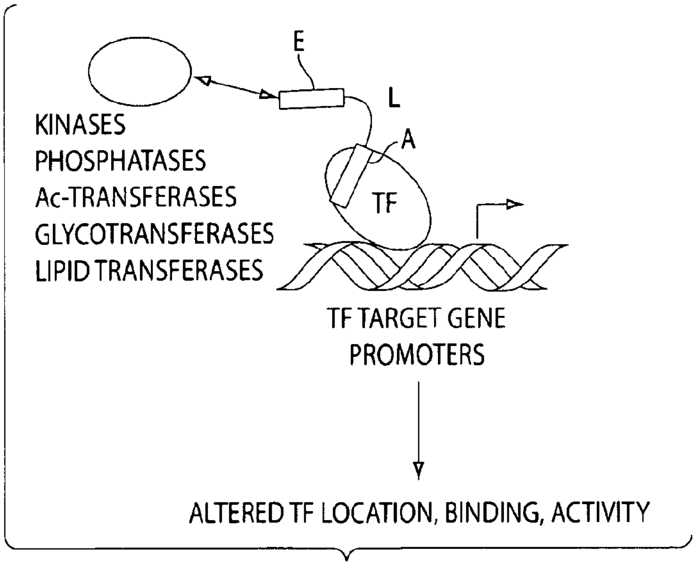
FIG. 22 depicts a diagram showing general transcription factor post-translational modification by tethered effector domains.

General Transcription Factor Post-Translational Modification by Tethered Effector Domains Effector domains (E) are designed comprising peptides or small molecules capable of binding and recruiting specific post-translational modifying enzymes or complexes including kinases, acetyltransferases, phosphatases, glycotransferases, lipid transferases, and other enzymes known to alter transcription factor function (see FIG. 22).

Example 14

Design and Synthesis of Bifunctional Stapled Peptides

Transcription factor targeting ligand, such as SAHM1, a designed stapled peptide capable of binding the Notch:CSL transcription factor complex is designed as a targeting domain (A). For example, SAHM1: Ac-Bala-ERLRRRI*LCR*HHST-$CONH_2$ (SEQ ID NO:73), where "*" is the non-natural amino acid S5, is designed, where SAHM1 is capable of binding the Notch:CSL transcription complex (WO 2008/061192, incorporated herein by reference in its entirety).

Figure 23:
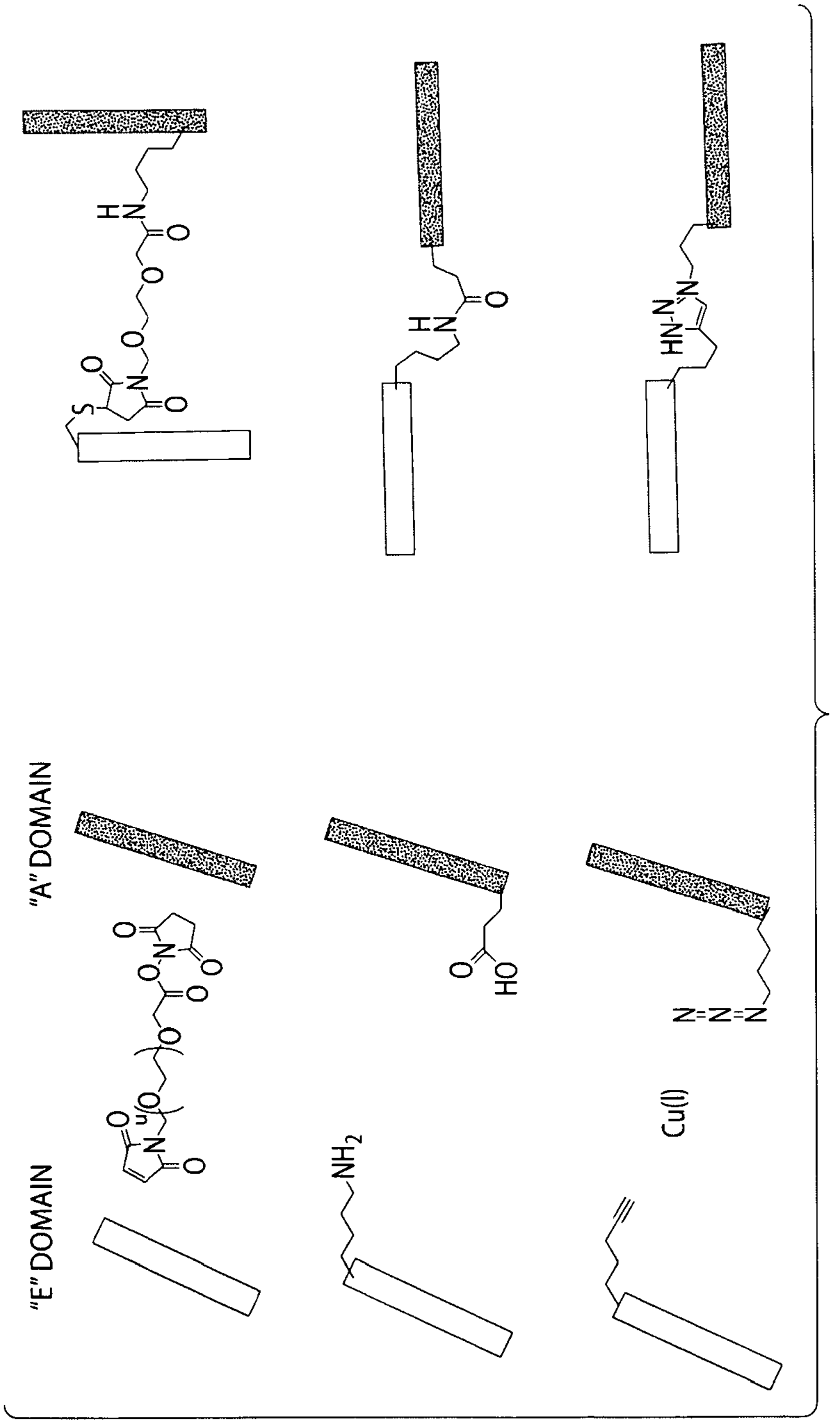
FIG. 23 depicts a diagram showing design and synthesis of bifunctional stapled peptides and attachment strategies.

"E"—Effector domain capable of binding and recruiting cellular machinery to the transcription factor of interest is designed. The goal is to synthesize a tethered form of "A" and "E" such that they are independently functionally active to bind their targets. Through the tether, however, their functions are linked enacting the effects of the effector protein on the TF of interest. Linker synthesis is carried out as outlined in FIG. 23.

Example 15

Stapled Repressive Domains

Stapled repressive domains were developed and analyzed based on effector domains that associate with Sin3 (FIG. 24A). The Sin3 protein is an evolutionary conserved repressor that is part of a 1.2 MDa multi-protein co-repressor complex associated with HDAC activity. The core subunits of the Sin3 complex include HDAC1, HDAC2, RbAp46/48, RBP1, SAP130, BRMS1, SDS3, SAP30, and SAP18. Sin3 contains four conserved imperfect repeats of 100 amino acids termed paired amphipathic helix (PAH) domains which are protein-protein interaction modules. PAH1 is thought to interact with Opi1, Pf1, NRSF, N-CoR, and SMRT. The PAH2 domain interactions for example with Mad protein family members, Sp1-like repressor proteins, HBP1, Pf1, and yeast Ume6. The ability of the tumor suppressor Mad to inhibit cell proliferation and to repress transcription is dependent on an N-terminal N[8]IQMLLEAADYLE[20] domain named SID (Sin3 interacting domain). In nuclear magnetic resonance experiments, Mad SID folds as an amphipathic helix and contacts the PAH2 domain of Sin3 which folds as a four-helix bundle (Brubaker, K. et al. *Cell* 103, 655-665 (2000)). A SID consensus sequences for Mad family members is thought to comprise the following degenerate sequence: ΦZZΦΦX-AAXXΦnXXn with X being any non-proline residue, Φ being a bulky hydrophobic residue, and n being negatively charged residues (Guezennec et al. *Nucl. Acid Res.* 34(14): 3929-3937 (2006)).

Peptides SID1 to SID9 were synthesized:

| | | |
|---|---|---|
| SID Long (5-28): | VRMNIQMLLEAADYLERREREAEH | (SEQ ID NO: 85) |
| SID short (5-24): | VRMNIQMLLEAADYLERRER | (SEQ ID NO: 86) |
| Consensus: | XXXΦZZΦΦXAAXXΦEX | |
| SID1: | βAla-ERLRRRI*MLL*AANYLER | (SEQ ID NO: 87) |
| SID2: | βAla-VRRRI*MLL*AANYLER | (SEQ ID NO: 88) |
| SID3: | βAla-VRRRIQRLL*AAN*LER | (SEQ ID NO: 89) |
| SID4: | βAla-VRMNIQMLLQAANR*ERR*R | (SEQ ID NO: 90) |
| SID5: | βAla-VRRRIQMLLEAANK*ERR*R | (SEQ ID NO: 91) |
| SID6: | βAla-VRMNIQMLLQAANRLERR*REA*H | (SEQ ID NO: 92) |
| SID7: | βAla-VRRRIQMLLEAANKLERR*REA*H | (SEQ ID NO: 93) |
| SID8: | βAla-VRMNIQMLL*AAN*LER | (SEQ ID NO: 94) |
| SID9: | βAla-VRMNI*MLL*AANYLER, | (SEQ ID NO: 95) |

where "*" is the non-natural amino acid S5, and these amino acids are cross-linked. FIG. 25B shows a sample fluorescent polarization experiment data for SID2 and SID5 as compared to wild type SID used to determine dissociation constants ($K_D$). Sin3 binding assays were performed by incubating FITC-SID peptides (10 nM) with serial dilutions of Sin3 in a buffer of 50 mM NaCl, 1 mM DTT, 10 mM Tris pH 7.4. Dilutions and incubations were made in 384-well, black flat-bottom plates (Corning) to a total volume of 100 μL and incubated for 2 hours. Polarization was measured on a Spectramax-M5 multi-label plate reader with $\lambda_{ex}$=485 nm and $\lambda_{em}$=525 nm. Polarization was calculated according to the standard equation: P=(V−H)/(V+H), where P=polarization, V=vertical emission intensity and H=horizontal emission intensity. $K_d$ values were determined by fitting data to a variable-slope sigmoidal binding curve using Kaleidagraph.

FIG. 25C shows confocal microscopy of Hela cells treated with FITC-conjugated SID-series peptides. SID2 and SID5 reveal robust cellular penetration. HeLa cells were grown on chamber slides overnight. 10 mM FITC-SID peptides in DMSO stock solutions were diluted in cell media to a final concentration of 10 μM, along with a 10 μM DMSO control. Cells were incubated in peptide/vehicle solutions at 37° C. for 6 hours, then washed thoroughly with media and PBS, and fixed with 4% paraformaldehyde. Slides were stained with Vectashield™ Hardset with DAPI. Images were taken with a Zeiss 710 confocal microscope.

Example 16

Covalent Conjugation Strategies for Bifunctional Stapled Peptides

Figure 27:
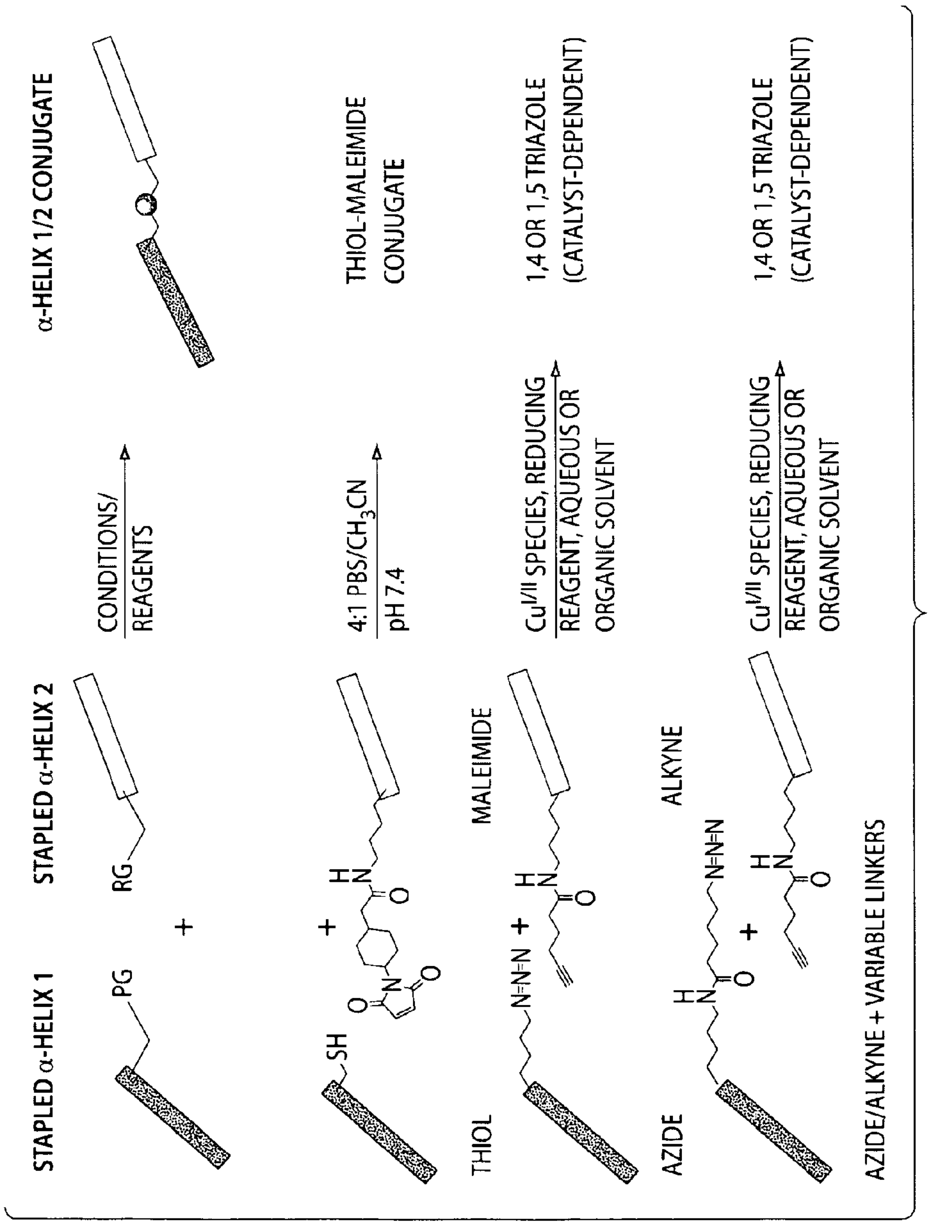
FIG. 27 depicts a diagram showing examples of design and synthesis of bifunctional stapled peptides and attachment strategies.
Figure 30:
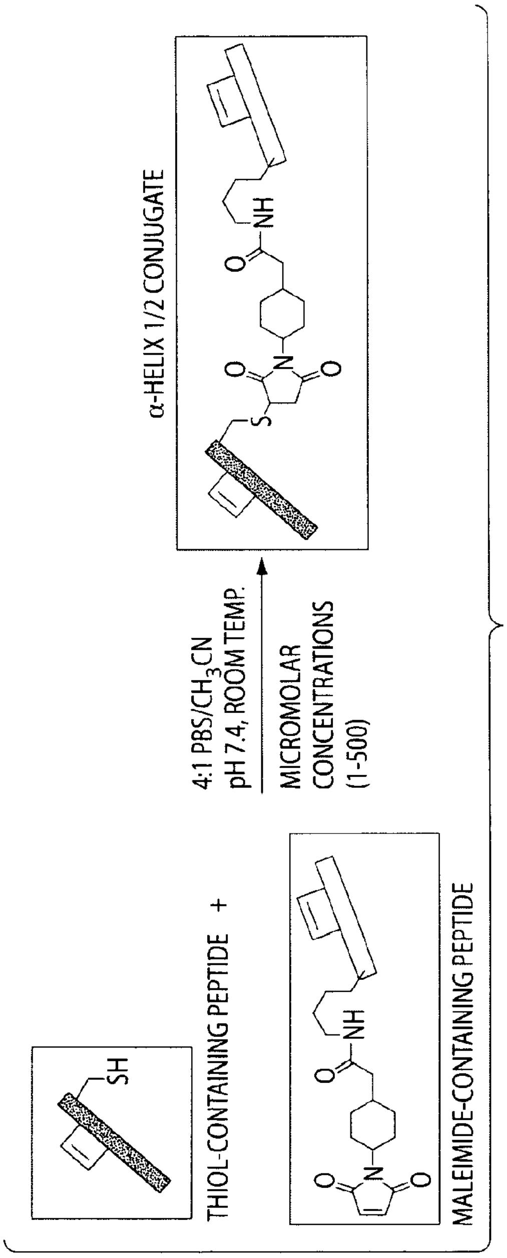
FIG. 30 depicts a diagram showing a conjugated bifunctional stapled peptide associated via reaction of a thiol-containing stapled peptide and a maleimide-containing stapled peptide.

FIG. 27 provides an overview of exemplary conjugation strategies of associating two stapled peptides via chemical linkers (FIG. 27). For example, thiol (—SH) groups and maleimide groups were used as reactive groups to generate thiol-maleimide conjugates. The groups were reacted in a 4:1 PBS/$CH_3CN$ solution at pH 7.4 (FIG. 30). Azide ($N_3$) groups were reacted with alkyne groups using a $Cu^{I/II}$ catalyst and a reducing agent in organic or aqueous solvent to obtain 1,4- or 1,5-triazole moieties. Alkyne/azide reactive groups of various length and configuration may be used.

Figure 28:
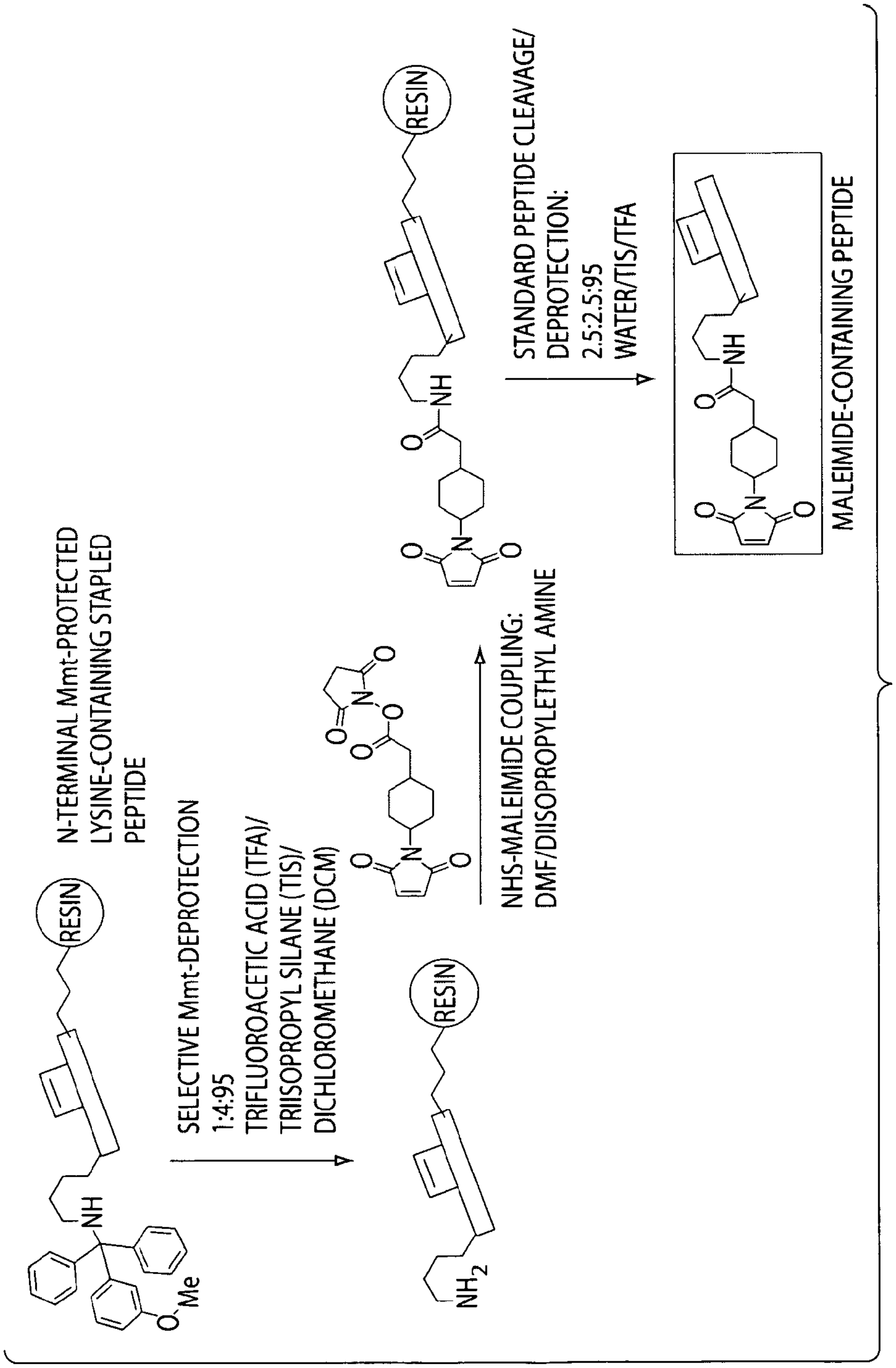
FIG. 28 depicts a diagram showing the synthesis of a stapled peptide containing a maleimide reactive group.

Resin-coupled, maleimide-containing stapled peptides were generated reacting the Mmt-protected lysine residue of the stapled peptide a solution containing 1:4:95 (vol/vol) trifluoroacetic acid (TFA): triisopropyl silane (TIS): dichloromethane (DCM). The deprotected amine-containing stapled peptides were coupled with NHS-Maleimide in DMF/diisopropylethyl amine and the resulting maleimide-containing stapled peptides were cleaved off the resin using standard peptide cleavage and deprotection in a solution containing 2.5:2.5:95 (vol/vol) water:TIS:TFA (FIG. 28).

Figure 29:
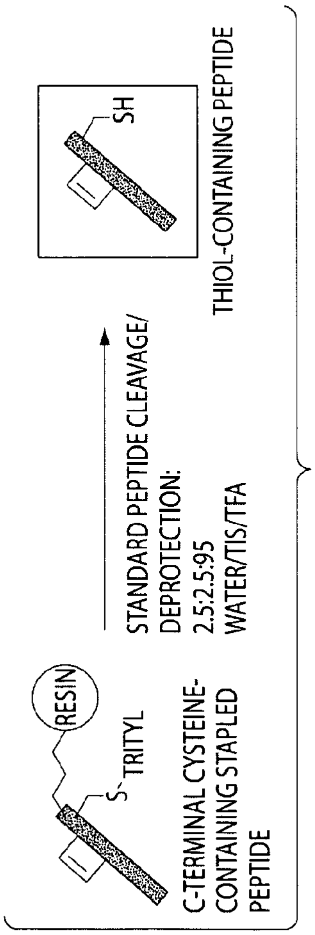
FIG. 29 depicts a diagram showing the synthesis of a stapled peptide containing a thiol reactive group.

Thiol-containing stapled peptides were generated from resin-coupled, cysteines-containing, protected stapled peptides. Peptide release from the resin was accomplished using standard peptide cleavage and deprotection in a solution containing 2.5:2.5:95 (vol/vol) water:TIS:TFA (FIG. 29).

Figure 31:
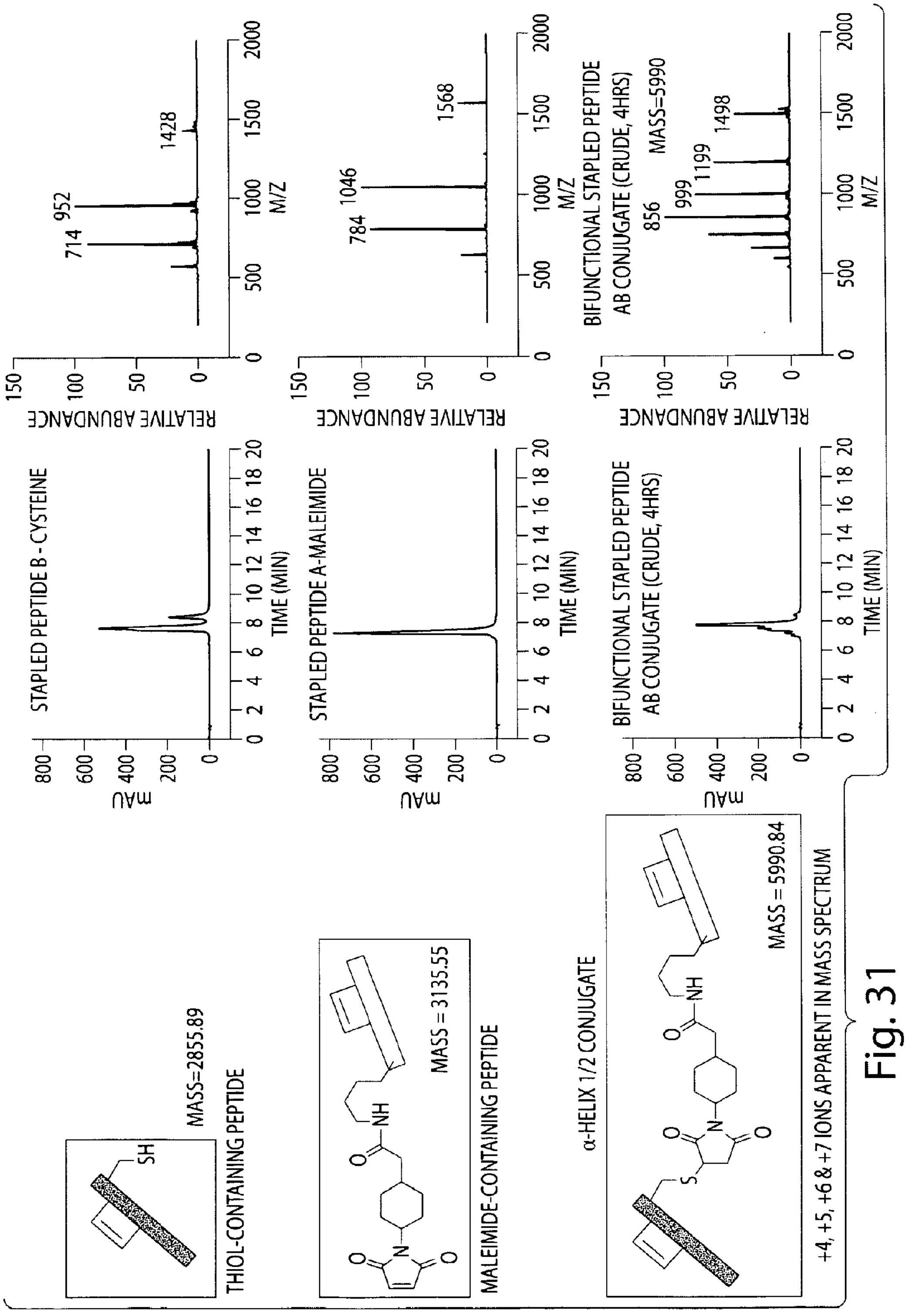
FIG. 31 depicts mass spectrum for a thiol-containing stapled peptide (upper panel), a maleimide-containing stapled peptide (middle panel), and the resulting conjugated bifunctional stapled peptide (lower panel).
Figure 32:
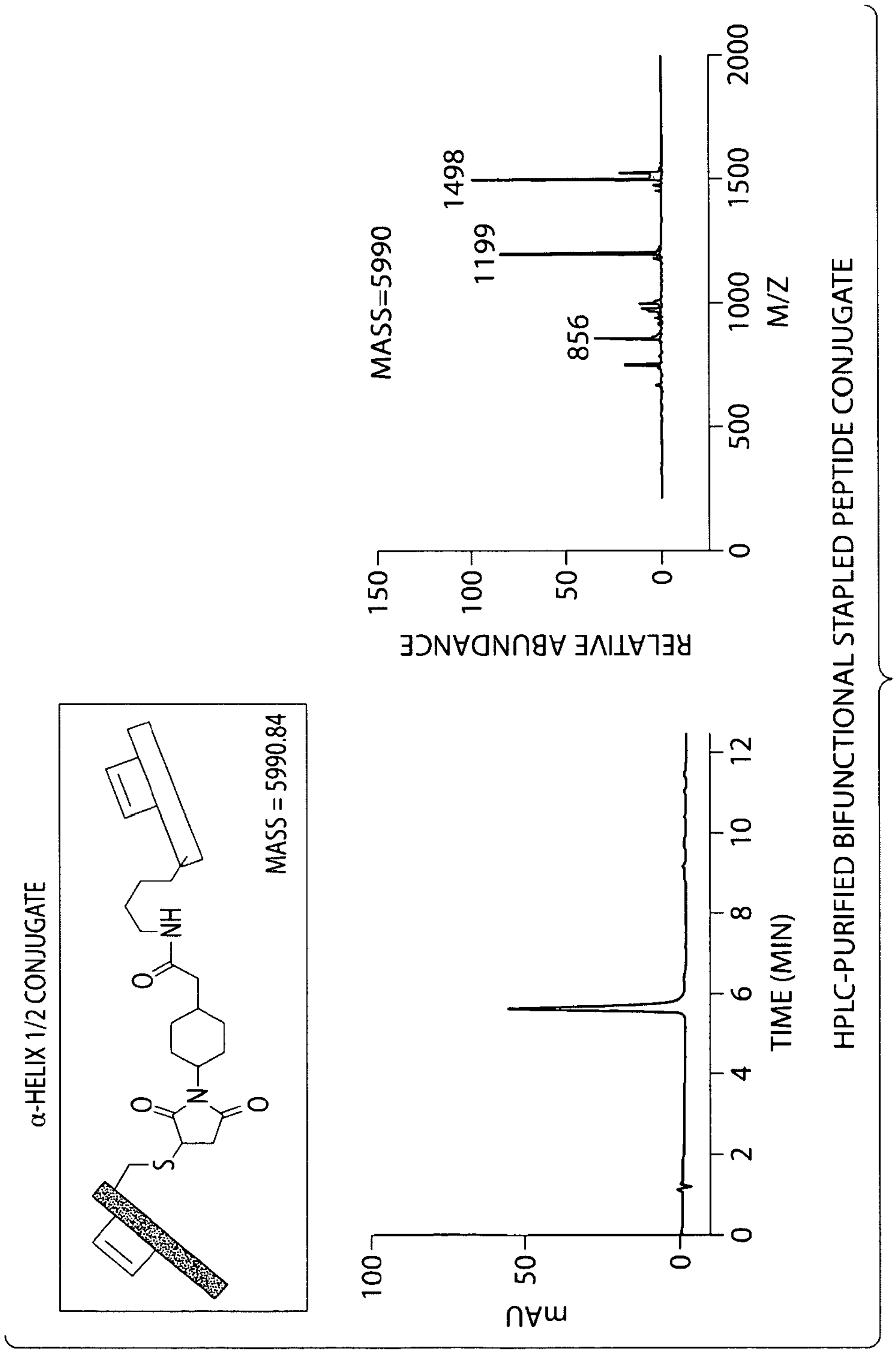
FIG. 32 depicts mass spectrum of an HPLC-purified conjugated bifunctional stapled peptide.

FIG. 31 shows the mass spectrum of a thiol-containing stapled peptide (upper panel), a maleimide-containing stapled peptide (middle panel), and a reacted conjugated bifunctional stapled peptide (lower panel). FIG. 32 shows a mass spectrum of the HPLC-purified conjugated bifunctional thiol-maleimide stapled peptide.

What is claimed is:

1. A bifunctional peptide comprising:

a targeting domain;

a linker moiety; and an effector domain;

wherein the linker moiety links the targeting domain to the effector domain, and both the targeting domain and the effector domain are independently stapled or stitched peptides.

2. The peptide of claim 1, wherein both the targeting domain and the effector domain are stapled.

3. The peptide of claim 1, wherein at least one of the targeting domain and the effector domain comprises a sub-domain of Formula (I):

Formula (I)

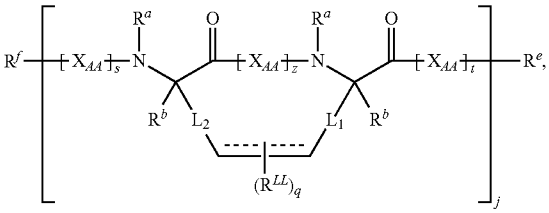

wherein in the sub-domain of Formula (I)

each instance of $L_1$ and $L_2$ is, independently, a bond; a cyclic or acyclic, branched or unbranched, substituted or unsubstituted alkylene; a cyclic or acyclic, branched or unbranched, substituted or unsubstituted alkenylene; a cyclic or acyclic, branched or unbranched, substituted or unsubstituted alkynylene; a cyclic or acyclic, branched or unbranched, substituted or unsubstituted heteroalkylene; a cyclic or acyclic, branched or unbranched, substituted or unsubstituted heteroalkenylene; a cyclic or acyclic, branched or unbranched, substituted or unsubstituted heteroalkynylene; a substituted or unsubstituted arylene; a substituted or unsubstituted heteroarylene; or a substituted or unsubstituted acylene;

each instance of $R^a$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a cyclic or acyclic, substituted or unsubstituted acyl; or an amino protecting group;

each instance of $R^b$ is, independently, an amino acid side chain; hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a cyclic or acyclic, substituted or unsubstituted acyl; a substituted or unsubstituted hydroxyl; a substituted or unsubstituted thiol; a substituted or unsubstituted amino; cyano; isocyano; halo; or nitro;

each instance of $R^e$ is, independently, a bond to the linker moiety; —$R^E$; —$OR^E$; —$N(R^E)_2$; or —$SR^E$;

each instance of $R^E$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; a hydroxyl protecting group; an amino protecting group; a thiol protecting group; or two $R^E$ groups of —$N(R^E)_2$ together form a substituted or unsubstituted 5- to 6-membered heterocyclic or heteroaromatic ring;

each instance of $R^f$ is, independently, a bond to the linker moiety; hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; an amino protecting group; a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ of a terminal amino acid together form a substituted or unsubstituted 5- to 6-membered heterocyclic or heteroaromatic ring;

each instance of $R^{LL}$ is, independently, a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a substituted or unsubstituted hydroxyl; a substituted or unsubstituted thiol; a substituted or unsubstituted amino; azido; cyano; isocyano; halo; or nitro; or two adjacent $R^{LL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of z is, independently, an integer from 2 to 6;

each instance of j is, independently, an integer from 1 to 10;

each instance of s and t is, independently, an integer from 0 and 100;

each instance of q is, independently, an integer from 0 to 2; and

‐‐‐‐‐‐‐‐‐ corresponds to a single or double bond.

4. The peptide of claim 3, wherein ‐‐‐‐‐‐‐‐‐ is a double bond in the sub-domain of Formula (I).

5. The peptide of claim 1, wherein at least one of the targeting domain and the effector domain comprises a sub-domain of Formula (II):

Formula (II)

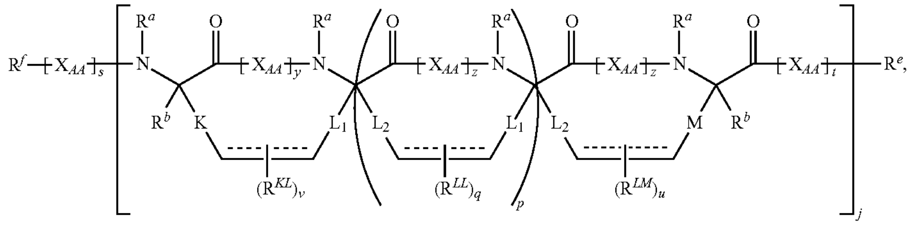

wherein each instance of K, $L_1$, $L_2$, and M, is, independently, a bond; a cyclic or acyclic, branched or unbranched, substituted or unsubstituted alkylene; a cyclic or acyclic, branched or unbranched, substituted or unsubstituted alkenylene; a cyclic or acyclic, branched or unbranched, substituted or unsubstituted alkynylene; a cyclic or acyclic, branched or unbranched, substituted or unsubstituted heteroalkylene; a cyclic or acyclic, branched or unbranched, substituted or unsubstituted heteroalkenylene; a cyclic or acyclic, branched or unbranched, substituted or unsubstituted heteroalkynylene; a substituted or unsubstituted arylene; a substituted or unsubstituted heteroarylene; or a substituted or unsubstituted acylene;

each instance of $R^a$ is, independently, hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a cyclic or acyclic, substituted or unsubstituted acyl; or an amino protecting group;

each instance of $R^b$ is, independently, an amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, a bond to the linker moiety; —$R^E$; —$OR^E$; —$N(R^E)_2$; or —$SR^E$; wherein each instance of $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a hydroxyl, amino, or thiol protecting group; or two $R^E$ groups of —$N(R^E)_2$ together form a substituted or unsubstituted 5- to 6-membered heterocyclic or heteroaromatic ring;

each instance of $R^f$ is, independently, a bond to the linker moiety; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; an amino protecting group; a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro; or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of y and z is, independently, an integer from 2 to 6;

each instance of j is, independently, an integer from 1 to 10;

each instance of p is, independently, an integer from 0 to 10;

each instance of s and t is, independently, an integer from 0 and 100;

each instance of u, v, and q, is, independently, an integer from 0 to 2; and

---------- corresponds to a single or double bond.

6. The peptide of claim 5, wherein ---------- is a double bond in the sub-domain of Formula (II).

7. The peptide of claim 1, wherein the linker moiety is an aminohexanoic acid monomer or a polymer of aminohexanoic acid.

8. The peptide of claim 1, wherein the linker moiety is an aminohexanoic acid monomer.

9. The peptide of claim 1, wherein the linker moiety is a polymer of aminohexanoic acid.

10. The peptide of claim 1, wherein the targeting domain binds β-catenin, Myc, Ras, or hypoxia-inducible factor.

11. The peptide of claim 1, wherein the targeting domain is a ligand for β-catenin.

12. The peptide of claim 11, wherein the targeting domain is a stapled Bcl9 or a derivative thereof, or a stapled Tcf-4 or a derivative thereof.

13. The peptide of claim 12, wherein the targeting domain is a stapled Bcl9 or a derivative thereof.

14. The peptide of claim 12, wherein the targeting domain is a stapled Tcf-4 or a derivative thereof.

15. The peptide of claim 1, wherein the targeting domain is a ligand for Myc.

16. The peptide of claim 15, wherein the targeting domain is a stapled Max or a derivative thereof, a stapled Mad or a derivative thereof, or a stapled Mxi or a derivative thereof.

17. The peptide of claim 1, wherein the targeting domain is a ligand for Ras or hypoxia-inducible factor.

18. The peptide of claim 1, wherein the effector domain modulates the activity of an enzyme.

19. The peptide of claim 18, wherein the enzyme is a ubiquitinating enzyme, a glycosylating enzyme, a histone deacetylase, a histone acetyl transferase, a phosphorylating enzyme, or a dephosphorylating enzyme.

20. The peptide of claim 1, wherein the effector domain is a ligand for a ubiquitinating enzyme.

21. The peptide of claim 20, wherein the ubiquitinating enzyme is an E3 ubiquitin ligase.

22. The peptide of claim 21, wherein the E3 ubiquitin ligase is hDM2, MDM2, ubiquitin protein ligase E3A, a RING finger domain, or an SCF E3 ligase complex.

23. The peptide of claim 22, wherein the E3 ubiquitin ligase is hDM2, and the ligand for hDM2 is a stapled p53.

24. The peptide of claim 1, wherein the effector domain is a ligand for a glycosylating enzyme, a histone deacetylase, a histone acetyl transferase, a kinase, or a phosphatase.

25. The peptide of claim 1, having the Formula (III):

Formula (III)

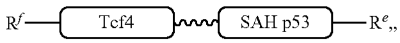

wherein

is a stapled Tcf4 or a derivative thereof;

is a stapled alpha-helix of p53 or a derivative thereof;

is a linker moiety;

$R^e$ is a bond to the linker moiety, —$R^E$, —$OR^E$, —$N(R^E)_2$, or —$SR^E$;

each $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a hydroxyl, amino, or thiol protecting group; or two $R^E$ groups of —$N(R^E)_2$ together form a substituted or unsubstituted 5- to 6-membered heterocyclic or heteroaromatic ring; and $R^f$ is a bond to the linker moiety; hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; an amino protecting group; or a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

26. The peptide of claim 25, wherein

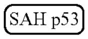

comprises the sequence $QSQQTFR_8NLWRLLS_5QN$ (SEQ ID NO: 29).

27. The peptide of claim 25, wherein

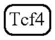

comprises the sequence $DELISFKDEGEQE(\beta Ala)_2ERDLS_5DVKS_5SLVN$ (SEQ ID NO: 30) or $DELISFKDEGEQE(\beta Ala)_2ER_8DLADVKS_5SLVN$ (SEQ ID NO: 31), wherein βAla is β-alanine.

28. The peptide of claim 25, wherein  is a linker comprising 2, 3, or 4 aminohexanoic acid residues.

29. The peptide of claim 25, having the sequence $DELISFKDEGEQE(\beta Ala)_2ERDLS_5DVKS_5SLVN(Ahx)_n QSQQTFR_8NLWRLLS_5QN$ (SEQ ID NO: 15) or $DELISFKDEGEQE(\beta Ala)_2ER_8DLADVKS_5SLVN(Ahx)_n QSQQTFR_8NLWRLLS_5QN$ (SEQ ID NO: 16), wherein βAla is β-alanine, Ahx is aminohexanoic acid, and n is 2, 3, or 4.

30. The peptide of claim 1, having the Formula (IV):

Formula (IV)

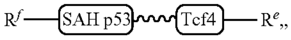

wherein

Tcf4 is a stapled Tcf4 or a derivative thereof;

SAH p53 is a stapled alpha-helix of p53 or a derivative thereof;

∿∿∿ is a linker moiety;

$R^e$ is a bond to the linker moiety, —$R^E$, —$OR^E$, —$N(R^E)_2$, or —$SR^E$;

each $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a hydroxyl, amino, or thiol protecting group; or two $R^E$ groups of —$N(R^E)_2$ together form a substituted or unsubstituted 5- to 6-membered heterocyclic or heteroaromatic ring; and $R^f$ is a bond to the linker moiety; hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; an amino protecting group; or a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

31. The peptide of claim 30, wherein

SAH p53 comprises the sequence QSQQTFR$_8$NLWRLLS$_5$QN (SEQ ID NO: 29).

32. The peptide of claim 30, wherein

Tcf4 comprises the sequence DELISFKDEGEQE(βAla)$_2$ERDLS$_5$DVKS$_5$SLVN (SEQ ID NO: 30) or DELISFKDEGEQE(βAla)$_2$ER$_8$DLADVKS$_5$SLVN (SEQ ID NO: 31), wherein βAla is β-alanine.

33. The peptide of claim 30, wherein ∿∿∿ is a linker comprising 2, 3, or 4 aminohexanoic acid residues.

34. The peptide of claim 30, having the sequence QSQQTFR$_8$NLWRLLS$_5$QN(Ahx)$_n$DELISFKDEGEQE(βAla)$_2$ERDLS$_5$DVKS$_5$SLVN (SEQ ID NO: 13) or QSQQTFR$_8$NLWRLLS$_5$QN(Ahx)$_n$DELISFKDEGEQE(βAla)$_2$ER$_8$DLADVKS$_5$SLVN (SEQ ID NO: 14), wherein βAla is β-alanine, Ahx is aminohexanoic acid, and n is 2, 3, or 4.

35. The peptide of claim 1, having the Formula (V):

Formula (V)

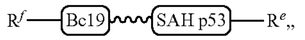

wherein

Bcl9 is a stapled Bcl9 or a derivative thereof;

SAH p53 is a stapled alpha-helix of p53 or a derivative thereof;

∿∿∿ is a linker moiety;

$R^e$ is a bond to the linker moiety, —$R^E$, —$OR^E$, —N(RE)$_2$, or —$SR^E$;

each $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a hydroxyl, amino, or thiol protecting group; or two $R^E$ groups of —$N(R^E)_2$ together form a substituted or unsubstituted 5- to 6-membered heterocyclic or heteroaromatic ring; and $R^f$ is a bond to the linker moiety; hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; an amino protecting group; or a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

36. The peptide of claim 35, wherein

SAH p53 comprises the sequence QSQQTFR$_8$NLWRLLS$_5$QN (SEQ ID NO: 29).

37. The peptide of claim 35, wherein  is a linker comprising 2, 3, or 4 aminohexanoic acid residues.

38. The peptide of claim 35, wherein

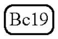

comprises the sequence SQEQLR$_8$HRERSLS$_5$TLRDIQRMLF (SEQ ID NO: 32), SQEQLEHRERSLS$_5$TLRS$_5$IQRMLF (SEQ ID NO: 33), or SQEQLEHRS$_5$RSLS$_5$TLRDIQRMLF (SEQ ID NO: 34).

39. The peptide of claim 35, having the sequence SQEQLR$_8$HRERSLS$_5$TLRDIQRMLF(Ahx)$_n$ QSQQTFR$_8$NLWRLLS$_5$QN (SEQ ID NO:4), SQEQLEHRERSLS$_5$TLRS$_5$IQRMLF(Ahx)$_n$ QSQQTFR$_8$NLWRLLS$_5$QN (SEQ ID NO: 5), or SQEQLEHRS$_5$RSLS$_5$TLRDIQRMLF(Ahx)$_n$ QSQQTFR$_8$NLWRLLS$_5$QN (SEQ ID NO: 6), wherein Ahx is aminohexanoic acid, and n is 2, 3, or 4.

40. The peptide of claim 1, having the Formula (VI):

Formula (VI)

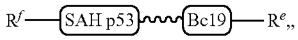

wherein

is a stapled Bcl9 or a derivative thereof;

is a stapled alpha-helix of p53 or a derivative thereof;

is a linker moiety;

R$^e$ is a bond to the linker moiety, —R$^E$, —OR$^E$, —N(R$^E$)$_2$, or —SR$^E$;

each R$^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a hydroxyl, amino, or thiol protecting group; or two R$^E$ groups of —N(R$^E$)$_2$ together form a substituted or unsubstituted 5- to 6-membered heterocyclic or heteroaromatic ring; and R$^f$ is a bond to the linker moiety; hydrogen; a cyclic or acyclic, branched or unbranched, substituted or unsubstituted aliphatic; a cyclic or acyclic, branched or unbranched, substituted or unsubstituted heteroaliphatic; a substituted or unsubstituted aryl; a substituted or unsubstituted heteroaryl; a substituted or unsubstituted acyl; a resin; an amino protecting group; or a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene.

41. The peptide of claim 40, having the sequence:

(SEQ ID NO: 1)
QSQQTFR$_8$NLWRLLS$_5$QN(Ahx)$_n$SQEQLR$_8$HRERSLS$_5$TLRDIQRMLF, (SEQ ID NO: 2)
QSQQTFR$_8$NLWRLLS$_5$QN(Ahx)$_n$SQEQLEHRERSLS$_5$TLRS$_5$IQRMLF,
or (SEQ ID NO: 3)
QSQQTFR$_8$NLWRLLS$_5$QN(Ahx)$_n$SQEQLEHRS$_5$RSLS$_5$TLRDIQRMLF;

wherein Ahx is aminohexanoic acid, and n is 2, 3, or 4.

42. A composition comprising the peptide of claim 1, and an excipient.

43. A method of treating a cancer in a subject in need thereof, the method comprising administering a therapeutically effective amount of the peptide of claim 1, to the subject in need thereof;

wherein the cancer is selected from the group consisting of carcinoma, sarcoma, metastatic cancer, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, Kaposi's sarcoma, and any combination thereof.

44. The peptide of claim 1, wherein the targeting domain is a ligand for Sin3.

45. The peptide of claim 44, wherein the ligand for Sin3 is a stapled Sin3 interacting domain (SID) of Mad1 or a derivative thereof.

46. The peptide of claim 45, wherein the stapled Sin3 interacting domain (SID) of Mad1 comprises the sequence:

VRMNIQMLLEAADYLERREREAEH; (SEQ ID NO: 85)
or

VRMNIQMLLEAADYLERRER. (SEQ ID NO: 86)

47. The peptide of claim 45, wherein the stapled Sin3 interacting domain (SID) of Mad1 comprises the sequence:

```
βAla-VRRRI S5MLLS5AANYLER;      (SEQ ID NO: 88)
or

βAla-VRRRIQMLLEAANKS5ERRS5R;    (SEQ ID NO: 91)
```

wherein the non-natural amino acids $S_5$ are cross-linked.

48. The peptide of claim 1, wherein the effector domain is a stapled, truncated MLL.

49. The peptide of claim 1, wherein the effector domain is a stapled, truncated cMyb.

50. The peptide of claim 48, wherein the effector domain comprises the sequence:

```
ILP*DIM*FVLKNT,       (SEQ ID NO: 81)

ILP*RIM*FVLKNT,       (SEQ ID NO: 82)

ILPSDIM*FVL*NT,       (SEQ ID NO: 83)
or

ILPSRIM*FVL*NT;       (SEQ ID NO: 84)
```

wherein "*" are non-natural amino acids that are cross-linked.

51. The peptide of claim 49, wherein the effector domain comprises the sequence:

```
K*KRI*ELELLLMSTENELKG,     (SEQ ID NO: 73)

K*KRI*RLELLLMSTENELKG,     (SEQ ID NO: 74)

KE*RIK*LELLLMSTENELKG,     (SEQ ID NO: 75)

KR*RIK*LELLLMSTENELKG,     (SEQ ID NO: 76)

KE*RIKELE*LLMSTENELKG,     (SEQ ID NO: 77)

KE*RIKRLE*LLMSTENELKG,     (SEQ ID NO: 78)

KR*RIKELE*LLMSTENELKG,     (SEQ ID NO: 79)
or

KEKRIKELELLLMSTE*ELK*;     (SEQ ID NO: 80)
```

wherein "*" are non-natural amino acids that are cross-linked.

52. The peptide of claim 3, wherein $R^a$ is hydrogen.

53. The peptide of claim 3, wherein $R^b$ is hydrogen.

54. The peptide of claim 3, wherein $R^b$ is alkyl.

55. The peptide of claim 3, wherein $R^b$ is methyl.

56. The peptide of claim 1, having the sequence QSQQTFR8NLWRLLS$_5$QN(Ahx)$_2$NPES$_5$ ILDS$_5$HVQRVMR (SEQ ID NO: 26), wherein Ahx is aminohexanoic acid.

* * * * *

SEQUENCE LISTING

```
<160> NUMBER OF SEQ ID NOS: 99

<210> SEQ ID NO 1
<211> LENGTH: 40
<212> TYPE: PRT
<213> ORGANISM: Artificial Sequence
<220> FEATURE:
<223> OTHER INFORMATION: bifunctional SAH p53-8 - Bcl-9 synthetic
      peptide
<220> FEATURE:
```

-continued

<221> NAME/KEY: MISC_FEATURE
<222> LOCATION: (7)..(7)
<223> OTHER INFORMATION: (R)-2-amino-2-methyldec-9-enoic acid or a
stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (17)..(17)
<223> OTHER INFORMATION: aminohexanoic acid linker
<220> FEATURE:
<221> NAME/KEY: MISC_FEATURE
<222> LOCATION: (23)..(23)
<223> OTHER INFORMATION: (R)-2-amino-2-methyldec-9-enoic acid or a
stapled derivative thereof
<220> FEATURE:
<221> NAME/KEY: MISC_FEATURE
<222> LOCATION: (30)..(30)
<223> OTHER INFORMATION: (S)-2-amino-2-methylhept-6-enoic acid or a
stapled derivative thereof

<400> SEQUENCE: 1

```
Gln Ser Gln Gln Thr Phe Xaa Asn Leu Trp Arg Leu Leu Xaa Gln Asn
1               5                   10                  15

Xaa Ser Gln Glu Gln Leu Xaa His Arg Glu Arg Ser Leu Xaa Thr Leu
            20                  25                  30

Arg Asp Ile Gln Arg Met Leu Phe
        35                  40
```

<210> SEQ ID NO 2
<211> LENGTH: 40
<212> TYPE: PRT
<213> ORGANISM: Artificial Sequence
<220> FEATURE:
<223> OTHER INFORMATION: bifunctional SAH p53-8 - Bcl-9 synthetic
peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a
stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (17)..(17)
<223> OTHER INFORMATION: aminohexanoic acid linker
<220> FEATURE:
<221> NAME/KEY: MISC_FEATURE
<222> LOCATION: (30)..(30)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (34)..(34)
<223> OTHER INFORMATION: (S)-2-amino-2-methylhept-6-enoic acid or a
stapled derivative thereof

<400> SEQUENCE: 2

```
Gln Ser Gln Gln Thr Phe Xaa Asn Leu Trp Arg Leu Leu Xaa Gln Asn
1               5                   10                  15

Xaa Ser Gln Glu Gln Leu Glu His Arg Glu Arg Ser Leu Xaa Thr Leu
            20                  25                  30

Arg Xaa Ile Gln Arg Met Leu Phe
        35                  40
```

-continued

<210> SEQ ID NO 3
<211> LENGTH: 40
<212> TYPE: PRT
<213> ORGANISM: Artificial Sequence
<220> FEATURE:
<223> OTHER INFORMATION: bifunctional SAH p53-8 - Bcl-9 synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: aminohexanoic acid linker
<220> FEATURE:
<221> NAME/KEY: MISC_FEATURE
<222> LOCATION: (26)..(26)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (30)..(30)
<223> OTHER INFORMATION: (S)-2-amino-2-methylhept-6-enoic acid or a stapled derivative thereof

<400> SEQUENCE: 3

```
Gln Ser Gln Gln Thr Phe Xaa Asn Leu Trp Arg Leu Leu Xaa Gln Asn
1               5                   10                  15

Xaa Ser Gln Glu Gln Leu Glu His Arg Xaa Arg Ser Leu Xaa Thr Leu
            20                  25                  30

Arg Asp Ile Gln Arg Met Leu Phe
        35                  40
```

<210> SEQ ID NO 4
<211> LENGTH: 40
<212> TYPE: PRT
<213> ORGANISM: Artificial Sequence
<220> FEATURE:
<223> OTHER INFORMATION: bifunctional Bcl-9 - SAH p53-8 synthetic peptide
<220> FEATURE:
<221> NAME/KEY: MISC_FEATURE
<222> LOCATION: (6)..(6)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: aminohexanoic acid linker
<220> FEATURE:
<221> NAME/KEY: MISC_FEATURE
<222> LOCATION: (31)..(31)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (38)..(38)
<223> OTHER INFORMATION: (S)-2-amino-2-methylhept-6-enoic acid or a stapled derivative thereof

<400> SEQUENCE: 4

-continued

Ser Gln Glu Gln Leu Xaa His Arg Glu Arg Ser Leu Xaa Thr Leu Arg
1               5                   10                  15

Asp Ile Gln Arg Met Leu Phe Xaa Gln Ser Gln Gln Thr Phe Xaa Asn
            20                  25                  30

Leu Trp Arg Leu Leu Xaa Gln Asn
        35                  40

<210> SEQ ID NO 5
<211> LENGTH: 40
<212> TYPE: PRT
<213> ORGANISM: Artificial Sequence
<220> FEATURE:
<223> OTHER INFORMATION: bifunctional Bcl-9 - SAH p53-8 synthetic peptide
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: aminohexanoic acid linker
<220> FEATURE:
<221> NAME/KEY: MISC_FEATURE
<222> LOCATION: (31)..(31)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (38)..(38)
<223> OTHER INFORMATION: (S)-2-amino-2-methylhept-6-enoic acid or a stapled derivative thereof

<400> SEQUENCE: 5

Ser Gln Glu Gln Leu Glu His Arg Glu Arg Ser Leu Xaa Thr Leu Arg
1               5                   10                  15

Xaa Ile Gln Arg Met Leu Phe Xaa Gln Ser Gln Gln Thr Phe Xaa Asn
            20                  25                  30

Leu Trp Arg Leu Leu Xaa Gln Asn
        35                  40

<210> SEQ ID NO 6
<211> LENGTH: 40
<212> TYPE: PRT
<213> ORGANISM: Artificial Sequence
<220> FEATURE:
<223> OTHER INFORMATION: bifunctional Bcl-9 - SAH p53-8 synthetic peptide
<220> FEATURE:
<221> NAME/KEY: MISC_FEATURE
<222> LOCATION: (9)..(9)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: aminohexanoic acid linker
<220> FEATURE:
<221> NAME/KEY: MISC_FEATURE
<222> LOCATION: (31)..(31)
<223> OTHER INFORMATION: (R)-2-amino-2-methyldec-9-enoic acid or a

```
      stapled derivative thereof
<220> FEATURE:
<221> NAME/KEY: MISC_FEATURE
<222> LOCATION: (38)..(38)
<223> OTHER INFORMATION: (S)-2-amino-2-methylhept-6-enoic acid or a
      stapled derivative thereof

<400> SEQUENCE: 6

Ser Gln Glu Gln Leu Glu His Arg Xaa Arg Ser Leu Xaa Thr Leu Arg
1               5                   10                  15

Asp Ile Gln Arg Met Leu Phe Xaa Gln Ser Gln Gln Thr Phe Xaa Asn
            20                  25                  30

Leu Trp Arg Leu Leu Xaa Gln Asn
        35                  40


<210> SEQ ID NO 7
<211> LENGTH: 40
<212> TYPE: PRT
<213> ORGANISM: Artificial Sequence
<220> FEATURE:
<223> OTHER INFORMATION: bifunctional SAH p53-8 - Bcl-9 synthetic
      peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (17)..(17)
<223> OTHER INFORMATION: polyethylene glycol linker
<220> FEATURE:
<221> NAME/KEY: MISC_FEATURE
<222> LOCATION: (30)..(30)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (34)..(34)
<223> OTHER INFORMATION: (S)-2-amino-2-methylhept-6-enoic acid or a
      stapled derivative thereof

<400> SEQUENCE: 7

Gln Ser Gln Gln Thr Phe Xaa Asn Leu Trp Arg Leu Leu Xaa Gln Asn
1               5                   10                  15

Xaa Ser Gln Glu Gln Leu Glu His Arg Glu Arg Ser Leu Xaa Thr Leu
            20                  25                  30

Arg Xaa Ile Gln Arg Met Leu Phe
        35                  40


<210> SEQ ID NO 8
<211> LENGTH: 40
<212> TYPE: PRT
<213> ORGANISM: Artificial Sequence
<220> FEATURE:
<223> OTHER INFORMATION: bifunctional SAH p53-8 - Bcl-9 synthetic
      peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a
```

stapled derivative thereof
<220> FEATURE:
<221> NAME/KEY: MISC_FEATURE
<222> LOCATION: (17)..(17)
<223> OTHER INFORMATION: polyethylene glycol linker
<220> FEATURE:
<221> NAME/KEY: MISC_FEATURE
<222> LOCATION: (30)..(30)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (34)..(34)
<223> OTHER INFORMATION: (S)-2-amino-2-methylhept-6-enoic acid or a stapled derivative thereof

<400> SEQUENCE: 8

```
Gln Ser Gln Gln Thr Phe Xaa Asn Leu Trp Arg Leu Leu Xaa Gln Asn
1               5                   10                  15

Xaa Ser Gln Glu Gln Leu Glu His Arg Glu Arg Ser Leu Xaa Thr Leu
            20                  25                  30

Arg Xaa Ile Gln Arg Met Leu Phe
        35                  40
```

<210> SEQ ID NO 9
<211> LENGTH: 40
<212> TYPE: PRT
<213> ORGANISM: Artificial Sequence
<220> FEATURE:
<223> OTHER INFORMATION: bifunctional SAH p53-8 - Bcl-9 synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: polyethylene glycol linker
<220> FEATURE:
<221> NAME/KEY: MISC_FEATURE
<222> LOCATION: (26)..(26)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (30)..(30)
<223> OTHER INFORMATION: (S)-2-amino-2-methylhept-6-enoic acid or a stapled derivative thereof

<400> SEQUENCE: 9

```
Gln Ser Gln Gln Thr Phe Xaa Asn Leu Trp Arg Leu Leu Xaa Gln Asn
1               5                   10                  15

Xaa Ser Gln Glu Gln Leu Glu His Arg Xaa Arg Ser Leu Xaa Thr Leu
            20                  25                  30

Arg Asp Ile Gln Arg Met Leu Phe
        35                  40
```

<210> SEQ ID NO 10
<211> LENGTH: 40
<212> TYPE: PRT
<213> ORGANISM: Artificial Sequence
<220> FEATURE:
<223> OTHER INFORMATION: bifunctional  Bcl-9 - SAH p53-8 synthetic peptide
<220> FEATURE:
<221> NAME/KEY: MISC_FEATURE
<222> LOCATION: (6)..(6)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: polyethylene glycol linker
<220> FEATURE:
<221> NAME/KEY: MISC_FEATURE
<222> LOCATION: (31)..(31)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (38)..(38)
<223> OTHER INFORMATION: (S)-2-amino-2-methylhept-6-enoic acid or a stapled derivative thereof

<400> SEQUENCE: 10

```
Ser Gln Glu Gln Leu Xaa His Arg Glu Arg Ser Leu Xaa Thr Leu Arg
1               5                   10                  15

Asp Ile Gln Arg Met Leu Phe Xaa Gln Ser Gln Gln Thr Phe Xaa Asn
            20                  25                  30

Leu Trp Arg Leu Leu Xaa Gln Asn
        35                  40
```

<210> SEQ ID NO 11
<211> LENGTH: 40
<212> TYPE: PRT
<213> ORGANISM: Artificial Sequence
<220> FEATURE:
<223> OTHER INFORMATION: bifunctional Bcl-9 - SAH p53-8 synthetic peptide
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: polyethylene glycol linker
<220> FEATURE:
<221> NAME/KEY: MISC_FEATURE
<222> LOCATION: (31)..(31)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (38)..(38)
<223> OTHER INFORMATION: (S)-2-amino-2-methylhept-6-enoic acid or a stapled derivative thereof

<400> SEQUENCE: 11

```
Ser Gln Glu Gln Leu Glu His Arg Glu Arg Ser Leu Xaa Thr Leu Arg
1               5                   10                  15

Xaa Ile Gln Arg Met Leu Phe Xaa Gln Ser Gln Gln Thr Phe Xaa Asn
            20                  25                  30

Leu Trp Arg Leu Leu Xaa Gln Asn
        35                  40
```

<210> SEQ ID NO 12
<211> LENGTH: 40
<212> TYPE: PRT
<213> ORGANISM: Artificial Sequence
<220> FEATURE:
<223> OTHER INFORMATION: bifunctional Bcl-9 - SAH p53-8 synthetic peptide
<220> FEATURE:
<221> NAME/KEY: MISC_FEATURE
<222> LOCATION: (9)..(9)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: polyethylene glycol linker
<220> FEATURE:
<221> NAME/KEY: MISC_FEATURE
<222> LOCATION: (31)..(31)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (38)..(38)
<223> OTHER INFORMATION: (S)-2-amino-2-methylhept-6-enoic acid or a stapled derivative thereof

<400> SEQUENCE: 12

```
Ser Gln Glu Gln Leu Glu His Arg Xaa Arg Ser Leu Xaa Thr Leu Arg
1               5                   10                  15

Asp Ile Gln Arg Met Leu Phe Xaa Gln Ser Gln Gln Thr Phe Xaa Asn
            20                  25                  30

Leu Trp Arg Leu Leu Xaa Gln Asn
        35                  40
```

<210> SEQ ID NO 13
<211> LENGTH: 45
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: aminohexanoic acid linker
<220> FEATURE:
<221> NAME/KEY: MISC_FEATURE
<222> LOCATION: (31)..(31)
<223> OTHER INFORMATION: beta-alanine
<220> FEATURE:
<221> NAME/KEY: MISC_FEATURE
<222> LOCATION: (32)..(32)
<223> OTHER INFORMATION: beta-alanine
<220> FEATURE:
<221> NAME/KEY: MISC_FEATURE
<222> LOCATION: (37)..(37)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (41)..(41)
<223> OTHER INFORMATION: (S)-2-amino-2-methylhept-6-enoic acid or a stapled derivative thereof

<400> SEQUENCE: 13

```
Gln Ser Gln Gln Thr Phe Xaa Asn Leu Trp Arg Leu Leu Xaa Gln Asn
1               5                   10                  15

Xaa Asp Glu Leu Ile Ser Phe Lys Asp Glu Gly Glu Gln Glu Xaa Xaa
            20                  25                  30

Glu Arg Asp Leu Xaa Asp Val Lys Xaa Ser Leu Val Asn
        35                  40                  45
```

<210> SEQ ID NO 14
<211> LENGTH: 45
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: aminohexanoic acid linker
<220> FEATURE:
<221> NAME/KEY: MISC_FEATURE
<222> LOCATION: (31)..(31)
<223> OTHER INFORMATION: beta-alanine
<220> FEATURE:
<221> NAME/KEY: MISC_FEATURE
<222> LOCATION: (32)..(32)
<223> OTHER INFORMATION: beta-alanine
<220> FEATURE:
<221> NAME/KEY: MISC_FEATURE
<222> LOCATION: (34)..(34)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (41)..(41)
<223> OTHER INFORMATION: (S)-2-amino-2-methylhept-6-enoic acid or a stapled derivative thereof

<400> SEQUENCE: 14

```
Gln Ser Gln Gln Thr Phe Xaa Asn Leu Trp Arg Leu Leu Xaa Gln Asn
1               5                   10                  15

Xaa Asp Glu Leu Ile Ser Phe Lys Asp Glu Gly Glu Gln Glu Xaa Xaa
            20                  25                  30

Glu Xaa Asp Leu Ala Asp Val Lys Xaa Ser Leu Val Asn
        35                  40                  45
```

<210> SEQ ID NO 15
<211> LENGTH: 45
<212> TYPE: PRT
<213> ORGANISM: Artificial Sequence
<220> FEATURE:
<223> OTHER INFORMATION: bifunctional Tcf4 - SAH p53-8 synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (20)..(20)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (29)..(29)
<223> OTHER INFORMATION: aminohexanoic acid linker
<220> FEATURE:
<221> NAME/KEY: MISC_FEATURE
<222> LOCATION: (36)..(36)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (43)..(43)
<223> OTHER INFORMATION: (S)-2-amino-2-methylhept-6-enoic acid or a stapled derivative thereof

<400> SEQUENCE: 15

```
Asp Glu Leu Ile Ser Phe Lys Asp Glu Gly Glu Gln Glu Xaa Xaa Glu
1               5                   10                  15

Arg Asp Leu Xaa Asp Val Lys Xaa Ser Leu Val Asn Xaa Gln Ser Gln
            20                  25                  30

Gln Thr Phe Xaa Asn Leu Trp Arg Leu Leu Xaa Gln Asn
        35                  40                  45
```

<210> SEQ ID NO 16
<211> LENGTH: 45
<212> TYPE: PRT
<213> ORGANISM: Artificial Sequence
<220> FEATURE:
<223> OTHER INFORMATION: bifunctional Tcf4 - SAH p53-8 synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (17)..(17)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (29)..(29)
<223> OTHER INFORMATION: aminohexanoic acid linker
<220> FEATURE:
<221> NAME/KEY: MISC_FEATURE
<222> LOCATION: (36)..(36)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (43)..(43)
<223> OTHER INFORMATION: (S)-2-amino-2-methylhept-6-enoic acid or a stapled derivative thereof

<400> SEQUENCE: 16

```
Asp Glu Leu Ile Ser Phe Lys Asp Glu Gly Glu Gln Glu Xaa Xaa Glu
1               5                   10                  15

Xaa Asp Leu Ala Asp Val Lys Xaa Ser Leu Val Asn Xaa Gln Ser Gln
            20                  25                  30
```

-continued

Gln Thr Phe Xaa Asn Leu Trp Arg Leu Leu Xaa Gln Asn
        35                  40                  45

<210> SEQ ID NO 17
<211> LENGTH: 45
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: polyethylene glycol linker
<220> FEATURE:
<221> NAME/KEY: MISC_FEATURE
<222> LOCATION: (31)..(32)
<223> OTHER INFORMATION: beta-alanine
<220> FEATURE:
<221> NAME/KEY: MISC_FEATURE
<222> LOCATION: (37)..(37)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (41)..(41)
<223> OTHER INFORMATION: (S)-2-amino-2-methylhept-6-enoic acid or a stapled derivative thereof

<400> SEQUENCE: 17

Gln Ser Gln Gln Thr Phe Xaa Asn Leu Trp Arg Leu Leu Xaa Gln Asn
1               5                   10                  15

Xaa Asp Glu Leu Ile Ser Phe Lys Asp Glu Gly Glu Gln Glu Xaa Xaa
            20                  25                  30

Glu Arg Asp Leu Xaa Asp Val Lys Xaa Ser Leu Val Asn
        35                  40                  45

<210> SEQ ID NO 18
<211> LENGTH: 45
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: polyethylene glycol linker
<220> FEATURE:
<221> NAME/KEY: MISC_FEATURE
<222> LOCATION: (31)..(32)
<223> OTHER INFORMATION: beta-alanine
<220> FEATURE:
<221> NAME/KEY: MISC_FEATURE
<222> LOCATION: (34)..(34)

<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (41)..(41)
<223> OTHER INFORMATION: (S)-2-amino-2-methylhept-6-enoic acid or a
      stapled derivative thereof

<400> SEQUENCE: 18

```
Gln Ser Gln Gln Thr Phe Xaa Asn Leu Trp Arg Leu Leu Xaa Gln Asn
1               5                   10                  15

Xaa Asp Glu Leu Ile Ser Phe Lys Asp Glu Gly Glu Gln Glu Xaa Xaa
            20                  25                  30

Glu Xaa Asp Leu Ala Asp Val Lys Xaa Ser Leu Val Asn
        35                  40                  45
```

<210> SEQ ID NO 19
<211> LENGTH: 45
<212> TYPE: PRT
<213> ORGANISM: Artificial Sequence
<220> FEATURE:
<223> OTHER INFORMATION: bifunctional Tcf4 - SAH p53-8 synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (20)..(20)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (29)..(29)
<223> OTHER INFORMATION: polyethylene glycol linker
<220> FEATURE:
<221> NAME/KEY: MISC_FEATURE
<222> LOCATION: (36)..(36)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (43)..(43)
<223> OTHER INFORMATION: (S)-2-amino-2-methylhept-6-enoic acid or a
      stapled derivative thereof

<400> SEQUENCE: 19

```
Asp Glu Leu Ile Ser Phe Lys Asp Glu Gly Glu Gln Glu Xaa Xaa Glu
1               5                   10                  15

Arg Asp Leu Xaa Asp Val Lys Xaa Ser Leu Val Asn Xaa Gln Ser Gln
            20                  25                  30

Gln Thr Phe Xaa Asn Leu Trp Arg Leu Leu Xaa Gln Asn
        35                  40                  45
```

<210> SEQ ID NO 20
<211> LENGTH: 45
<212> TYPE: PRT
<213> ORGANISM: Artificial Sequence
<220> FEATURE:
<223> OTHER INFORMATION: bifunctional Tcf4 - SAH p53-8 synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE -continued
<222> LOCATION: (17)..(17)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (29)..(29)
<223> OTHER INFORMATION: polyethylene glycol linker
<220> FEATURE:
<221> NAME/KEY: MISC_FEATURE
<222> LOCATION: (36)..(36)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (43)..(43)
<223> OTHER INFORMATION: (S)-2-amino-2-methylhept-6-enoic acid or a
      stapled derivative thereof

<400> SEQUENCE: 20

```
Asp Glu Leu Ile Ser Phe Lys Asp Glu Gly Glu Gln Glu Xaa Xaa Glu
1               5                   10                  15

Xaa Asp Leu Ala Asp Val Lys Xaa Ser Leu Val Asn Xaa Gln Ser Gln
            20                  25                  30

Gln Thr Phe Xaa Asn Leu Trp Arg Leu Leu Xaa Gln Asn
        35                  40                  45
```

<210> SEQ ID NO 21
<211> LENGTH: 29
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (15)..(16)
<223> OTHER INFORMATION: beta-alanine
<220> FEATURE:
<221> NAME/KEY: MISC_FEATURE
<222> LOCATION: (21)..(21)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (25)..(25)
<223> OTHER INFORMATION: (S)-2-amino-2-methylhept-6-enoic acid or a
      stapled derivative thereof

<400> SEQUENCE: 21

```
Cys Asp Glu Leu Ile Ser Phe Lys Asp Glu Gly Glu Gln Glu Xaa Xaa
1               5                   10                  15

Glu Arg Asp Leu Xaa Asp Val Lys Xaa Ser Leu Val Asn
            20                  25
```

<210> SEQ ID NO 22
<211> LENGTH: 29
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (15)..(16)
<223> OTHER INFORMATION: beta-alanine
<220> FEATURE:
<221> NAME/KEY: MISC_FEATURE
<222> LOCATION: (18)..(18)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (25)..(25)
<223> OTHER INFORMATION: (S)-2-amino-2-methylhept-6-enoic acid or a
stapled derivative thereof

<400> SEQUENCE: 22

Cys Asp Glu Leu Ile Ser Phe Lys Asp Glu Gly Glu Gln Glu Xaa Xaa
1 5 10 15

Glu Xaa Asp Leu Ala Asp Val Lys Xaa Ser Leu Val Asn
20 25

<210> SEQ ID NO 23
<211> LENGTH: 29
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (20)..(20)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a
stapled derivative thereof

<400> SEQUENCE: 23

Asp Glu Leu Ile Ser Phe Lys Asp Glu Gly Glu Gln Glu Xaa Xaa Glu
1 5 10 15

Arg Asp Leu Xaa Asp Val Lys Xaa Ser Leu Val Asn Cys
20 25

<210> SEQ ID NO 24
<211> LENGTH: 29
<212> TYPE: PRT
<213> ORGANISM: Artificial Sequence
<220> FEATURE:
<223> OTHER INFORMATION: bifunctional SAH p53-8 - Tcf4 synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (17)..(17)
<223> OTHER INFORMATION: (R)-2-amino-2-methyldec-9-enoic acid or a
stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a
stapled derivative thereof

<400> SEQUENCE: 24

Asp Glu Leu Ile Ser Phe Lys Asp Glu Gly Glu Gln Glu Xaa Xaa Glu
1 5 10 15

Xaa Asp Leu Ala Asp Val Lys Xaa Ser Leu Val Asn Cys
20 25

<210> SEQ ID NO 25
<211> LENGTH: 16
<212> TYPE: PRT

<213> ORGANISM: Homo sapiens

<400> SEQUENCE: 25

Glu Asn Pro Glu Ser Ile Leu Asp Glu His Val Gln Arg Val Met Arg
1 5 10 15

<210> SEQ ID NO 26
<211> LENGTH: 15
<212> TYPE: PRT
<213> ORGANISM: Artificial Sequence
<220> FEATURE:
<223> OTHER INFORMATION: Axin-derived synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof

<400> SEQUENCE: 26

Asn Pro Glu Xaa Ile Leu Asp Xaa His Val Gln Arg Val Met Arg
1 5 10 15

<210> SEQ ID NO 27
<211> LENGTH: 15
<212> TYPE: PRT
<213> ORGANISM: Artificial Sequence
<220> FEATURE:
<223> OTHER INFORMATION: Axin-derived synthetic peptide
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a stapled derivative thereof

<400> SEQUENCE: 27

Asn Pro Glu Ser Ile Leu Asp Xaa His Val Gln Xaa Val Met Arg
1 5 10 15

<210> SEQ ID NO 28
<211> LENGTH: 15
<212> TYPE: PRT
<213> ORGANISM: Artificial Sequence
<220> FEATURE:
<223> OTHER INFORMATION: Axin-derived synthetic peptide
<220> FEATURE:
<221> NAME/KEY: MISC_FEATURE
<222> LOCATION: (4)..(4)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (11)..(11)
<223> OTHER INFORMATION: (R)-2-amino-2-methylhept-6-enoic acid or a stapled derivative thereof

<400> SEQUENCE: 28

Asn Pro Glu Xaa Ile Leu Asp Glu His Val Xaa Arg Val Met Arg
1 5 10 15

<210> SEQ ID NO 29
<211> LENGTH: 16

<212> TYPE: PRT
<213> ORGANISM: Artificial Sequence
<220> FEATURE:
<223> OTHER INFORMATION: SAH p53-derived synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof

<400> SEQUENCE: 29

```
Gln Ser Gln Gln Thr Phe Xaa Asn Leu Trp Arg Leu Leu Xaa Gln Asn
1               5                   10                  15
```

<210> SEQ ID NO 30
<211> LENGTH: 28
<212> TYPE: PRT
<213> ORGANISM: Artificial Sequence
<220> FEATURE:
<223> OTHER INFORMATION: Tcf4-derived synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (20)..(20)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a stapled derivative thereof

<400> SEQUENCE: 30

```
Asp Glu Leu Ile Ser Phe Lys Asp Glu Gly Glu Gln Glu Xaa Xaa Glu
1               5                   10                  15

Arg Asp Leu Xaa Asp Val Lys Xaa Ser Leu Val Asn
            20                  25
```

<210> SEQ ID NO 31
<211> LENGTH: 28
<212> TYPE: PRT
<213> ORGANISM: Artificial Sequence
<220> FEATURE:
<223> OTHER INFORMATION: Tcf4-derived synthetic peptide
<220> FEATURE:
<221> NAME/KEY: MISC_FEATURE
<222> LOCATION: (14)..(15)
<223> OTHER INFORMATION: beta-alanine
<220> FEATURE:
<221> NAME/KEY: MISC_FEATURE
<222> LOCATION: (17)..(17)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a stapled derivative thereof

<400> SEQUENCE: 31

```
Asp Glu Leu Ile Ser Phe Lys Asp Glu Gly Glu Gln Glu Xaa Xaa Glu
1               5                   10                  15

Xaa Asp Leu Ala Asp Val Lys Xaa Ser Leu Val Asn
            20                  25
```

-continued

<210> SEQ ID NO 32
<211> LENGTH: 23
<212> TYPE: PRT
<213> ORGANISM: Artificial Sequence
<220> FEATURE:
<223> OTHER INFORMATION: Bcl9-derived synthetic peptide
<220> FEATURE:
<221> NAME/KEY: MISC_FEATURE
<222> LOCATION: (6)..(6)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof

<400> SEQUENCE: 32

Ser Gln Glu Gln Leu Xaa His Arg Glu Arg Ser Leu Xaa Thr Leu Arg
1 5 10 15

Asp Ile Gln Arg Met Leu Phe
20

<210> SEQ ID NO 33
<211> LENGTH: 23
<212> TYPE: PRT
<213> ORGANISM: Artificial Sequence
<220> FEATURE:
<223> OTHER INFORMATION: Bcl9-derived synthetic peptide
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: (S)-2-amino-2-methylhept-6-enoic acid or a stapled derivative thereof

<400> SEQUENCE: 33

Ser Gln Glu Gln Leu Glu His Arg Glu Arg Ser Leu Xaa Thr Leu Arg
1 5 10 15

Xaa Ile Gln Arg Met Leu Phe
20

<210> SEQ ID NO 34
<211> LENGTH: 23
<212> TYPE: PRT
<213> ORGANISM: Artificial Sequence
<220> FEATURE:
<223> OTHER INFORMATION: Bcl9-derived synthetic peptide
<220> FEATURE:
<221> NAME/KEY: MISC_FEATURE
<222> LOCATION: (9)..(9)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof

<400> SEQUENCE: 34

Ser Gln Glu Gln Leu Glu His Arg Xaa Arg Ser Leu Xaa Thr Leu Arg
1 5 10 15

Asp Ile Gln Arg Met Leu Phe
20

<210> SEQ ID NO 35
<211> LENGTH: 15
<212> TYPE: PRT
<213> ORGANISM: Homo sapiens

<400> SEQUENCE: 35

Leu Ser Gln Glu Thr Phe Ser Asp Leu Trp Lys Leu Leu Pro Glu
1 5 10 15

<210> SEQ ID NO 36
<211> LENGTH: 15
<212> TYPE: PRT
<213> ORGANISM: Artificial Sequence
<220> FEATURE:
<223> OTHER INFORMATION: effector domain synthetic peptide
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a stapled derivative thereof

<400> SEQUENCE: 36

Leu Ser Gln Glu Thr Phe Ser Xaa Leu Trp Lys Xaa Leu Pro Glu
1 5 10 15

<210> SEQ ID NO 37
<211> LENGTH: 16
<212> TYPE: PRT
<213> ORGANISM: Artificial Sequence
<220> FEATURE:
<223> OTHER INFORMATION: effector domain synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof

<400> SEQUENCE: 37

Gln Ser Gln Gln Thr Phe Xaa Asn Leu Trp Arg Lys Lys Xaa Gln Asn
1 5 10 15

<210> SEQ ID NO 38
<211> LENGTH: 15
<212> TYPE: PRT
<213> ORGANISM: Artificial Sequence
<220> FEATURE:
<223> OTHER INFORMATION: effector domain synthetic peptide
<220> FEATURE:
<221> NAME/KEY: MISC_FEATURE
<222> LOCATION: (7)..(7)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (11)..(11)
<223> OTHER INFORMATION: (S)-2-amino-2-methylhept-6-enoic acid or a stapled derivative thereof

<400> SEQUENCE: 38

Gln Ser Gln Gln Thr Phe Xaa Asn Leu Trp Xaa Lys Lys Gln Asn
1 5 10 15

-continued

<210> SEQ ID NO 39
<211> LENGTH: 15
<212> TYPE: PRT
<213> ORGANISM: Artificial Sequence
<220> FEATURE:
<223> OTHER INFORMATION: effector domain synthetic peptide
<220> FEATURE:
<221> NAME/KEY: MISC_FEATURE
<222> LOCATION: (8)..(8)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a
      stapled derivative thereof

<400> SEQUENCE: 39

Leu Ser Gln Asn Thr Phe Ser Xaa Leu Trp Lys Xaa Leu Pro Gln
1               5                   10                  15

<210> SEQ ID NO 40
<211> LENGTH: 10
<212> TYPE: PRT
<213> ORGANISM: Homo sapiens

<400> SEQUENCE: 40

Thr Pro Phe Tyr Ile Glu Asp Ile Leu Gly
1               5                   10

<210> SEQ ID NO 41
<211> LENGTH: 20
<212> TYPE: PRT
<213> ORGANISM: Homo sapiens

<400> SEQUENCE: 41

Val Arg Met Asn Ile Gln Met Leu Leu Glu Ala Ala Asp Tyr Leu Glu
1               5                   10                  15

Arg Arg Glu Arg
            20

<210> SEQ ID NO 42
<211> LENGTH: 8
<212> TYPE: PRT
<213> ORGANISM: Homo sapiens

<400> SEQUENCE: 42

Pro Lys Lys Lys Arg Lys Val Glu
1               5

<210> SEQ ID NO 43
<211> LENGTH: 18
<212> TYPE: PRT
<213> ORGANISM: Homo sapiens

<400> SEQUENCE: 43

Lys Arg Pro Ala Ala Thr Lys Lys Ala Gly Gln Ala Lys Lys Lys Lys
1               5                   10                  15

Leu Asp

<210> SEQ ID NO 44
<211> LENGTH: 9
<212> TYPE: PRT
<213> ORGANISM: Homo sapiens

-continued

<400> SEQUENCE: 44

Pro Ala Ala Lys Arg Val Lys Leu Asp
1               5

<210> SEQ ID NO 45
<211> LENGTH: 15
<212> TYPE: PRT
<213> ORGANISM: Homo sapiens

<400> SEQUENCE: 45

Leu Ser Gln Glu Thr Phe Ser Asp Leu Trp Lys Leu Leu Pro Glu
1               5                   10                  15

<210> SEQ ID NO 46
<211> LENGTH: 16
<212> TYPE: PRT
<213> ORGANISM: Homo sapiens

<400> SEQUENCE: 46

Met Leu Ser Pro Asp Asp Ile Glu Gln Trp Phe Thr Glu Asp Pro Gly
1               5                   10                  15

<210> SEQ ID NO 47
<211> LENGTH: 15
<212> TYPE: PRT
<213> ORGANISM: Homo sapiens

<400> SEQUENCE: 47

Ile Leu Pro Ser Asp Ile Met Asp Phe Val Leu Lys Asn Thr Pro
1               5                   10                  15

<210> SEQ ID NO 48
<211> LENGTH: 15
<212> TYPE: PRT
<213> ORGANISM: Homo sapiens

<400> SEQUENCE: 48

Leu Ala Ser Pro Glu Leu Glu Arg Leu Ile Ile Gln Ser Ser Asn
1               5                   10                  15

<210> SEQ ID NO 49
<211> LENGTH: 19
<212> TYPE: PRT
<213> ORGANISM: Homo sapiens

<400> SEQUENCE: 49

Tyr Ile Asp Gly Phe Val Ile Gly Ser Ala Leu Gln Phe Leu Ile Pro
1               5                   10                  15

Arg Leu Pro

<210> SEQ ID NO 50
<211> LENGTH: 21
<212> TYPE: PRT
<213> ORGANISM: Homo sapiens

<400> SEQUENCE: 50

Lys Glu Lys Arg Ile Lys Glu Leu Glu Leu Leu Leu Met Ser Thr Glu
1               5                   10                  15

Asn Glu Leu Lys Gly
            20

<210> SEQ ID NO 51
<211> LENGTH: 21

```
<212> TYPE: PRT
<213> ORGANISM: Homo sapiens

<400> SEQUENCE: 51

Ile Leu Ser Arg Arg Pro Ser Tyr Arg Lys Ile Leu Asn Asp Leu Ser
1               5                   10                  15

Ser Asp Ala Pro Gly
            20


<210> SEQ ID NO 52
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (11)..(11)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (15)..(15)
<223> OTHER INFORMATION: (S)-2-amino-2-methylhept-6-enoic acid or a
      stapled derivative thereof

<400> SEQUENCE: 52

Lys Glu Lys Arg Ile Lys Glu Leu Glu Leu Xaa Leu Met Ser Xaa Glu
1               5                   10                  15

Asn Glu Leu Lys Gly
            20


<210> SEQ ID NO 53
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (11)..(11)
<223> OTHER INFORMATION: (S)-2-amino-2-methylhept-6-enoic acid or a
      stapled derivative thereof

<400> SEQUENCE: 53

Lys Glu Lys Arg Ile Lys Xaa Leu Glu Leu Xaa Leu Met Ser Thr Glu
1               5                   10                  15

Asn Glu Leu Lys Gly
            20


<210> SEQ ID NO 54
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
```

-continued stapled derivative thereof

<400> SEQUENCE: 54

Lys Glu Xaa Arg Ile Lys Xaa Leu Glu Leu Leu Leu Met Ser Thr Glu
1 5 10 15

Asn Glu Leu Lys Gly
20

<210> SEQ ID NO 55
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a stapled derivative thereof

<400> SEQUENCE: 55

Lys Glu Lys Arg Ile Lys Xaa Leu Glu Leu Leu Leu Met Xaa Thr Glu
1 5 10 15

Asn Glu Leu Lys Gly
20

<210> SEQ ID NO 56
<211> LENGTH: 16
<212> TYPE: PRT
<213> ORGANISM: Artificial Sequence
<220> FEATURE:
<223> OTHER INFORMATION: MLL "E" domain synthetic peptide
<220> FEATURE:
<221> NAME/KEY: MISC_FEATURE
<222> LOCATION: (1)..(1)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (5)..(5)
<223> OTHER INFORMATION: (S)-2-amino-2-methylhept-6-enoic acid or a stapled derivative thereof

<400> SEQUENCE: 56

Xaa Ile Leu Pro Xaa Asp Ile Met Asp Phe Val Leu Lys Asn Thr Pro
1 5 10 15

<210> SEQ ID NO 57
<211> LENGTH: 15
<212> TYPE: PRT
<213> ORGANISM: Artificial Sequence
<220> FEATURE:
<223> OTHER INFORMATION: MLL "E" domain synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof

<400> SEQUENCE: 57

Ile Leu Pro Xaa Asp Ile Met Xaa Phe Val Leu Lys Asn Thr Pro
1 5 10 15

<210> SEQ ID NO 58
<211> LENGTH: 15
<212> TYPE: PRT
<213> ORGANISM: Artificial Sequence
<220> FEATURE:
<223> OTHER INFORMATION: MLL “E” domain synthetic peptide
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a stapled derivative thereof

<400> SEQUENCE: 58

Ile Leu Pro Ser Asp Ile Met Xaa Phe Val Leu Xaa Asn Thr Pro
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: MLL “E” domain synthetic peptide
<220> FEATURE:
<221> NAME/KEY: MISC_FEATURE
<222> LOCATION: (11)..(11)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (15)..(15)
<223> OTHER INFORMATION: (S)-2-amino-2-methylhept-6-enoic acid or a stapled derivative thereof

<400> SEQUENCE: 59

Ile Leu Pro Ser Asp Ile Met Asp Phe Val Xaa Lys Asn Thr Xaa
1 5 10 15

<210> SEQ ID NO 60
<211> LENGTH: 16
<212> TYPE: PRT
<213> ORGANISM: Artificial Sequence
<220> FEATURE:
<223> OTHER INFORMATION: MLL “E” domain synthetic peptide
<220> FEATURE:
<221> NAME/KEY: MISC_FEATURE
<222> LOCATION: (1)..(1)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof

<400> SEQUENCE: 60

Xaa Ile Leu Pro Ser Asp Ile Xaa Asp Phe Val Leu Lys Asn Thr Pro
1 5 10 15

<210> SEQ ID NO 61
<211> LENGTH: 21
<212> TYPE: PRT
<213> ORGANISM: Artificial Sequence
<220> FEATURE:
<223> OTHER INFORMATION: p-KID “E” domain synthetic peptide
<220> FEATURE:
<221> NAME/KEY: MISC_FEATURE
<222> LOCATION: (9)..(9)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof

<400> SEQUENCE: 61

```
Ile Leu Ser Arg Arg Pro Ser Tyr Xaa Lys Ile Leu Xaa Asp Leu Ser
1               5                   10                  15

Ser Asp Ala Pro Gly
            20
```

<210> SEQ ID NO 62
<211> LENGTH: 21
<212> TYPE: PRT
<213> ORGANISM: Artificial Sequence
<220> FEATURE:
<223> OTHER INFORMATION: p-KID "E" domain synthetic peptide
<220> FEATURE:
<221> NAME/KEY: MISC_FEATURE
<222> LOCATION: (13)..(13)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (17)..(17)
<223> OTHER INFORMATION: (S)-2-amino-2-methylhept-6-enoic acid or a stapled derivative thereof

<400> SEQUENCE: 62

```
Ile Leu Ser Arg Arg Pro Ser Tyr Arg Lys Ile Leu Xaa Asp Leu Ser
1               5                   10                  15

Xaa Asp Ala Pro Gly
            20
```

<210> SEQ ID NO 63
<211> LENGTH: 21
<212> TYPE: PRT
<213> ORGANISM: Artificial Sequence
<220> FEATURE:
<223> OTHER INFORMATION: p-KID "E" domain synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a stapled derivative thereof

<400> SEQUENCE: 63

```
Ile Leu Ser Arg Xaa Pro Ser Tyr Xaa Lys Ile Leu Asn Asp Leu Ser
1               5                   10                  15

Ser Asp Ala Pro Gly
            20
```

<210> SEQ ID NO 64
<211> LENGTH: 21
<212> TYPE: PRT
<213> ORGANISM: Artificial Sequence
<220> FEATURE:
<223> OTHER INFORMATION: p-KID "E" domain synthetic peptide
<220> FEATURE:

```
<221> NAME/KEY: MISC_FEATURE
<222> LOCATION: (10)..(10)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a
      stapled derivative thereof

<400> SEQUENCE: 64

Ile Leu Ser Arg Arg Pro Ser Tyr Arg Xaa Ile Leu Asn Xaa Leu Ser
1               5                   10                  15

Ser Asp Ala Pro Gly
            20


<210> SEQ ID NO 65
<211> LENGTH: 21
<212> TYPE: PRT
<213> ORGANISM: Artificial Sequence
<220> FEATURE:
<223> OTHER INFORMATION: p-KID "E" domain synthetic peptide
<220> FEATURE:
<221> NAME/KEY: MISC_FEATURE
<222> LOCATION: (7)..(7)
<223> OTHER INFORMATION: (R)-2-amino-2-methyldec-9-enoic acid or a
      stapled derivative thereof
<220> FEATURE:
<221> NAME/KEY: MISC_FEATURE
<222> LOCATION: (14)..(14)
<223> OTHER INFORMATION: (S)-2-amino-2-methylhept-6-enoic acid or a
      stapled derivative thereof

<400> SEQUENCE: 65

Ile Leu Ser Arg Arg Pro Xaa Tyr Arg Lys Ile Leu Asn Xaa Leu Ser
1               5                   10                  15

Ser Asp Ala Pro Gly
            20


<210> SEQ ID NO 66
<211> LENGTH: 21
<212> TYPE: PRT
<213> ORGANISM: Artificial Sequence
<220> FEATURE:
<223> OTHER INFORMATION: p-KID "E" domain synthetic peptide

<400> SEQUENCE: 66

Ile Leu Ser Arg Arg Pro Ser Tyr Arg Lys Ile Leu Asn Asp Leu Ser
1               5                   10                  15

Ser Asp Ala Pro Gly
            20


<210> SEQ ID NO 67
<211> LENGTH: 20
<212> TYPE: PRT
<213> ORGANISM: Artificial Sequence
<220> FEATURE:
<223> OTHER INFORMATION: Mad1 "E" domain synthetic peptide
<220> FEATURE:
<221> NAME/KEY: MISC_FEATURE
<222> LOCATION: (12)..(12)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (16)..(16)
<223> OTHER INFORMATION: (S)-2-amino-2-methylhept-6-enoic acid or a
      stapled derivative thereof

<400> SEQUENCE: 67
```

Val Arg Met Asn Ile Gln Met Leu Leu Glu Ala Xaa Asp Tyr Leu Xaa
1 5 10 15

Arg Arg Glu Arg
20

<210> SEQ ID NO 68
<211> LENGTH: 20
<212> TYPE: PRT
<213> ORGANISM: Artificial Sequence
<220> FEATURE:
<223> OTHER INFORMATION: Mad1 "E" domain synthetic peptide
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a stapled derivative thereof

<400> SEQUENCE: 68

Val Arg Met Asn Ile Gln Met Xaa Leu Glu Ala Xaa Asp Tyr Leu Glu
1 5 10 15

Arg Arg Glu Arg
20

<210> SEQ ID NO 69
<211> LENGTH: 20
<212> TYPE: PRT
<213> ORGANISM: Artificial Sequence
<220> FEATURE:
<223> OTHER INFORMATION: Mad1 "E" domain synthetic peptide
<220> FEATURE:
<221> NAME/KEY: MISC_FEATURE
<222> LOCATION: (9)..(9)
<223> OTHER INFORMATION: (R)-2-amino-2-methyldec-9-enoic acid or a stapled derivative thereof
<220> FEATURE:
<221> NAME/KEY: MISC_FEATURE
<222> LOCATION: (16)..(16)
<223> OTHER INFORMATION: (S)-2-amino-2-methylhept-6-enoic acid or a stapled derivative thereof

<400> SEQUENCE: 69

Val Arg Met Asn Ile Gln Met Leu Xaa Glu Ala Ala Asp Tyr Leu Xaa
1 5 10 15

Arg Arg Glu Arg
20

<210> SEQ ID NO 70
<211> LENGTH: 20
<212> TYPE: PRT
<213> ORGANISM: Artificial Sequence
<220> FEATURE:
<223> OTHER INFORMATION: Mad1 "E" domain synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof

<400> SEQUENCE: 70

```
Val Arg Met Xaa Ile Gln Met Xaa Leu Glu Ala Ala Asp Tyr Leu Glu
1               5                   10                  15

Arg Arg Glu Arg
            20


<210> SEQ ID NO 71
<211> LENGTH: 17
<212> TYPE: PRT
<213> ORGANISM: Homo sapiens

<400> SEQUENCE: 71

Leu Leu Thr Lys Pro Trp Asp Ile Ile Pro Met Val Thr Gln Met Ala
1               5                   10                  15

Met


<210> SEQ ID NO 72
<211> LENGTH: 10
<212> TYPE: PRT
<213> ORGANISM: Homo sapiens

<400> SEQUENCE: 72

Cys Leu Arg Arg Leu Glu Arg Leu Thr Leu
1               5                   10


<210> SEQ ID NO 73
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (2)..(2)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof

<400> SEQUENCE: 73

Lys Xaa Lys Arg Ile Xaa Glu Leu Glu Leu Leu Leu Met Ser Thr Glu
1               5                   10                  15

Asn Glu Leu Lys Gly
            20


<210> SEQ ID NO 74
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (2)..(2)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof

<400> SEQUENCE: 74

Lys Xaa Lys Arg Ile Xaa Arg Leu Glu Leu Leu Leu Met Ser Thr Glu
1               5                   10                  15
```

```
Asn Glu Leu Lys Gly
            20


<210> SEQ ID NO 75
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 75

Lys Glu Xaa Arg Ile Lys Xaa Leu Glu Leu Leu Leu Met Ser Thr Glu
1               5                   10                  15

Asn Glu Leu Lys Gly
            20


<210> SEQ ID NO 76
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 76

Lys Arg Xaa Arg Ile Lys Xaa Leu Glu Leu Leu Leu Met Ser Thr Glu
1               5                   10                  15

Asn Glu Leu Lys Gly
            20


<210> SEQ ID NO 77
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
      stapled derivative thereof

<400> SEQUENCE: 77

Lys Glu Xaa Arg Ile Lys Glu Leu Glu Xaa Leu Leu Met Ser Thr Glu
1               5                   10                  15

Asn Glu Leu Lys Gly
```

20

<210> SEQ ID NO 78
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
stapled derivative thereof

<400> SEQUENCE: 78

```
Lys Glu Xaa Arg Ile Lys Arg Leu Glu Xaa Leu Leu Met Ser Thr Glu
1               5                   10                  15

Asn Glu Leu Lys Gly
            20
```

<210> SEQ ID NO 79
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
stapled derivative thereof

<400> SEQUENCE: 79

```
Lys Arg Xaa Arg Ile Lys Glu Leu Glu Xaa Leu Leu Met Ser Thr Glu
1               5                   10                  15

Asn Glu Leu Lys Gly
            20
```

<210> SEQ ID NO 80
<211> LENGTH: 21
<212> TYPE: PRT
<213> ORGANISM: Artificial Sequence
<220> FEATURE:
<223> OTHER INFORMATION: c-Myb "E" domain synthetic peptide
<220> FEATURE:
<221> NAME/KEY: MISC_FEATURE
<222> LOCATION: (17)..(17)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (21)..(21)
<223> OTHER INFORMATION: (S)-2-amino-2-methylhept-6-enoic acid or a
stapled derivative thereof

<400> SEQUENCE: 80

```
Lys Glu Lys Arg Ile Lys Glu Leu Glu Leu Leu Leu Met Ser Thr Glu
1               5                   10                  15

Xaa Glu Leu Lys Xaa
            20
```

-continued

<210> SEQ ID NO 81
<211> LENGTH: 14
<212> TYPE: PRT
<213> ORGANISM: Artificial Sequence
<220> FEATURE:
<223> OTHER INFORMATION: MLL "E" domain synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof

<400> SEQUENCE: 81

Ile Leu Pro Xaa Asp Ile Met Xaa Phe Val Leu Lys Asn Thr
1 5 10

<210> SEQ ID NO 82
<211> LENGTH: 14
<212> TYPE: PRT
<213> ORGANISM: Artificial Sequence
<220> FEATURE:
<223> OTHER INFORMATION: MLL "E" domain synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof

<400> SEQUENCE: 82

Ile Leu Pro Xaa Arg Ile Met Xaa Phe Val Leu Lys Asn Thr
1 5 10

<210> SEQ ID NO 83
<211> LENGTH: 14
<212> TYPE: PRT
<213> ORGANISM: Artificial Sequence
<220> FEATURE:
<223> OTHER INFORMATION: MLL "E" domain synthetic peptide
<220> FEATURE:
<221> NAME/KEY: MISC_FEATURE
<222> LOCATION: (8)..(8)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a stapled derivative thereof

<400> SEQUENCE: 83

Ile Leu Pro Ser Asp Ile Met Xaa Phe Val Leu Xaa Asn Thr
1 5 10

<210> SEQ ID NO 84
<211> LENGTH: 14
<212> TYPE: PRT
<213> ORGANISM: Artificial Sequence
<220> FEATURE:
<223> OTHER INFORMATION: MLL "E" domain synthetic peptide
<220> FEATURE:
<221> NAME/KEY: MISC_FEATURE

```
<222> LOCATION: (8)..(8)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (12)..(12)
<223> OTHER INFORMATION: (S)-2-amino-2-methylhept-6-enoic acid or a
      stapled derivative thereof

<400> SEQUENCE: 84

Ile Leu Pro Ser Arg Ile Met Xaa Phe Val Leu Xaa Asn Thr
1               5                   10


<210> SEQ ID NO 85
<211> LENGTH: 24
<212> TYPE: PRT
<213> ORGANISM: Homo sapiens

<400> SEQUENCE: 85

Val Arg Met Asn Ile Gln Met Leu Leu Glu Ala Ala Asp Tyr Leu Glu
1               5                   10                  15

Arg Arg Glu Arg Glu Ala Glu His
            20


<210> SEQ ID NO 86
<211> LENGTH: 20
<212> TYPE: PRT
<213> ORGANISM: Homo sapiens

<400> SEQUENCE: 86

Val Arg Met Asn Ile Gln Met Leu Leu Glu Ala Ala Asp Tyr Leu Glu
1               5                   10                  15

Arg Arg Glu Arg
            20


<210> SEQ ID NO 87
<211> LENGTH: 20
<212> TYPE: PRT
<213> ORGANISM: Artificial Sequence
<220> FEATURE:
<223> OTHER INFORMATION: SID1 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a
      stapled derivative thereof

<400> SEQUENCE: 87

Xaa Glu Arg Leu Arg Arg Arg Ile Xaa Met Leu Leu Xaa Ala Ala Asn
1               5                   10                  15

Tyr Leu Glu Arg
            20


<210> SEQ ID NO 88
<211> LENGTH: 18
<212> TYPE: PRT
<213> ORGANISM: Artificial Sequence
<220> FEATURE:
<223> OTHER INFORMATION: SID2 synthetic peptide
```

<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (7)..(7)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (11)..(11)
<223> OTHER INFORMATION: (S)-2-amino-2-methylhept-6-enoic acid or a stapled derivative thereof

<400> SEQUENCE: 88

```
Xaa Val Arg Arg Arg Ile Xaa Met Leu Leu Xaa Ala Ala Asn Tyr Leu
1               5                   10                  15

Glu Arg
```

<210> SEQ ID NO 89
<211> LENGTH: 18
<212> TYPE: PRT
<213> ORGANISM: Artificial Sequence
<220> FEATURE:
<223> OTHER INFORMATION: SID3 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (11)..(11)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (15)..(15)
<223> OTHER INFORMATION: (S)-2-amino-2-methylhept-6-enoic acid or a stapled derivative thereof

<400> SEQUENCE: 89

```
Xaa Val Arg Arg Arg Ile Gln Arg Leu Leu Xaa Ala Ala Asn Xaa Leu
1               5                   10                  15

Glu Arg
```

<210> SEQ ID NO 90
<211> LENGTH: 21
<212> TYPE: PRT
<213> ORGANISM: Artificial Sequence
<220> FEATURE:
<223> OTHER INFORMATION: SID4 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (16)..(16)
<223> OTHER INFORMATION: (S)-2-amino-2-methylhept-6-enoic acid or a stapled derivative thereof
<220> FEATURE:
<221> NAME/KEY: MISC_FEATURE
<222> LOCATION: (20)..(20)
<223> OTHER INFORMATION: (S)-2-amino-2-methylhept-6-enoic acid or a stapled derivative thereof

<400> SEQUENCE: 90

```
Xaa Val Arg Met Asn Ile Gln Met Leu Leu Gln Ala Ala Asn Arg Xaa
1               5                   10                  15

Glu Arg Arg Xaa Arg
```

```
            20


<210> SEQ ID NO 91
<211> LENGTH: 21
<212> TYPE: PRT
<213> ORGANISM: Artificial Sequence
<220> FEATURE:
<223> OTHER INFORMATION: SID5 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (16)..(16)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (20)..(20)
<223> OTHER INFORMATION: (S)-2-amino-2-methylhept-6-enoic acid or a
      stapled derivative thereof

<400> SEQUENCE: 91

Xaa Val Arg Arg Arg Ile Gln Met Leu Leu Glu Ala Ala Asn Lys Xaa
1               5                   10                  15

Glu Arg Arg Xaa Arg
            20


<210> SEQ ID NO 92
<211> LENGTH: 25
<212> TYPE: PRT
<213> ORGANISM: Artificial Sequence
<220> FEATURE:
<223> OTHER INFORMATION: SID6 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (20)..(20)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (24)..(24)
<223> OTHER INFORMATION: (S)-2-amino-2-methylhept-6-enoic acid or a
      stapled derivative thereof

<400> SEQUENCE: 92

Xaa Val Arg Met Asn Ile Gln Met Leu Leu Gln Ala Ala Asn Arg Leu
1               5                   10                  15

Glu Arg Arg Xaa Arg Glu Ala Xaa His
            20                  25


<210> SEQ ID NO 93
<211> LENGTH: 25
<212> TYPE: PRT
<213> ORGANISM: Artificial Sequence
<220> FEATURE:
<223> OTHER INFORMATION: SID7 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (20)..(20)
<223> OTHER INFORMATION: (S)-2-amino-2-methylhept-6-enoic acid or a
      stapled derivative thereof
<220> FEATURE:
```

-continued

```
<221> NAME/KEY: MISC_FEATURE
<222> LOCATION: (24)..(24)
<223> OTHER INFORMATION: (S)-2-amino-2-methylhept-6-enoic acid or a
      stapled derivative thereof

<400> SEQUENCE: 93

Xaa Val Arg Arg Arg Ile Gln Met Leu Leu Glu Ala Ala Asn Lys Leu
1               5                   10                  15

Glu Arg Arg Xaa Arg Glu Ala Xaa His
            20                  25


<210> SEQ ID NO 94
<211> LENGTH: 18
<212> TYPE: PRT
<213> ORGANISM: Artificial Sequence
<220> FEATURE:
<223> OTHER INFORMATION: SID8 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (11)..(11)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (15)..(15)
<223> OTHER INFORMATION: (S)-2-amino-2-methylhept-6-enoic acid or a
      stapled derivative thereof

<400> SEQUENCE: 94

Xaa Val Arg Met Asn Ile Gln Met Leu Leu Xaa Ala Ala Asn Xaa Leu
1               5                   10                  15

Glu Arg


<210> SEQ ID NO 95
<211> LENGTH: 18
<212> TYPE: PRT
<213> ORGANISM: Artificial Sequence
<220> FEATURE:
<223> OTHER INFORMATION: SID9 synthetic peptide
<220> FEATURE:
<221> NAME/KEY: MISC_FEATURE
<222> LOCATION: (1)..(1)
<223> OTHER INFORMATION: beta-alanine
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (11)..(11)
<223> OTHER INFORMATION: (S)-2-amino-2-methylhept-6-enoic acid or a
      stapled derivative thereof

<400> SEQUENCE: 95

Xaa Val Arg Met Asn Ile Xaa Met Leu Leu Xaa Ala Ala Asn Tyr Leu
1               5                   10                  15

Glu Arg


<210> SEQ ID NO 96
<211> LENGTH: 14
<212> TYPE: PRT
<213> ORGANISM: Artificial Sequence
<220> FEATURE:
<223> OTHER INFORMATION: MLLneg1 synthetic peptide
<220> FEATURE:
```

-continued

<221> NAME/KEY: MISC_FEATURE
<222> LOCATION: (4)..(4)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a
stapled derivative thereof

<400> SEQUENCE: 96

Ile Leu Pro Xaa Arg Ile Met Xaa Phe Val Ala Lys Asn Thr
1 5 10

<210> SEQ ID NO 97
<211> LENGTH: 14
<212> TYPE: PRT
<213> ORGANISM: Artificial Sequence
<220> FEATURE:
<223> OTHER INFORMATION: MLLneg2 synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a
stapled derivative thereof

<400> SEQUENCE: 97

Ile Leu Pro Xaa Arg Ile Met Xaa Phe Ala Leu Lys Asn Thr
1 5 10

<210> SEQ ID NO 98
<211> LENGTH: 14
<212> TYPE: PRT
<213> ORGANISM: Artificial Sequence
<220> FEATURE:
<223> OTHER INFORMATION: MLLneg3 synthetic peptide
<220> FEATURE:
<221> NAME/KEY: MISC_FEATURE
<222> LOCATION: (4)..(4)
<223> OTHER INFORMATION: (S)-2-amino-2-methylhept-6-enoic acid or a
stapled derivative thereof
<220> FEATURE:
<221> NAME/KEY: MISC_FEATURE
<222> LOCATION: (8)..(8)
<223> OTHER INFORMATION: (S)-2-amino-2-methylhept-6-enoic acid or a
stapled derivative thereof

<400> SEQUENCE: 98

Ile Ala Pro Xaa Arg Ile Met Xaa Phe Val Leu Lys Asn Thr
1 5 10

<210> SEQ ID NO 99
<211> LENGTH: 14
<212> TYPE: PRT
<213> ORGANISM: Homo sapiens

<400> SEQUENCE: 99

Ile Leu Pro Ser Asp Ile Met Asp Phe Val Leu Lys Asn Thr
1 5 10